United States Patent
Kawano et al.

(10) Patent No.: US 8,444,550 B2
(45) Date of Patent: May 21, 2013

(54) CAPSULE MEDICAL DEVICE GUIDANCE SYSTEM AND METHOD FOR GUIDING CAPSULE MEDICAL DEVICE

(75) Inventors: Hironao Kawano, Hachioji (JP); Takeshi Nishiyama, Akishima (JP)

(73) Assignee: Olympus Medical Systems Corp., Tokyo (JP)

(*) Notice: Subject to any disclaimer, the term of this patent is extended or adjusted under 35 U.S.C. 154(b) by 78 days.

(21) Appl. No.: 13/020,264

(22) Filed: Feb. 3, 2011

(65) Prior Publication Data
US 2011/0275893 A1 Nov. 10, 2011

Related U.S. Application Data

(63) Continuation of application No. PCT/JP2010/063222, filed on Aug. 4, 2010.

(30) Foreign Application Priority Data

Nov. 9, 2009 (JP) ................................. 2009-256040

(51) Int. Cl.
*A61B 1/04* (2006.01)
*A61B 1/06* (2006.01)
*A61B 5/05* (2006.01)

(52) U.S. Cl.
USPC ........... 600/117; 600/109; 600/118; 600/160; 600/178; 600/424

(58) Field of Classification Search
USPC .......................... 600/103, 117, 118, 160, 178
See application file for complete search history.

(56) References Cited

U.S. PATENT DOCUMENTS

| | | | |
|---|---|---|---|
| 2008/0300453 A1* | 12/2008 | Aoki et al. ..................... | 600/103 |
| 2009/0299142 A1* | 12/2009 | Uchiyama et al. ............ | 600/118 |
| 2010/0156399 A1 | 6/2010 | Chiba et al. | |
| 2011/0054255 A1 | 3/2011 | Schmidt | |

FOREIGN PATENT DOCUMENTS

| | | |
|---|---|---|
| DE | 10 2008 018 723 B3 | 7/2009 |
| EP | 1 967 125 A1 | 9/2008 |
| EP | 1 972 253 A1 | 9/2008 |
| JP | 2007-175447 A | 7/2007 |

(Continued)

OTHER PUBLICATIONS

European Search Report dated Apr. 17, 2012 from corresponding European Patent Application No. EP 10 82 8139.5.

*Primary Examiner* — Philip R Smith
*Assistant Examiner* — Rynae Boler
(74) *Attorney, Agent, or Firm* — Scully, Scott, Murphy & Presser, P.C

(57) ABSTRACT

A capsule guidance system includes a capsule including an imaging unit that captures an in-vivo image, a transmitting unit that transmits the image, and a magnetic field response unit; a magnetic field generation unit that generates a magnetic field; a receiving unit that receives the image; a display unit that displays the image; an operation input unit that inputs operation information for magnetically guiding the capsule; a control unit that controls the magnetic field generation unit to guide the capsule in accordance with the operation information; and a selection unit that selects at least two of a liquid surface, a submerged area, and a liquid bottom that is a lower boundary surface between the liquid and the outside as guidance areas into which the capsule medical device is guided. The control unit switches the magnetic field to be generated in accordance with the selected guidance area.

6 Claims, 32 Drawing Sheets

FOREIGN PATENT DOCUMENTS

| | | |
|---|---|---|
| WO | WO 2007/074888 A1 | 7/2007 |
| WO | WO 2007/077922 A1 | 7/2007 |
| WO | WO 2009/031456 A1 | 3/2009 |

\* cited by examiner

| GUIDANCE AREA | LIQUID SURFACE (INCLUDING UPPER SURFACE OF STOMACH WALL) | SUBMERGED AREA | LIQUID BOTTOM |
|---|---|---|---|
| TYPE OF MAGNETIC FIELD | PEAK MAGNETIC FIELD + VERTICAL DIRECTION GRADIENT MAGNETIC FIELD | UNIFORM GRADIENT MAGNETIC FIELD + UNIFORM MAGNETIC FIELD | UNIFORM GRADIENT MAGNETIC FIELD + UNIFORM MAGNETIC FIELD |

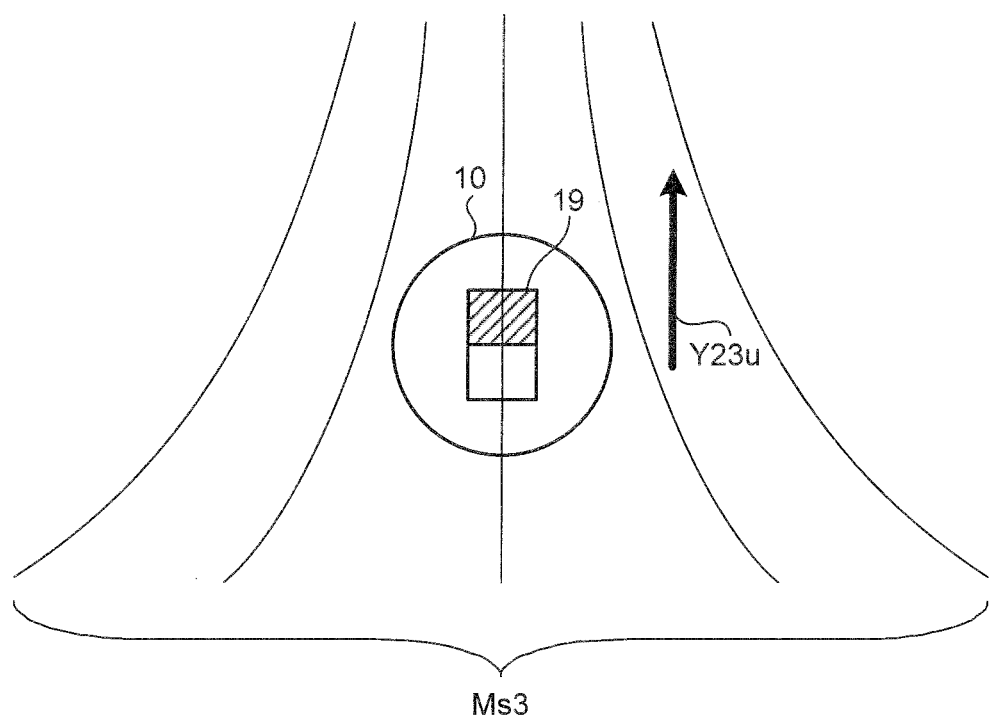

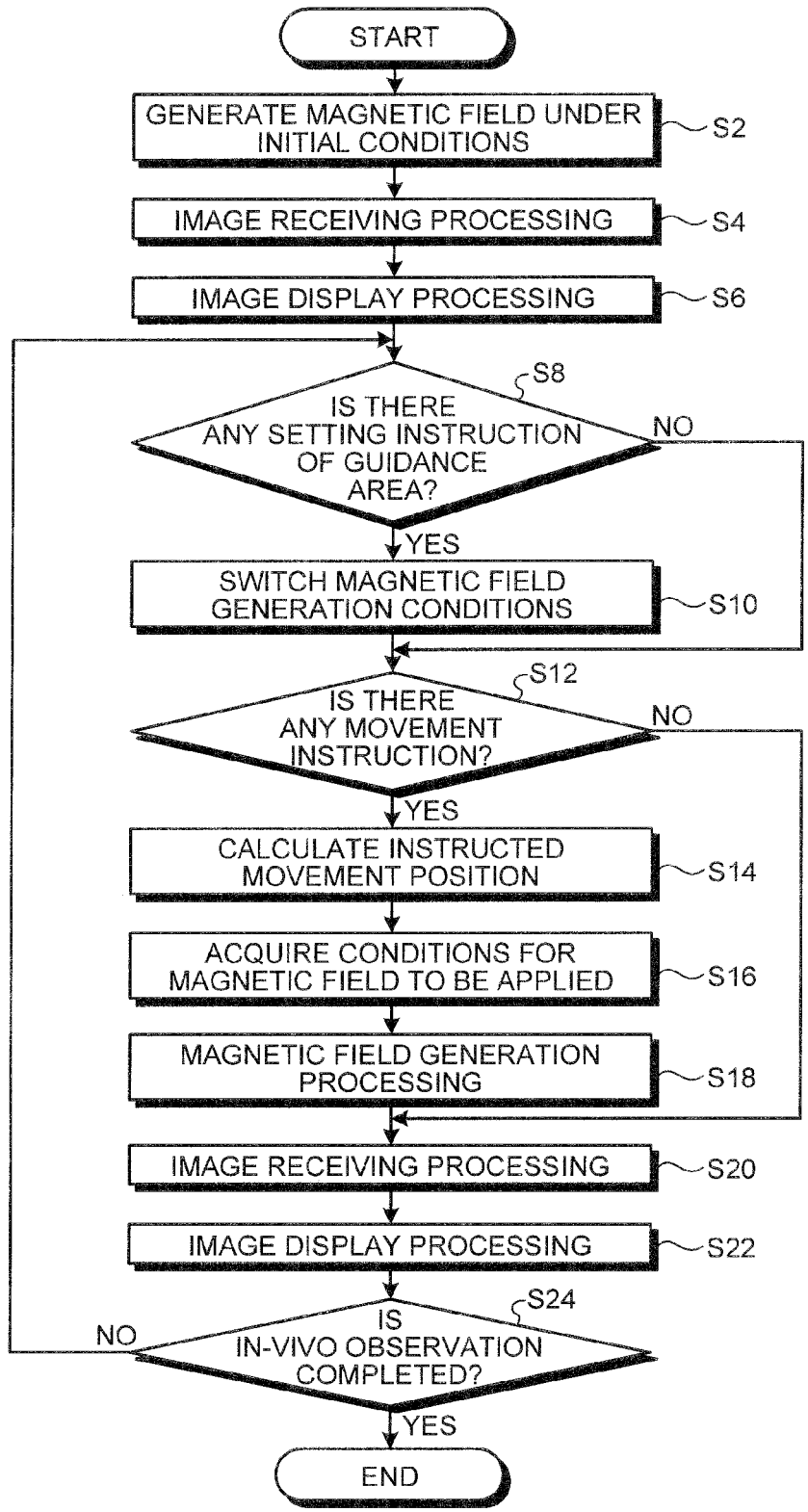

(1)    (2)

(1)    (2)

CAPSULE MEDICAL DEVICE GUIDANCE SYSTEM AND METHOD FOR GUIDING CAPSULE MEDICAL DEVICE

CROSS-REFERENCE TO RELATED APPLICATIONS

This application is a continuation of PCT international application Ser. No. PCT/JP2010/063222 filed on Aug. 4, 2010 which designates the United States, incorporated herein by reference, and which claims the benefit of priority from Japanese Patent Application No. 2009-256040, filed on Nov. 9, 2009, incorporated herein by reference.

BACKGROUND OF THE INVENTION

1. Field of the Invention

The present invention relates to a capsule medical device guidance system that guides a capsule medical device introduced into a subject.

2. Description of the Related Art

In the field of endoscope, capsule medical devices equipped with an imaging function and a radio communication function inside a capsule-shaped casing formed into a size introducible into a digestive tract of a subject such as a patient have been known. After being swallowed through the mouth of a subject, a capsule medical device moves through the digestive tract by dint of peristaltic movement or the like. In the period between the time when such a capsule medical device is introduced into the digestive tract of a subject and the time when the capsule medical device is discharged out of the subject, the capsule medical device successively acquires images inside organs (hereinafter, may be referred to as in-vivo images) of the subject and wirelessly transmits the acquired in-vivo images to a receiving device outside the subject.

Each in-vivo image captured by such a capsule medical device is loaded into an image display device via the receiving device. The image display device displays each captured in-vivo image in a display as a still image or a moving image. A user such as a physician or a nurse observes each in-vivo image of the subject displayed in the image display device to make an examination inside an organ of the subject through the observation of each in-vivo image.

On the other hand, in recent years, capsule medical device guidance systems that guide a capsule medical device inside a subject by a magnetic force (hereinafter, referred to as magnetic guidance) are proposed. Generally in a capsule medical device guidance system, a capsule medical device is further equipped with a permanent magnet inside a capsule-shaped casing and an image display device displays each in-vivo image successively captured by the capsule medical device inside a subject in real time. The capsule medical device guidance system applies a magnetic field to the capsule medical device inside the subject to magnetically guide the capsule medical device inside the subject to a desired position by a magnetic force of the applied magnetic field. A user operates magnetic guidance of the capsule medical device by using an operation unit of the capsule medical device guidance system while referring to an in-vivo image displayed in the image display device.

Among such capsule endoscopes, a capsule endoscope that has a specific gravity floatable in a liquid introduced into an organ to make an observation inside such a relatively large-space organ such as the stomach or large intestine and successively captures in-vivo images while floating in the liquid is known. And there is a case when a subject is made to take in a liquid to expand the inside of an organ (more specifically, a wall of an organ inner wall) to make a concentrated examination inside such a relatively large-space organ such as the stomach and a capsule endoscope having a specific gravity smaller than that of the liquid (see, for example, WO 2007/077922). In this case, the capsule endoscope successively captures images inside the organ expanded by the liquid while floating in the liquid in a mode to take a predetermined posture (for example, a vertical posture in which the center axis of the capsule endoscope in a longitudinal direction and the liquid surface are substantially perpendicular) inside the organ such as the stomach. Such a capsule endoscope can capture images in a wider range inside the organ by moving in a desired direction while floating in the liquid inside the organ.

SUMMARY OF THE INVENTION

A capsule medical device guidance system according to an aspect of the present invention includes a capsule medical device to be introduced into a subject, the capsule medical device including an imaging unit that captures an in-vivo image of the subject, a transmitting unit that transmits the image captured by the imaging unit to an outside, and a magnetic field response unit; a magnetic field generation unit that generates a magnetic field for the magnetic field response unit to magnetically guide the capsule medical device; a receiving unit that receives the in-vivo image of the subject transmitted by the capsule medical device; a display unit that displays the in-vivo image of the subject received by the receiving unit; an operation input unit that inputs operation information for magnetically guiding the capsule medical device; a control unit that controls the magnetic field generation unit to guide the capsule medical device in accordance with the operation information input by the operation input unit; and a selection unit that selects one combination from among combinations that combine at least two of a liquid surface that is an upper boundary surface between a liquid inside the subject and the outside, a submerged area, and a liquid bottom that is a lower boundary surface between the liquid and the outside as guidance areas into which the capsule medical device is guided. The control unit switches the magnetic field to be generated by the magnetic field generation unit in accordance with the guidance area selected by the selection unit.

A capsule medical device guidance system according to another aspect of the present invention includes a capsule medical device to be introduced into a subject, the capsule medical device including an imaging means for capturing an in-vivo image of the subject, a transmitting means for transmitting the image captured by the imaging means to an outside, and a magnetic field responding means; a magnetic field generating means for generating a magnetic field for the magnetic field responding means to magnetically guide the capsule medical device; a receiving means for receiving the in-vivo image of the subject transmitted by the capsule medical device; a display means for displaying the in-vivo image of the subject received by the receiving means; an operation input means for inputting operation information for magnetically guiding the capsule medical device; a control means for controlling the magnetic field generating means to guide the capsule medical device in accordance with the operation information input by the operation input means; and a selecting means for selecting one combination from among combinations that combine at least two of a liquid surface that is an upper boundary surface between a liquid inside the subject and the outside, a submerged area, and a liquid bottom that is a lower boundary surface between the liquid and the outside as guidance areas into which the capsule medical device is guided. The control means switches the magnetic field to be generated by the magnetic field generating means in accordance with the guidance area selected by the selecting means.

A capsule medical device guiding method according to still another aspect of the present invention is for magnetically guiding a capsule medical device to be introduced into a subject, the capsule medical device including an imaging unit that captures an in-vivo image of the subject, a transmitting unit that transmits the image captured by the imaging unit to an outside, and a magnetic field response unit. The capsule medical device guiding method includes receiving, by a receiving device, the in-vivo image of the subject transmitted by the capsule medical device; displaying the received in-vivo image of the subject by a display device; selecting, by a selection unit, one combination from among combinations that combine at least two of a liquid surface that is an upper boundary surface between a liquid inside the subject and the outside, a submerged area, and a liquid bottom that is a lower boundary surface between the liquid and the outside as guidance areas into which the capsule medical device is guided; and causing, by a control unit, a magnetic field generation device to generate a magnetic field to guide the capsule medical device in accordance with the selected guidance area.

The above and other features, advantages and technical and industrial significance of this invention will be better understood by reading the following detailed description of presently preferred embodiments of the invention, when considered in connection with the accompanying drawings.

BRIEF DESCRIPTION OF THE DRAWINGS

FIG. 17 is a diagram exemplifying the uniform gradient magnetic field generated by the magnetic field generation unit shown in FIG. 1;

FIG. 19 is a flow chart showing a processing procedure for guidance processing of the capsule endoscope of the capsule medical device guidance system shown in FIG. 1;

DETAILED DESCRIPTION OF THE PREFERRED EMBODIMENTS

Figure 1:
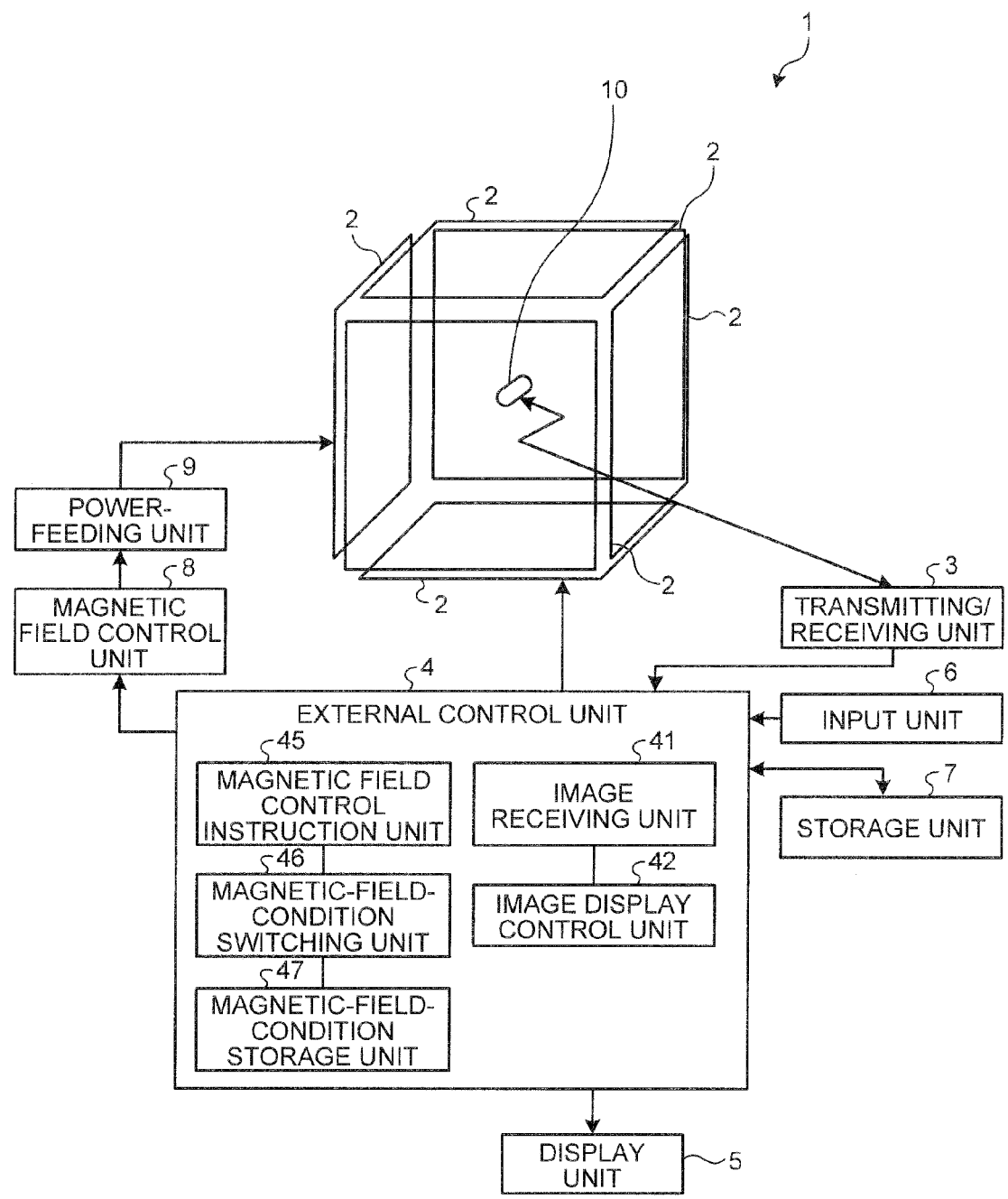
FIG. 1 is a schematic view showing an overall configuration of a capsule medical device guidance system according to a first embodiment.

Capsule medical device guidance systems that are the embodiments according to the present invention will be described by taking a capsule medical device system that uses a capsule endoscope orally introduced into a subject and floating in a liquid accumulated in the stomach, small intestine, large intestine or the like of the subject as a body-insertable apparatus as an example. However, the body-insertable apparatus is not limited to this and various body-insertable apparatuses such as a single-lens or double-lens capsule endoscope that acquires in-vivo images inside the subject by performing an imaging operation while moving inside lumina, for example, from esophagus to anal of the subject. The present invention is not limited by the embodiments. The same reference numerals are attached to the same units in the drawings.

First Embodiment

First, a first embodiment will be described. FIG. 1 is a schematic view showing an overall configuration of a capsule medical device guidance system according to the first embodiment of the invention. As shown in FIG. 1, a capsule medical device guidance system 1 according to the first embodiment includes a capsule endoscope 10, which is a capsule medical device that communicates with an external device after being swallowed through the mouth of a subject and introduced into a body cavity of the subject. The capsule medical device guidance system 1 includes a magnetic field generation unit 2 provided around the subject and capable of generating a three-dimensional magnetic field. The capsule medical device guidance system 1 includes a transmitting/receiving unit 3 that performs radio communication with the capsule endoscope 10 to receive a radio signal containing images captured by the capsule endoscope 10 and also transmits an operation signal to the capsule endoscope 10. The capsule medical device guidance system 1 includes an external control unit 4 that controls each element of the capsule medical device guidance system 1. The capsule medical device guidance system 1 includes a display unit 5 that displays/outputs an image captured by the capsule endoscope 10. The capsule medical device guidance system 1 includes an input unit 6 that inputs instruction information to instruct various operations in the capsule medical device guidance system 1 such as operation information to magnetically guide the capsule endoscope 10 into the external control unit 4. The capsule medical device guidance system 1 includes a storage unit 7 that stores image information captured by the capsule endoscope 10 or the like. The capsule medical device guidance system 1 includes a magnetic field control unit 8 that controls a magnetic field related to the magnetic field generation unit 2. The capsule medical device guidance system 1 includes a power-feeding unit 9 that feeds power under control of the magnetic field control unit 8 to the magnetic field generation unit 2.

Incidentally, the transmitting/receiving unit 3 may detect the position and posture of the capsule endoscope 10 inside the subject based on the received magnetic field strength of a signal transmitted by the capsule endoscope 10. Alternatively, a position detection device to detect the position and posture of the capsule endoscope 10 may be separately provided. For example, the position and posture of the capsule endoscope 10 may be detected based on detection results by magnetic field sensors by providing a magnetic field generation unit or magnetic field reflection unit in the capsule endoscope 10 and a plurality of magnetic field sensors as if to surround, like the magnetic field generation unit 2, the capsule endoscope 10.

The capsule endoscope 10 is a capsule medical device that acquires in-vivo images of a subject and contains an imaging function and a radio communication function. The capsule endoscope 10 is introduced into an organ of the subject through oral ingestion. Then, the capsule endoscope 10 inside the subject moves through the digestive tract before being discharged out of the subject in the end. In the period between the time when the capsule endoscope 10 is introduced into a subject and the time when the capsule endoscope 10 is discharged out of the subject, the capsule endoscope 10 successively captures in-vivo images of the subject and successively transmits the obtained in-vivo images wirelessly to the external transmitting/receiving unit 3. The capsule endoscope 10 contains a magnetic substance such as a permanent magnet. The capsule endoscope 10 floats in a liquid introduced into an organ (for example, into the stomach) of the subject and is magnetically guided by the external magnetic field generation unit 2.

The magnetic field generation unit 2 is intended to magnetically guide a capsule medical device inside a subject. The magnetic field generation unit 2 is realized by using, for example, a plurality of coils and generates a magnetic field for guidance by using power fed by the power-feeding unit 9. The magnetic field generation unit 2 applies the generated magnetic field for guidance to the magnetic substance inside the capsule endoscope 10 to magnetically trap the capsule endoscope 10 by action of the magnetic field for guidance. The magnetic field generation unit 2 controls the three-dimensional posture of the capsule endoscope 10 inside the subject by changing the magnetic field direction of the magnetic field for guidance acting on the capsule endoscope 10 inside the subject.

The transmitting/receiving unit 3 includes a plurality of antennas and receives in-vivo images of a subject from the capsule endoscope 10 via the plurality of antennas. The transmitting/receiving unit 3 successively receives a radio signal from the capsule endoscope 10 via the plurality of antennas. The transmitting/receiving unit 3 selects the antenna with the strongest received electric field strength from among the plurality of antennas and performs demodulation processing and the like on a radio signal from the capsule endoscope 10 received via the selected antenna. Accordingly, the transmitting/receiving unit 3 extracts image data by the capsule endoscope 10, that is, in-vivo image data of the subject from the radio signal. The transmitting/receiving unit 3 transmits an image signal containing the extracted in-vivo image data to the external control unit 4.

The external control unit 4 controls each operation of the magnetic field generation unit 2, the display unit 5, the storage unit 7, and the magnetic field control unit 8 and also controls input/output of signals between these elements. The external control unit 4 includes an image receiving unit 41 that successively acquires in-vivo images successively received by the transmitting/receiving unit 3 and an image display control unit 42 that causes the display unit 5 to display in-vivo images successively received by the transmitting/receiving unit 3 in real time. The external control unit 4 controls the storage unit 7 to store a group of in-vivo images of the subject acquired from the transmitting/receiving unit 3. When instruction information to instruct selective storage of in-vivo images is input through the input unit 6, the image display control unit 42 extracts in-vivo images instructed by the instruction information (that is, user-selected images) to store from among a group of in-vivo images of the subject and controls the display unit 5 to additionally display reduced images (thumbnail images or the like) of the in-vivo images.

The external control unit 4 includes a magnetic field control instruction unit 45 that issues instructions of magnetic field generation conditions to the magnetic field control unit 8 to guide the capsule endoscope 10 in accordance with operation information input through the input unit 6. The external control unit 4 includes a magnetic-field-condition switching unit 46 that switches the magnetic field the magnetic field generation unit 2 is caused to generate. The external control unit 4 includes a magnetic-field-condition storage unit 47 that stores each magnetic field condition. When operation information of the capsule endoscope 10 is input through the input unit 6, the magnetic field control instruction unit 45 issues instructions to the magnetic field control unit 8 to generate a magnetic field in accordance with the magnetic guidance direction and magnetic guidance position specified by the operation information.

The display unit 5 is realized by using various displays such as a liquid crystal display and displays various kinds of information instructed to display by the external control unit 4. More specifically, the display unit 5 displays, for example, a group of in-vivo images of a subject captured by the capsule endoscope 10 based on control of the image display control unit 42 in the external control unit 4. The display unit 5 also displays reduced images of in-vivo images selected or marked by an input operation through the input unit 6 from the group of in-vivo images, patient information of a subject, and examination information.

The input unit 6 includes input devices such as a keyboard and mouse and inputs various kinds of information into the external control unit 4 in accordance with an input operation by an operator such as a physician. Various kinds of information input into the external control unit 4 by the input unit 6 include, for example, instruction information issuing instructions to the external control unit 4 and patient information and examination information of a subject. The patient information of a subject is identification information to identify the subject such as the patient name of the subject, patient ID, date of birth, sex, and age. The examination information of a subject is identification information to identify the examination to make an observation inside the digestive tract by introducing the capsule endoscope 10 into the digestive tract of the subject and is, for example, the examination ID and examination date. The input unit 6 also inputs operation information to operate magnetic guidance of the capsule endoscope 10 by the magnetic field generation unit 2. The input unit 6 further includes, for example, an operation input unit having a joystick. Operation information to magnetically guide the capsule endoscope 10 such as the magnetic guidance direction and magnetic guidance position of the capsule endoscope 10 to be operated by magnetic guidance is input into the external control unit 4 by, for example, the joystick being operated by a physician.

The storage unit 7 is realized by using a storage medium that rewritably stores information such as a flash memory or hard disk. The storage unit 7 stores various kinds of information instructed to store by the external control unit 4 and sends information instructed to read from various kinds of stored information by the external control unit 4 to the external control unit 4. Various kinds of information stored by the storage unit 7 include, for example, image data of a group of in-vivo images of a subject captured by the capsule endoscope 10, data of in-vivo images selected by an input operation through the input unit 6 from among in-vivo images displayed by the display unit 5, and input information of patient information of a subject and the like through the input unit 6.

The magnetic field control unit 8 controls the quantity of power of the power-feeding unit 9 fed to the magnetic field generation unit 2 based on instruction information instructed by the external control unit 4 and, through control of the power-feeding unit 9, controls the magnetic field generation unit 2 so that a magnetic field for guidance necessary to magnetically guide the capsule endoscope 10 in accordance with the magnetic guidance direction and magnetic guidance position of the capsule endoscope 10 based on the operation information is generated.

The power-feeding unit 9 feeds power (for example, an AC current) necessary to generate the above magnetic field for guidance to the magnetic field generation unit 2 based on control of the external control unit 4 and the magnetic field control unit 8. In this case, the power-feeding unit 9 feeds necessary power to each of a plurality of coils contained in the magnetic field generation unit 2 as appropriate. The magnetic field direction and magnetic field strength of the magnetic field for guidance by the above magnetic field generation unit 2 is controlled by the quantity of power to each coil in the magnetic field generation unit 2 from the power-feeding unit 9.

Figure 2:
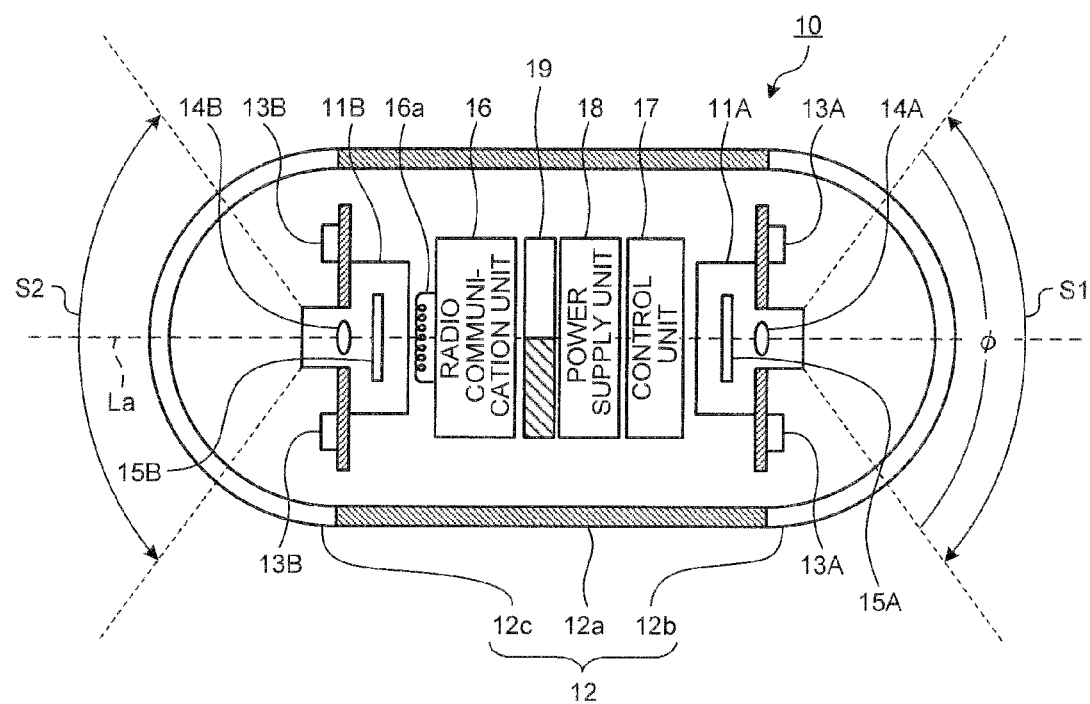
FIG. 2 is a sectional schematic view showing a configuration example of a capsule endoscope shown in FIG. 1.

Next, the capsule endoscope 10 will be described. FIG. 2 is a sectional schematic view showing a configuration example of the capsule endoscope shown in FIG. 1. As shown in FIG. 2, the capsule endoscope 10 includes a capsule-shaped casing 12, which is an outer jacket formed into a size easily introducible into an organ of a subject and imaging units 11A, 11B that capture images of the subject from mutually different imaging directions. The capsule endoscope 10 includes a radio communication unit 16 that wirelessly transmits each image captured by the imaging units 11A, 11B to the outside, a control unit 17 that controls each element of the capsule endoscope 10, and a power supply unit 18 that feeds power to each element of the capsule endoscope 10. Further, the capsule endoscope 10 includes a permanent magnet 19 to enable the above magnetic guidance by the magnetic field generation unit 2. The permanent magnet functions as a magnetic field response unit.

The capsule-shaped casing 12 is an outer casing formed into a size introducible into an organ of a subject and is configured to close open ends on both sides of a cylindrical casing 12a by dome-shaped casings 12b, 12c. The dome-shaped casings 12b, 12c are dome-shaped optical members transparent to light in a predetermined wavelength band such as visible light. The cylindrical casing 12a is a colored casing substantially opaque to visible light. The capsule-shaped casing 12 having the cylindrical casing 12a and the dome-shaped casings 12b, 12c fluid-tightly includes, as shown in FIG. 2, the imaging units 11A, 11B, the radio communication unit 16, the control unit 17, the power supply unit 18, and the permanent magnet 19.

The imaging units 11A, 11B captures images in mutually different imaging directions. More specifically, the imaging unit 11A includes an illumination unit 13A such as an LED, an optical system 14A of a condenser lens, and an image pickup device 15A such as a CMOS image sensor or CCD. The illumination unit 13A emits illumination light such as white light to an imaging field of view S1 of the image pickup device 15A to illuminate an object (for example, the inner wall of an organ on the side of the imaging field of view S1 inside the subject) within the imaging field of view S1 beyond the dome-shaped casing 12b. The optical system 14A condenses reflected light from the imaging field of view S1 onto an imaging surface of the image pickup device 15A to form an object image in the imaging field of view S1 on the imaging surface of the image pickup device 15A. The image pickup device 15A receives the reflected light from the imaging field of view S1 via the imaging surface and performs photoelectric conversion processing on the received optical signal to capture an object image in the imaging field of view S1, that is, an in-vivo image of the subject. The imaging unit 11B includes an illumination unit 13B such as an LED, an optical system 14B of a condenser lens and the like, and an image pickup device 15B such as a CMOS image sensor or CCD. The illumination unit 13B emits illumination light such as white light to an imaging field of view S2 of the image pickup device 15B to illuminate an object (for example, the inner wall of an organ on the side of the imaging field of view S2 inside the subject) within the imaging field of view S2 beyond the dome-shaped casing 12c. The optical system 14B condenses reflected light from the imaging field of view S2 onto the imaging surface of the image pickup device 15B to form an object image in the imaging field of view S2 on the imaging surface of the image pickup device 15B. The image pickup device 15B receives the reflected light from the imaging field of view S2 via the imaging surface and performs photoelectric conversion processing on the received optical signal to capture an object image in the imaging field of view S2, that is, an in-vivo image of the subject.

If the capsule endoscope 10 is, as shown in FIG. 2, a double-lens capsule medical device that captures images in forward and backward directions of a long axis La direction, each optical axis of the imaging units 11A, 11B is substantially parallel to or substantially matches the long axis La, which is the center axis of the capsule-shaped casing 12 in the longitudinal direction. Directions of the imaging fields of view S1, S2 of the imaging units 11A, 11B, that is, imaging directions of the imaging units 11A, 11B are directions opposite to each other.

The radio communication unit 16 includes an antenna 16a and successively transmits each image captured by the above imaging units 11A, 11B wirelessly to the outside via the antenna 16a. More specifically, the radio communication unit 16 acquires an image signal of an in-vivo image of a subject captured by the imaging unit 11A or 11B from the control unit 17 and performs modulation processing on the acquired image signal to generate a radio signal obtained by modulating the image signal. The radio communication unit 16 transmits the radio signal to the external transmitting/receiving unit 3 via the antenna 16a.

The control unit 17 controls each operation of the imaging units 11A, 11B and the radio communication unit 16, which are elements of the capsule endoscope 10, and also controls input/output of signals between such elements. More specifically, the control unit 17 causes the image pickup device 15A to capture an image of an object within the imaging field of view S1 illuminated by the illumination unit 13A and causes the image pickup device 15B to capture an image of an object within the imaging field of view S2 illuminated by the illumination unit 13B. The control unit 17 also has a signal processing function to generate an image signal. The control unit 17 acquires in-vivo image data in the imaging field of view S1 from the image pickup device 15A and performs predetermined signal processing on the in-vivo image data each time to generate an image signal containing the in-vivo image data in the imaging field of view S1. Similarly, the control unit 17 acquires in-vivo image data in the imaging field of view S2 from the image pickup device 15B and performs predetermined signal processing on the in-vivo image data each time to generate an image signal containing the in-vivo image data in the imaging field of view S2. The control unit 17 controls the radio communication unit 16 to wirelessly transmit each of such image signals successively to the outside in chronological order.

The power supply unit 18 is a button-type battery or a storage unit such as a capacitor and also includes a switch unit such as a magnetic switch. The power supply unit 18 switches the ON/OFF state of the power supply by a magnetic field applied from outside and, in the ON state, feeds power of the storage unit to each element (the imaging units 11A, 11B, the radio communication unit 16, and the control unit 17) of the capsule endoscope 10 as appropriate. The power supply unit 18 stops, in the OFF state, feeding of power to each element of the capsule endoscope 10.

The permanent magnet 19 enables magnetic guidance of the capsule endoscope 10 by the magnetic field generation unit 2. The permanent magnet 19 is fixedly arranged inside the capsule-shaped casing 12 in a relatively fixed state with respect to the above imaging units 11A, 11B. In this case, the permanent magnet 19 is magnetized in a known direction relatively fixed with respect to an up/down direction of each imaging surface of the image pickup devices 15A, 15B.

Figure 3:
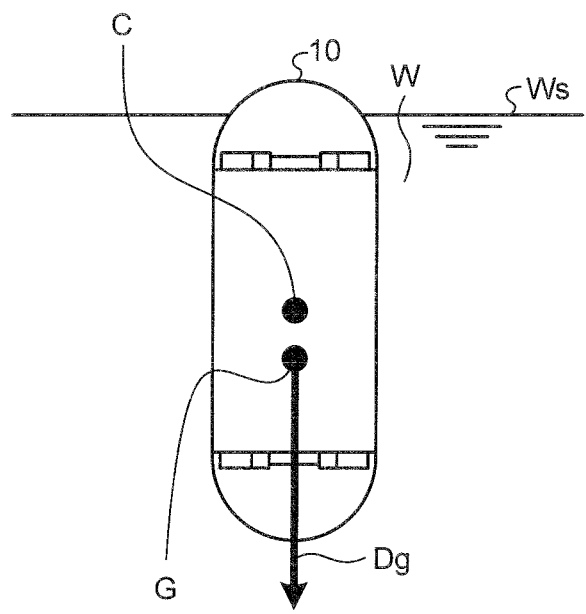
FIG. 3 is a conceptual diagram showing a case when the capsule endoscope is caused to float in a liquid introduced into a subject.

A case when the capsule endoscope 10 is caused to float in a liquid W introduced into a subject will be described using FIG. 3. FIG. 3 is a conceptual diagram showing a case when the capsule endoscope 10 is caused to float in the liquid W introduced into a subject. In the example shown in FIG. 3, however, a case when a magnetic field to control the posture (orientation of the long axis La direction) of the capsule endoscope 10 does not act on the permanent magnet 19 is illustrated.

The capsule endoscope 10 illustrated in the first embodiment has a specific gravity with respect to the liquid W smaller than 1. Thus, as shown in FIG. 3, the capsule endoscope 10 floats in the liquid W. In this case, a center of gravity G of the capsule endoscope 10 is shifted along the long axis La (see FIG. 2) of the capsule endoscope 10 from a geometrical center C of the capsule endoscope 10. More specifically, the center of gravity G of the capsule endoscope 10 is set to a position on the long axis La and deviating to the side of the imaging unit 11B from the geometrical center C of the capsule-shaped casing 12 by adjusting the arrangement of each element of the capsule endoscope 10 such as the power supply unit 18 and the permanent magnet 19. Accordingly, the long axis La of the capsule endoscope 10 floating in the liquid W is parallel to the vertical direction (that is, a gravity direction Dg). In other words, the capsule endoscope 10 can be caused to float in the liquid W in an upright state. The upright posture here is a posture in which the long axis La (straight line connecting the geometrical center C and the center of gravity G) of the capsule-shaped casing 12 and the vertical direction are substantially parallel. In such an upright posture, the capsule endoscope 10 directs the imaging field of view S1 of the imaging unit 11A vertically upward and directs the imaging field of view S2 of the imaging unit 11B vertically downward. The long axis La of the capsule endoscope 10 is the center axis of the capsule endoscope 10 in the longitudinal direction. The liquid W is a liquid harmless to the human body such as water and physiological saline. A portion of the capsule endoscope 10 need not necessarily be floated above a liquid surface Ws and the specific gravity of the capsule endoscope 10 with respect to the liquid W may be set so that the capsule endoscope 10 is submerged in the liquid W.

Figure 4:
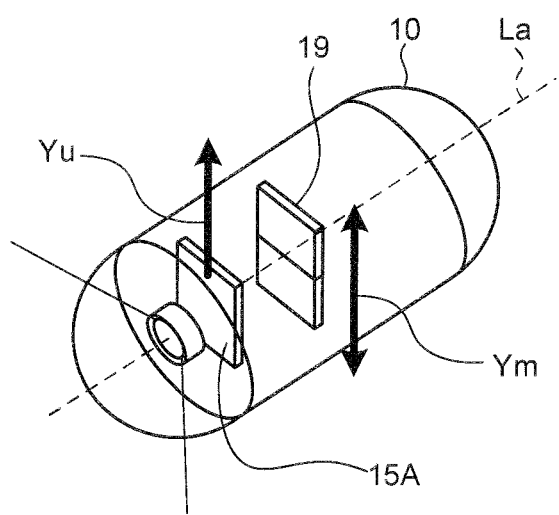
FIG. 4 is a diagram illustrating a magnetization direction of a permanent magnet of the capsule endoscope.

As shown in FIG. 4, the permanent magnet 19 is fixed to the inside of the capsule-shaped casing 12 in such a way that a magnetization direction Ym thereof has an inclination (for example, perpendicular) with respect to the long axis La of the capsule endoscope 10. More specifically, the permanent magnet 19 is fixed to the inside of the capsule-shaped casing 12 in such a way that the magnetization direction Ym is perpendicular to the long axis La. With this configuration, the magnetization direction Ym of the permanent magnet 19 inside the capsule endoscope 10 is the horizontal direction when floating in the liquid W. Moreover, the plane containing the magnetization direction Ym of the permanent magnet 19 and the direction (deviation direction) of the center of gravity G of the capsule endoscope 10 deviating from the geometrical center C of the capsule-shaped casing 12 is a vertical plane. Thus, when a magnetic field is applied, the posture of the capsule endoscope 10 changes so that the vertical plane with respect to the magnetic field contains the magnetization direction Ym. The permanent magnet 19 operates following a magnetic field applied from outside and, as a result, magnetic guidance of the capsule endoscope 10 by the magnetic field generation unit 2 is realized. In this case, the capsule endoscope 10 performs an operation to change at least one of the position, posture, and direction inside a subject with the action of the permanent magnet 19. For example, the tip of the capsule endoscope 10 can be caused to oscillate by applying a rotating magnetic field rotating around one point on the vertical axis to the permanent magnet 19. Also by applying a magnetic field rotating around the vertical axis to the permanent magnet 19, the capsule endoscope 10 can be caused to rotate around the vertical axis. Or, the capsule endoscope 10 maintains a stopped state in a desired position inside the subject by the action of the permanent magnet 19.

Next, the relative relationship between the image pickup devices 15A, 15B and the permanent magnet 19 contained in the capsule endoscope 10 will be described. As shown in FIGS. 2 and 4, the two imaging units 11A, 11B are arranged so that, for example, the optical center axis of the respective image pickup devices 15A, 15B overlaps with the long axis La and the respective imaging direction is directed toward mutually opposite directions. That is, the imaging units 11A, 11B are mounted so that the imaging surfaces of the image pickup devices 15A, 15B are perpendicular to the long axis La. Then, the permanent magnet 19 is arranged inside the capsule-shaped casing 12 while being fixed relative to the image pickup devices 15A, 15B. In this case, the permanent magnet 19 is arranged inside the capsule endoscope 10 so that the magnetization direction Ym of the permanent magnet 19 is, as shown in FIG. 4, parallel to an up/down direction Yu of each imaging surface of the image pickup devices 15A, 15B. By positioning the center of gravity G on the long axis La and mounting the imaging units 11A, 11B so that the imaging surfaces of the image pickup devices 15A, 15B are perpendicular to the long axis La, the imaging surfaces of the image pickup devices 15A, 15B can be made orthogonal to the plane containing the magnetization direction of the permanent magnet 19 and the deviation direction of the center of gravity G from the geometrical center C.

Figure 5:
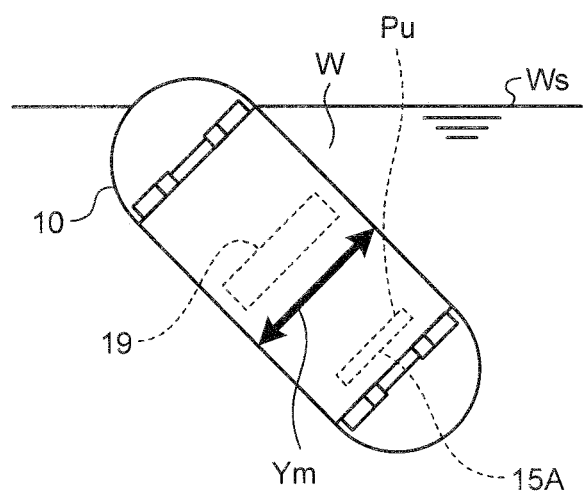
FIG. 5 is a conceptual diagram exemplifying a posture of the capsule endoscope in the liquid introduced into the subject.

The inclination of the long axis La of the capsule endoscope 10 with respect to the gravity direction Dg can be controlled by acting a magnetic field on the permanent magnet 19 of the capsule endoscope 10 from outside. By acting, as shown in FIG. 5, a magnetic field in which the direction of magnetic lines of force has an angle to the horizontal plane on the permanent magnet 19, the capsule endoscope 10 can be tilted with respect to the gravity direction Dg so that the magnetization direction Ym of the permanent magnet 19 becomes substantially parallel to the magnetic lines of force. Thus, in-vivo images around the capsule endoscope 10 can easily be acquired only by applying a rotating magnetic field rotating around the vertical axis while the capsule endoscope 10 is tilted to rotate the capsule endoscope 10 around the vertical axis.

Figure 6:
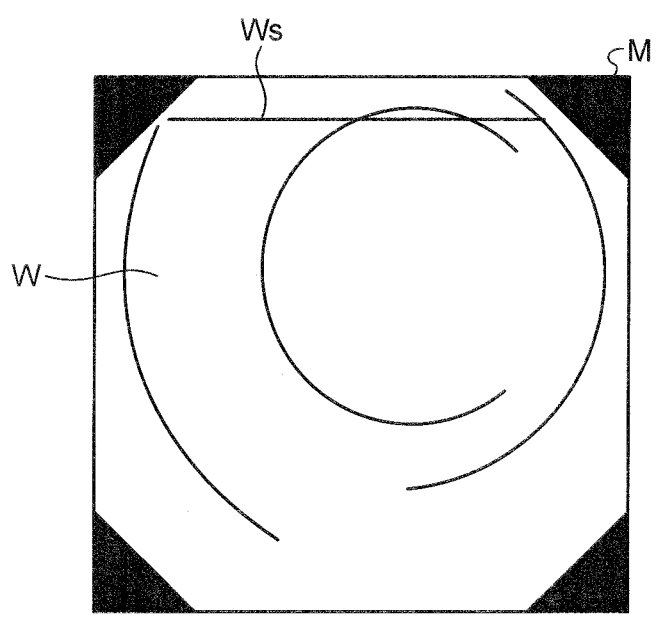
FIG. 6 is a diagram exemplifying an image displayed in a display screen of a display unit shown in FIG. 1.

The display unit 5 displays in-vivo images of a subject by the capsule endoscope 10 in a display mode in which the up/down direction of an object in in-vivo images attendant on magnetic guidance of the capsule endoscope 10 and the up/down direction of the display screen are matched. As illustrated in, for example, in FIG. 6, the display unit 5 displays in such a way that the liquid surface (upper boundary surface between the liquid and the outside, which applies similarly below) Ws captured by a device in an upper area Pu of the image pickup device 15A of the capsule endoscope 10 is in an upper part of an image M in the display screen. Since the magnetization direction Ym of the permanent magnet 19 is parallel to the up/down direction Yu of each imaging surface of the image pickup devices 15A, 15B, the direction parallel to the magnetization direction Ym of the permanent magnet 19 matches the up/down direction of the display screen of the display unit 5.

Figure 7:
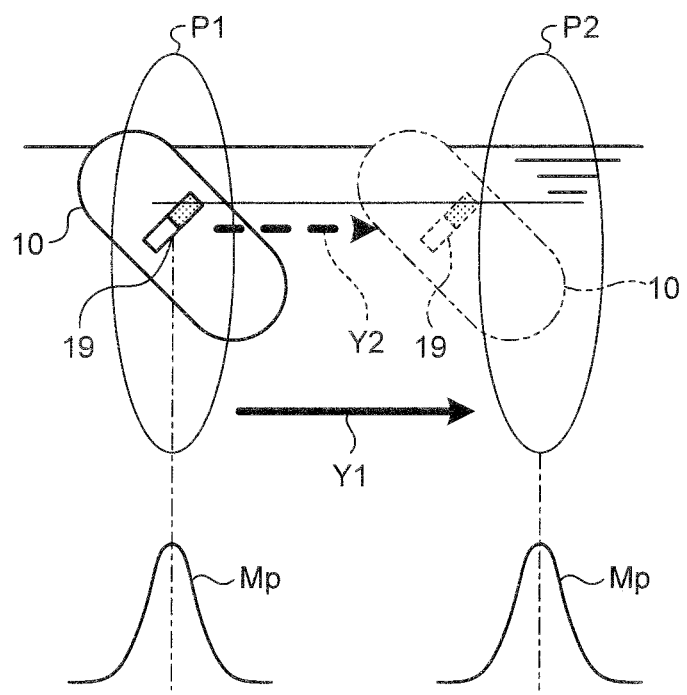
FIG. 7 is a diagram illustrating a peak magnetic field generated by a magnetic field generation unit shown in FIG. 1.

Next, types of magnetic field generated by the magnetic field generation unit 2 will be described. In addition to the so-called uniform magnetic field, the magnetic field generation unit 2 can generate a peak magnetic field and a uniform gradient magnetic field. A peak magnetic field is, as shown by a peak magnetic field Mp in FIG. 7, a magnetic field having a peak of magnetic field strength in a direction perpendicular to the horizontal plane. The peak magnetic field can attract the permanent magnet 19 to the peak position of the magnetic field strength to trap the capsule endoscope 10. That is, the peak magnetic field is a trapping magnetic field that attracts the permanent magnet 19 of the capsule endoscope 10 to any position in the horizontal direction to trap the capsule endoscope 10. The magnetic field generation unit 2 can move the capsule endoscope 10, like an arrow Y2, from a position P1 to a position P2 by moving the peak position of the peak magnetic field Mp, like an arrow Y1, from the position P1 to the position P2.

Figure 8:
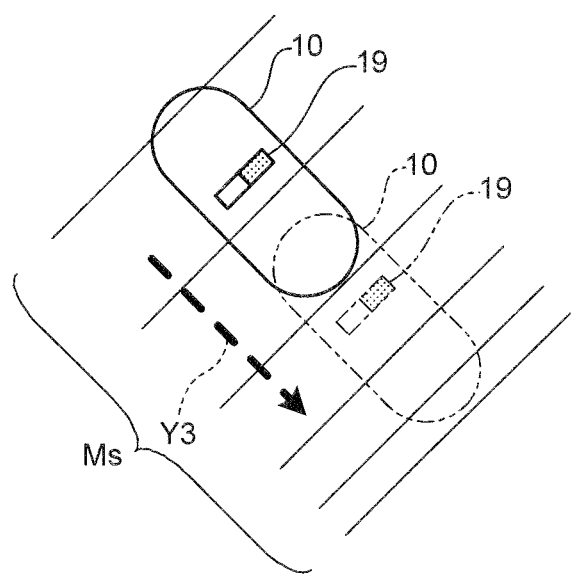
FIG. 8 is a diagram illustrating a uniform gradient magnetic field generated by a magnetic field generation unit shown in FIG. 1.

A uniform gradient magnetic field has, as shown by a uniform gradient magnetic field Ms in FIG. 8, a substantially uniform magnetic gradient. The uniform gradient magnetic field energizes the permanent magnet 19 in a direction in which the distribution of magnetic field strength changes from sparse to dense. The magnetic field generation unit 2 can move the capsule endoscope 10 in a direction indicated by an arrow Y3, for example, by generating the uniform gradient magnetic field Ms whose distribution of magnetic field strength changes from sparse to dense from obliquely the upper left to obliquely the lower right to energize the permanent magnet 19 in the direction indicated by the arrow Y3.

Figures 9, 10:
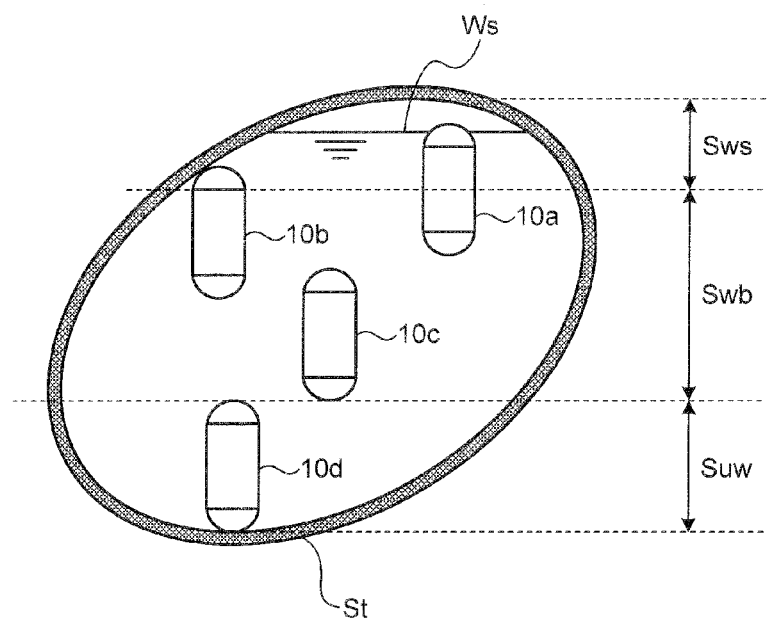
FIG. 9 is a diagram illustrating a state in which the capsule endoscope is positioned inside the stomach of the subject.
FIG. 10 is a diagram illustrating a table representing the type of magnetic field corresponding to each guidance area shown in FIG. 9.

In the first embodiment, the magnetic field the magnetic field generation unit 2 is caused to generate is switched depending on whether the capsule endoscope 10 is guided to the liquid surface, into the liquid, or to the liquid bottom (lower boundary surface between the liquid and the outside, which applies similarly below). First, guidance areas to which the capsule endoscope 10 is guided will be described with reference to FIG. 9 by taking a case when the capsule endoscope 10 is floated inside the stomach as an example. As shown in FIG. 9, a liquid surface area Sws in which a capsule endoscope 10a near the liquid surface is positioned, a submerged area Swb in which a capsule endoscope 10c floating in the liquid is positioned, and a liquid bottom area Suw in which a capsule endoscope 10d in contact with a lower surface of a stomach wall St are set as guidance areas. The liquid surface area Sws includes a case when, like a capsule endoscope 10b, in contact with an upper surface of the stomach wall St. The magnetic field to be generated is set for each guidance area of the liquid surface area Sws, the submerged area Swb, and the liquid bottom area Suw and magnetic field conditions corresponding to each guidance area are stored in the magnetic-field-condition storage unit 47.

If the input unit 6 inputs selection information that selects one of the liquid surface area Sws, the submerged area Swb, and the liquid bottom area Suw, the magnetic-field-condition switching unit 46 switches, based on the selection information, the magnetic field the magnetic field generation unit 2 is caused to generate to the magnetic field corresponding to the selected guidance area from among magnetic field conditions stored in the magnetic-field-condition storage unit 47. The magnetic-field-condition switching unit 46 switches at least one of the guidance direction of the capsule endoscope 10 by the magnetic field the magnetic field generation unit 2 is caused to generate, the type of the magnetic field the magnetic field generation unit 2 is caused to generate, and the magnitude and orientation of the magnetic gradient generated in the vertical direction of the magnetic field the magnetic field generation unit 2 is caused to generate in accordance with the selected guidance area selected by the input unit 6 from selection conditions. The magnetic-field-condition switching unit 46 switches the type of the magnetic field the magnetic field generation unit 2 is caused to generate between the peak magnetic field and the uniform gradient magnetic field in accordance with the selected guidance area selected by the input unit 6 from selection conditions. Then, the magnetic field control instruction unit 45 issues instructions to the magnetic field control unit 8 to cause the magnetic field generation unit 2 to generate the magnetic field in accordance with operation information to magnetically guide the capsule endoscope 10 from the input unit 6.

Next, the types of magnetic field corresponding to each guidance area will be described. FIG. 10 is a diagram illustrating Table T1 representing the types of magnetic field corresponding to each guidance area. As shown in Table T1 in FIG. 10, the types of magnetic field corresponding to, among guidance areas, the liquid surface area (including the case when the capsule endoscope 10 is in contact with the upper surface of the stomach wall) are the peak magnetic field and the vertical direction gradient magnetic field having a gradient in the vertical direction. In the liquid surface area, it is necessary to move the capsule endoscope 10 along the liquid surface. The peak magnetic field can trap the position in the horizontal direction to realize stable guidance on the liquid surface and thus is suitable when the capsule endoscope 10 is guided in the horizontal direction in the liquid surface area. While the uniform gradient magnetic field can generate a strong force, the magnetic field is distorted in a strict sense, which makes movement of the capsule endoscope 10 by the uniform gradient magnetic field unstable, so that the capsule endoscope 10 cannot be maintained in the position instructed for operation in a frictionless environment such as the liquid surface. Therefore, the uniform gradient magnetic field is set not to apply to the liquid surface area.

The types of magnetic field corresponding to the submerged area are the uniform gradient magnetic field and the uniform magnetic field. The peak magnetic field can trap the position of the capsule endoscope 10 in the horizontal direction, but cannot maintain the position of the capsule endoscope 10 in the vertical direction in the liquid. The guidance principle is different in the horizontal direction and the vertical direction and thus, it is difficult to generate a peak magnetic field that accurately combines movement of each control axis like the movement direction in the liquid described below. Therefore, instead of the peak magnetic field, the uniform gradient magnetic field and the uniform magnetic field are applied in the liquid to guide the capsule endoscope 10.

The types of magnetic field corresponding to the liquid bottom area are, like the submerged area, the uniform gradient magnetic field and the uniform magnetic field. At the liquid bottom, it is difficult to move the position of the capsule endoscope 10 in the horizontal direction along the surface of the stomach wall due to friction with the surface of the stomach wall or an influence of the shape of the surface of the stomach wall. Thus, the capsule endoscope 10 is set not to be guided in the horizontal direction in the liquid bottom area and accordingly, the peak magnetic field is excluded from the types of magnetic field corresponding to the liquid bottom area.

Thus, in the first embodiment, the types of magnetic field applied to the permanent magnet 19 are automatically switched for each guidance area so that guidance of the capsule endoscope 10 suitable for each guidance area can be realized. Also in the first embodiment, the operator only needs to select the desired guidance area without setting the type of magnetic field suitable among many conditions to fit to each guidance area and therefore, the capsule endoscope 10 can correctly be guided by a simple operation.

Figure 11:
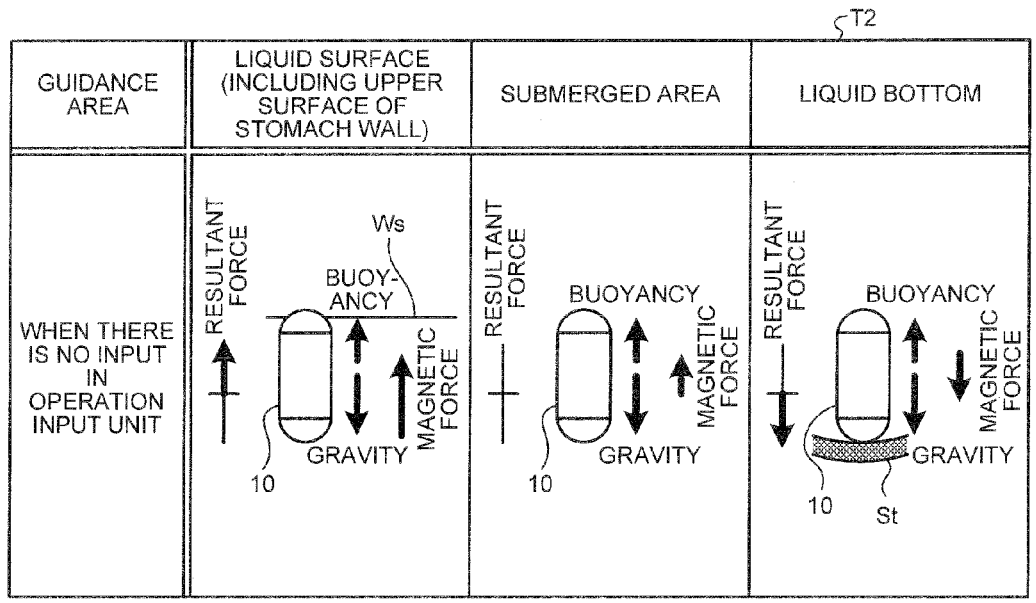
FIG. 11 is a diagram illustrating a table representing the magnetic field generated in each guidance area if there is no operation information for magnetic guidance in an operation input unit.

If the input unit 6 selects the guidance area, the magnetic field corresponding to each selected guidance area and described below is automatically generated by the magnetic field generation unit 2. FIG. 11 is a diagram illustrating Table T2 representing the magnetic field generated in each guidance area if there is no operation information for magnetic guidance in an operation input unit when the guidance area to guide the capsule endoscope 10 is selected.

If the liquid surface area is selected as the guidance area, the magnetic field generation unit 2 generates a vertical direction gradient magnetic field having a gradient in the vertical direction in an area where a peak magnetic field is generated under control of the magnetic field control instruction unit 45 and the magnetic field control unit 8 and, as shown in Table T2 in FIG. 11, an upward magnetic gradient with respect to the vertical axis is generated with strength so that the direction of a resultant force of the buoyancy, the gravity of the capsule endoscope 10, and the magnetic attraction caused by the magnetic gradient is directed upward with respect to the vertical axis. That is, the magnetic field generation unit 2 generates a magnetic field that traps (thrusts) the capsule endoscope 10 on the liquid surface Ws or on the upper surface of the stomach wall. As a result, the capsule endoscope 10 is positioned on the liquid surface Ws or on the upper surface of the stomach wall.

If the submerged area is selected as the guidance area, the magnetic field generation unit 2 generates a uniform gradient magnetic field in the vertical direction under control of the magnetic field control instruction unit 45 and the magnetic field control unit 8 and, as shown in Table T2 in FIG. 11, an upward magnetic gradient with respect to the vertical axis is generated so that the gravity of the capsule endoscope 10, the buoyancy, and the magnetic attraction in the vertical direction are approximately balanced. That is, the magnetic field generation unit 2 generates a magnetic force in the capsule endoscope 10 to cause the capsule endoscope 10 to float in the liquid. As a result, the capsule endoscope 10 will be positioned in the liquid.

If the liquid bottom area is selected as the guidance area, the magnetic field generation unit 2 generates a uniform gradient magnetic field in the vertical direction under control of the magnetic field control instruction unit 45 and the magnetic field control unit 8 and, as shown in Table T2 in FIG. 11, a downward magnetic gradient with respect to the vertical axis is generated with strength so that the direction of a resultant force of the buoyancy, the gravity of the capsule endoscope 10, and the magnetic attraction is directed downward with respect to the vertical axis. That is, the magnetic field generation unit 2 generates a magnetic field that traps (thrusts) the capsule endoscope 10 on the surface of the stomach wall at the liquid bottom. As a result, the capsule endoscope 10 is positioned at the liquid bottom.

Thus, by applying the magnetic field of the strength and direction associated with each guidance area to the permanent magnet 19, the capsule endoscope 10 can automatically be positioned correctly in the selected guidance area even if no operation information to magnetically guide the capsule endoscope 10 is input through the input unit 6. Therefore, operation input processing to maintain the capsule endoscope 10 for each guidance area by the operator is not needed so that operability is improved.

Figure 12A:
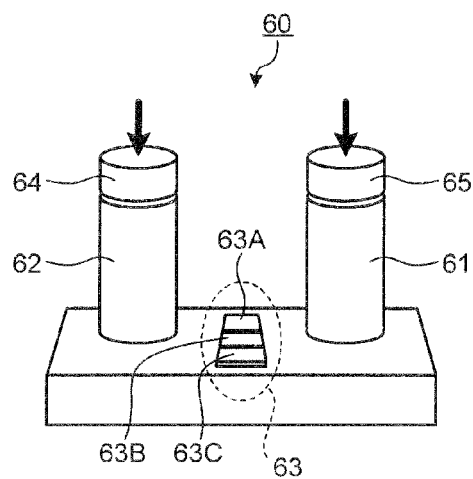
FIG. 12A is a front view of the operation input unit constituting an input unit shown in FIG. 1.
Figure 12B:
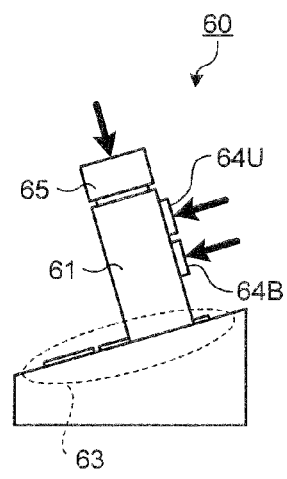
FIG. 12B is a right side view of the operation input unit shown in FIG. 12A.

Next, what kind of magnetic field is applied to the permanent magnet 19 and how the capsule endoscope 10 is moved by the operation of the operation input unit will be described. First, the operation input unit to operate magnetic guidance of the capsule endoscope 10 will be described. FIGS. 12A and 12B are schematic views exemplifying the operation input unit constituting the input unit 6 shown in FIG. 1. FIG. 12A is a front view of the operation input unit and FIG. 12B is a right side view of the operation input unit.

As shown in FIG. 12A, an operation input unit 60 includes two joysticks 61, 62 to three-dimensionally operate magnetic guidance of the capsule endoscope 10 by the magnetic field generation unit 2. The joysticks 61, 62 can be operated to tilt forward/backward and left/right.

The operation input unit 60 also includes a guidance area switching unit 63 having a liquid surface switch 63A, a submersion switch 63B, and a liquid bottom switch 63C. If the liquid surface switch 63A is pressed, the liquid surface switch 63A inputs selection information to select the liquid surface area as the guidance area into the external control unit 4. If the submersion switch 63B is pressed, the submersion switch 63B inputs selection information to select the submerged area as the guidance area into the external control unit 4. If the liquid bottom switch 63C is pressed, the liquid bottom switch 63C inputs selection information to select the liquid bottom area as the guidance area into the external control unit 4.

As shown in FIG. 12B, the joystick 61 includes an up button 64U and a down button 64B on the rear side. If the up button 64U is pressed, the up button 64U inputs operation information to instruct upward guidance of the capsule endoscope 10 into the external control unit 4. If the down button 64B is pressed, the down button 64B inputs operation information to instruct downward guidance of the capsule endoscope 10 into the external control unit 4. The joystick 62 includes an approach button 64 in an upper part thereof. If the approach button 64 is pressed, the approach button 64 inputs operation information to guide the capsule endoscope 10 so that the imaging unit 11A side of the capsule endoscope 10 approaches an imaging target of the imaging unit 11A into the external control unit 4. The joystick 61 includes a capture button 65 in an upper part thereof. If the capture button 65 is pressed, the capture button 65 captures an in-vivo image displayed in the display unit 5.

Figure 13A:
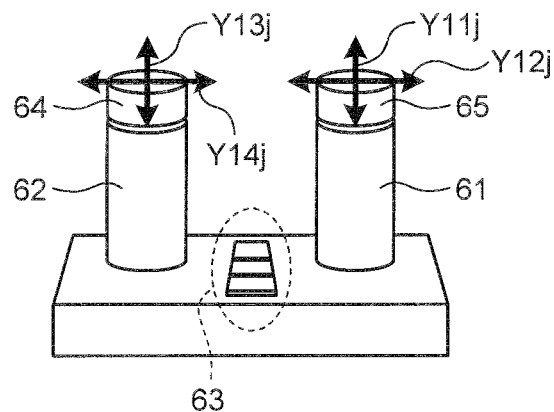
FIG. 13A is a front view of the operation input unit illustrating the magnetic guidance of a capsule medical device operable by the operation input unit in a liquid surface area.
Figure 13B:
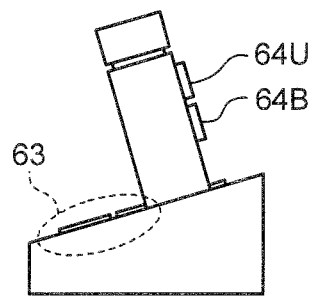
FIG. 13B is a right side view of the operation input unit illustrating the magnetic guidance of the capsule medical device operable by the operation input unit in the liquid surface area.
Figure 13C:
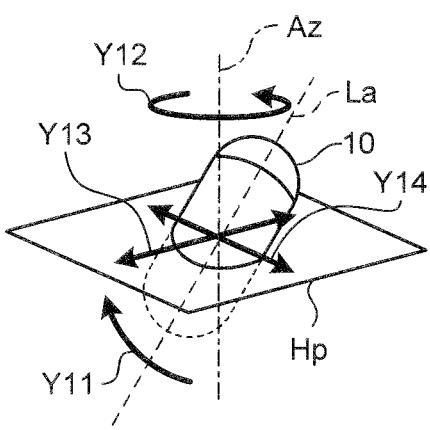
FIG. 13C is a diagram showing operation content of the capsule endoscope instructed by an operation of each element of the operation input unit.

Next, each operation of each element by the operator of the operation input unit 60 and the magnetic field generated by the magnetic field generation unit 2 corresponding to each operation will be described. First, a case when the liquid surface area is selected will be described. FIGS. 13A to 13C are diagrams illustrating magnetic guidance in the liquid surface area of a capsule medical device that can be operated by the operation input unit 60, FIG. 13A is a front view of the operation input unit 60, FIG. 13B is a right side view of the operation input unit 60, and FIG. 13C is a diagram showing operation content of the capsule endoscope 10 instructed by an operation of each element of the operation input unit 60.

First, as shown in FIG. 13A, the forward/backward tilting direction of the joystick 61 indicated by an arrow Y11$j$ corresponds to a tilting operation direction in which the tip of the capsule endoscope 10 oscillates, like an arrow Y11 in FIG. 13C, by passing through a vertical axis Az. If the operation input unit 60 inputs operation information corresponding to the tilting operation of the arrow Y11$j$ of the joystick 61 into the external control unit 4, the magnetic field control instruction unit 45 calculates the guidance direction of the tip of the capsule endoscope 10 corresponding to the tilting direction of the joystick 61 on absolute coordinates based on the operation information and calculates the guidance speed corresponding to the tilting operation of the joystick 61. Then, the magnetic field control instruction unit 45 selects the peak magnetic field switched by the magnetic-field-condition switching unit 46 as an applied magnetic field and causes the magnetic field generation unit 2 to generate a peak magnetic field in the orientation corresponding to the calculated guidance direction and also changes the angle formed between the orientation of the peak magnetic field and the vertical axis Az at the calculated guidance speed in a vertical plane containing the vertical axis Az and the long axis La of the capsule endoscope 10.

As shown in FIG. 13A, the left/right tilting direction of the joystick 61 indicated by an arrow Y12$j$ corresponds to a rotation operation direction in which the capsule endoscope 10 rotates, like an arrow Y12 in FIG. 13C, around the vertical axis Az. If the operation input unit 60 inputs operation information corresponding to the tilting operation of the arrow Y12$j$ of the joystick 61 into the external control unit 4, the magnetic field control instruction unit 45 calculates the guidance direction of the tip of the capsule endoscope 10 corresponding to the tilting direction of the joystick 61 on absolute coordinates based on the operation information and calculates the guidance speed corresponding to the tilting operation of the joystick 61 to cause the magnetic field generation unit 2 to generate a peak magnetic field in the orientation corresponding to the calculated guidance direction and also to rotate the orientation of the peak magnetic field at the calculated guidance speed around the vertical axis Az.

As shown in FIG. 13A, the forward/backward tilting direction of the joystick 62 indicated by an arrow Y13$j$ corresponds to a horizontal backward operation direction or horizontal forward operation direction that travels, like an arrow Y13 in FIG. 13C, in the direction in which the long axis La of the capsule endoscope 10 is projected on a horizontal plane Hp. If the operation input unit 60 inputs operation information corresponding to the tilting operation of the arrow Y13$j$ of the joystick 62 into the external control unit 4, the magnetic field control instruction unit 45 calculates the guidance direction and guidance position of the tip of the capsule endoscope 10 corresponding to the tilting direction of the joystick 62 on absolute coordinates based on the operation information and calculates the guidance speed corresponding to the tilting operation of the joystick 62 to cause the magnetic field generation unit 2 to generate a peak magnetic field in the orientation corresponding to the calculated guidance direction and also to move the peak of the peak magnetic field to the guidance position at the calculated guidance speed.

As shown in FIG. 13A, the left/right tilting direction of the joystick 62 indicated by an arrow Y14$j$ corresponds to a horizontal right operation direction or horizontal left operation direction that travels, like an arrow Y14 in FIG. 13C, in a direction perpendicular to the direction in which the long axis La of the capsule endoscope 10 is projected on the horizontal plane Hp. If the operation input unit 60 inputs operation information corresponding to the tilting operation of the arrow Y14$j$ of the joystick 62 into the external control unit 4, the magnetic field control instruction unit 45 calculates the guidance direction and guidance position of the tip of the capsule endoscope 10 corresponding to the tilting direction of the joystick 62 on absolute coordinates based on the operation information and calculates the guidance speed corresponding to the tilting operation of the joystick 62 to cause the magnetic field generation unit 2 to generate a peak magnetic field in the orientation corresponding to the calculated guidance direction and also to move the peak of the peak magnetic field to the guidance position at the calculated guidance speed.

Thus, if the liquid surface area is selected as the guidance area, guidance operations to guide the capsule endoscope 10 in accordance with each operation of the operation input unit 60 are set so that the capsule endoscope 10 can be guided along the liquid surface. Incidentally, the capsule endoscope 10 cannot be guided further upward in the liquid surface area and thus, the up button 64U is disabled.

Figure 14A:
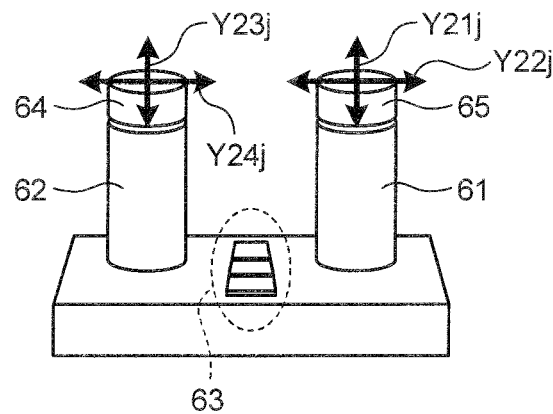
FIG. 14A is a front view of the operation input unit illustrating the magnetic guidance of the capsule medical device operable by the operation input unit in a submerged area.
Figure 14B:
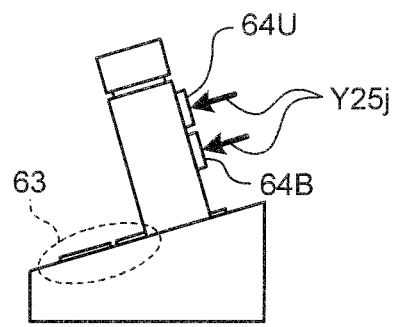
FIG. 14B is a right side view of the operation input unit illustrating the magnetic guidance of the capsule medical device operable by the operation input unit in the submerged area.
Figure 14C:
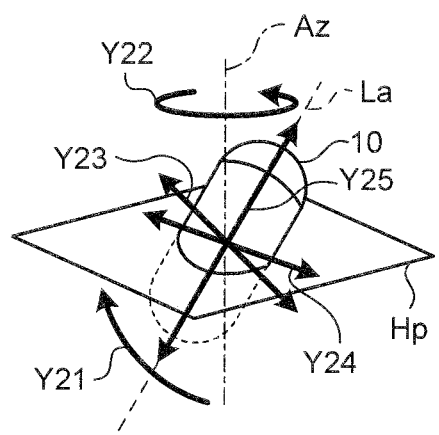
FIG. 14C is a diagram showing the operation content of the capsule endoscope instructed by the operation of each element of the operation input unit.

Next, a case when the submerged area is selected will be described. FIGS. 14A to 14C are diagrams illustrating magnetic guidance in the submerged area of a capsule medical device that can be operated by the operation input unit 60, FIG. 14A is a front view of the operation input unit 60, FIG. 14B is a right side view of the operation input unit 60, and FIG. 14C is a diagram showing operation content of the capsule endoscope 10 instructed by an operation of each element of the operation input unit 60.

First, as shown in FIG. 14A, the forward/backward tilting direction of the joystick 61 indicated by an arrow Y21$j$ corresponds to a tilting operation direction of the capsule endoscope 10 indicated by an arrow Y21 in FIG. 14C. If the operation input unit 60 inputs operation information corresponding to the tilting operation of the arrow Y21$j$ of the joystick 61 into the external control unit 4, the magnetic field control instruction unit 45 calculates the guidance direction of the tip of the capsule endoscope 10 corresponding to the tilting direction of the joystick 61 on absolute coordinates based on the operation information and calculates the guidance speed corresponding to the tilting operation of the joystick 61. Then, the magnetic field control instruction unit 45 selects the uniform gradient magnetic field and uniform magnetic field switched by the magnetic-field-condition switching unit 46 as applied magnetic fields and causes the magnetic field generation unit 2 to generate a uniform magnetic field in the orientation corresponding to the calculated guidance direction and also changes the angle formed by the orientation of the uniform magnetic field, the vertical axis Az, and the long axis La of the capsule endoscope 10 at the calculated guidance speed in the vertical plane containing the vertical axis Az.

As shown in FIG. 14A, the left/right tilting direction of the joystick 61 indicated by an arrow Y22$j$ corresponds to a rotation guidance direction of the capsule endoscope 10 indicated by an arrow Y22 in FIG. 14C. If the operation input unit 60 inputs operation information corresponding to the tilting operation of the arrow Y22$j$ of the joystick 61 into the external control unit 4, the magnetic field control instruction unit 45 calculates the guidance direction of the tip of the capsule endoscope 10 corresponding to the tilting direction of the joystick 61 on absolute coordinates based on the operation information and calculates the guidance speed corresponding to the tilting operation of the joystick 61 to cause the magnetic field generation unit 2 to generate a uniform magnetic field in the orientation corresponding to the calculated guidance direction and also to rotate the orientation of the uniform magnetic field around the vertical axis Az at the calculated guidance speed.

As shown in FIG. 14A, the forward/backward tilting direction of the joystick 62 indicated by an arrow Y23$j$ corresponds to a down operation direction or up operation direction that travels like an arrow Y23 in a vertical plane containing the long axis La of the capsule endoscope 10 shown in FIG. 14C. If the operation input unit 60 inputs operation information corresponding to the tilting operation of the arrow Y23$j$ of the joystick 62 into the external control unit 4, the magnetic field control instruction unit 45 calculates the operation direction of the tip of the capsule endoscope 10 corresponding to the tilting direction of the joystick 62 on absolute coordinates based on the operation information and calculates the operation speed corresponding to the tilting operation of the joystick 62 to cause the magnetic field generation unit 2 to generate a uniform gradient magnetic field having a gradient of the orientation corresponding to the calculated operation direction and corresponding to the calculated operation speed.

As shown in FIG. 14A, the left/right tilting direction of the joystick 62 indicated by an arrow Y24j corresponds to a right operation direction or left operation direction that travels like an arrow Y24 in a vertical plane containing the long axis La of the capsule endoscope 10 shown in FIG. 14C. If the operation input unit 60 inputs operation information corresponding to the tilting operation of the arrow Y24j of the joystick 62 into the external control unit 4, the magnetic field control instruction unit 45 calculates the operation direction of the tip of the capsule endoscope 10 corresponding to the tilting direction of the joystick 62 on absolute coordinates based on the operation information and calculates the operation speed corresponding to the tilting operation of the joystick 61 to cause the magnetic field generation unit 2 to generate a uniform gradient magnetic field having a gradient of the orientation corresponding to the calculated operation direction and corresponding to the calculated operation speed.

Further, as shown in FIG. 14B, if the up button 64U or the down button 64B is pressed like an arrow Y25j, the up button 64U or the down button 64B instructs the image pickup devices 15A, 15B to move in a forward operation direction or backward operation direction like an arrow Y25 along the long axis La of the capsule endoscope 10 shown in FIG. 14C. If the operation input unit 60 inputs operation information corresponding to the pressing operation of the arrow Y25j of the up button 64U or the down button 64B into the external control unit 4, the magnetic field control instruction unit 45 calculates the operation direction of the tip of the capsule endoscope 10 corresponding to the pressed button on absolute coordinates based on the operation information and causes the magnetic field generation unit 2 to generate a uniform gradient magnetic field having a gradient along the long axis La corresponding to the calculated operation direction.

Figure 15:
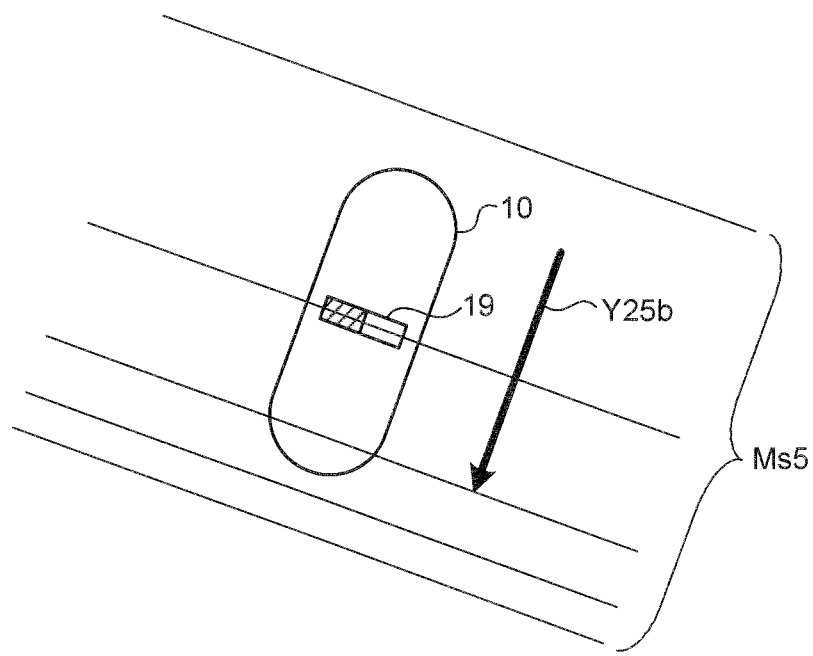
FIG. 15 is a diagram exemplifying the uniform gradient magnetic field generated by the magnetic field generation unit shown in FIG. 1.
Figure 16:
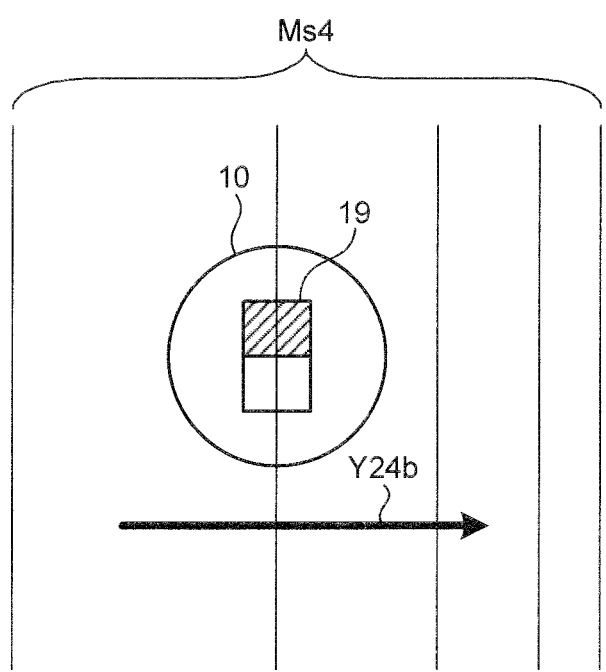
FIG. 16 is a diagram exemplifying the uniform gradient magnetic field generated by the magnetic field generation unit shown in FIG. 1.

More specifically, if the down button 64B is pressed, as shown in FIG. 15, the magnetic field generation unit 2 generates a uniform gradient magnetic field Ms5 that is denser in the down direction from the long axis La direction of the capsule endoscope 10 to move the capsule endoscope 10, like an arrow Y25b, in the down direction from the long axis La direction of the capsule endoscope 10. If the joystick 62 is operated to input a right operation, as shown in FIG. 16, the magnetic field generation unit 2 generates a uniform gradient magnetic field Ms4 denser in the right direction from a magnetic field parallel to the magnetization direction of the permanent magnet 19 when a plane orthogonal to the long axis La of the capsule endoscope 10 is viewed from below to move the capsule endoscope 10, like an arrow Y24b, in the right direction of the plane orthogonal to the long axis La of the capsule endoscope 10. If the joystick 62 is operated to input an up operation, as shown in FIG. 17, the magnetic field generation unit 2 generates a uniform gradient magnetic field Ms3 denser in the upward direction from a magnetic field parallel to the magnetization direction of the permanent magnet 19 when a plane orthogonal to the long axis La of the capsule endoscope 10 is viewed from below to move the capsule endoscope 10, like an arrow Y23u, in the upward direction of the plane orthogonal to the long axis La of the capsule endoscope 10.

Thus, if the submerged area is selected as the guidance area, each operation of the operation input unit 60 and the guidance operation of the capsule endoscope 10 are associated and set so that the capsule endoscope 10 can be guided along the plane orthogonal to the long axis of the capsule endoscope 10, instead of the horizontal plane. That is, the guidance operations are set so that the capsule endoscope 10 can be guided along the imaging surface of the imaging units 11A, 11B. In other words, the capsule endoscope 10 is guided to move up and down, left and right with respect to an image. Thus, the operator can guide the capsule endoscope 10 as if the operator were making an observation inside the stomach with his (her) eyes and thus, more intuitive guidance is enabled. If the submerged area is selected as the guidance area, the capsule endoscope 10 can be guided upward/downward along the long axis La of the capsule endoscope 10 in the liquid and thus, an observation can be made while moving toward or away from an observation target.

Figure 18A:
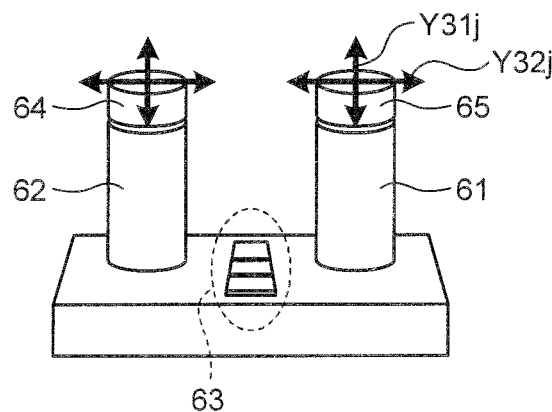
FIG. 18A is a front view of the operation input unit illustrating the magnetic guidance of the capsule medical device operable by the operation input unit in a liquid bottom area.
Figure 18B:
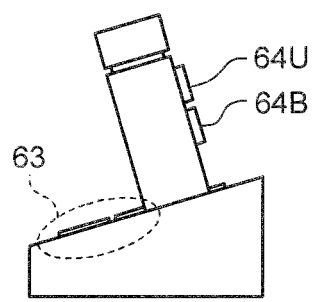
FIG. 18B is a right side view of the operation input unit illustrating the magnetic guidance of the capsule medical device operable by the operation input unit in the liquid bottom area.
Figure 18C:
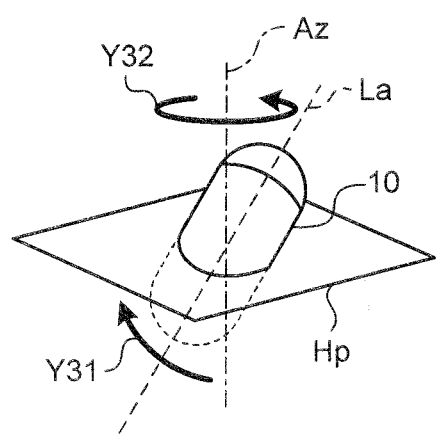
FIG. 18C is a diagram showing the operation content of the capsule endoscope instructed by the operation of each element of the operation input unit.

Next, a case when the liquid bottom area is selected will be described. FIGS. 18A to 18C are diagrams illustrating magnetic guidance in the liquid bottom area of a capsule medical device that can be operated by the operation input unit 60, FIG. 18A is a front view of the operation input unit 60, FIG. 18B is a right side view of the operation input unit 60, and FIG. 18C is a diagram showing operation content of the capsule endoscope 10 instructed by an operation of each element of the operation input unit 60.

First, as shown in FIG. 18A, the forward/backward tilting direction of the joystick 61 indicated by an arrow Y31j corresponds to a tilting operation direction of the capsule endoscope 10 indicated by an arrow Y31 in FIG. 18C. If the operation input unit 60 inputs operation information corresponding to the tilting operation of the arrow Y31j of the joystick 61 into the external control unit 4, the magnetic field control instruction unit 45 calculates the guidance direction of the tip of the capsule endoscope 10 corresponding to the tilting direction of the joystick 61 on absolute coordinates based on the operation information and calculates the guidance speed corresponding to the tilting operation of the joystick 61. Then, the magnetic field control instruction unit 45 selects the uniform gradient magnetic field and uniform magnetic field switched by the magnetic-field-condition switching unit 46 as applied magnetic fields and causes the magnetic field generation unit 2 to generate a uniform magnetic field in the orientation corresponding to the calculated guidance direction and also changes the angle formed by the orientation of the uniform magnetic field, the vertical axis Az, and the long axis La of the capsule endoscope 10 at the calculated guidance speed in the vertical plane containing the vertical axis Az.

As shown in FIG. 18A, the left/right tilting direction of the joystick 61 indicated by an arrow Y32j corresponds to a rotation guidance direction of the capsule endoscope 10 indicated by an arrow Y32 in FIG. 18C. If the operation input unit 60 inputs operation information corresponding to the tilting operation of the arrow Y32j of the joystick 61 into the external control unit 4, the magnetic field control instruction unit 45 calculates the guidance direction of the tip of the capsule endoscope 10 corresponding to the tilting direction of the joystick 61 on absolute coordinates based on the operation information and calculates the guidance speed corresponding to the tilting operation of the joystick 61 to cause the magnetic field generation unit 2 to generate a uniform magnetic field in the orientation corresponding to the calculated guidance direction and also to rotate the orientation of the uniform magnetic field at the calculated guidance speed around the vertical axis Az.

Thus, if the liquid bottom area is selected as the guidance area, the tilting operation and rotation operation are set to be able to make a minute observation of the liquid bottom, that is, the stomach wall St. The up operation and backward operation to move the capsule endoscope 10 away from the surface of the stomach wall are not set for the liquid surface area so that the surface of the stomach wall can minutely be observed. It is often difficult to move the capsule endoscope 10 along the surface of the stomach wall due to friction with the surface of the stomach wall or the shape of the surface of the stomach wall and thus, the forward operation, right operation, and left operation are not set either. Further, the capsule endoscope 10 cannot be guided still downward and thus, the down operation is not set either. Therefore, the joystick 62, the up button 64U, and the down button 64B are disabled.

In the first embodiment, as described above, the capsule endoscope 10 can be guided in a manner appropriate for each guidance area by changing the relationship between the operation input unit 60 and the moving direction of the capsule endoscope 10 matching each guidance area. That is, in the first embodiment, the capsule endoscope 10 can be guided in a manner appropriate for each guidance area by switching the type of magnetic field, the guidance direction of the capsule endoscope 10, and the magnitude and orientation of the magnetic gradient generated in the vertical direction matching each guidance area.

Next, guidance processing of the capsule endoscope 10 of the capsule medical device guidance system 1 will be described. FIG. 19 is a flow chart showing a processing procedure for guidance processing of the capsule endoscope 10 of the capsule medical device guidance system 1 shown in FIG. 1.

When, as shown in FIG. 19, the input unit 6 inputs instruction information to instruct the start of an in-vivo observation, the magnetic field control instruction unit 45 transmits instruction information to the magnetic field control unit 8 to cause the magnetic field generation unit 2 to generate a magnetic field under initial conditions (step S2). For example, the magnetic field control instruction unit 45 causes the magnetic field generation unit 2 to generate a peak magnetic field having a peak in the center of a magnetic field generated area as an initial condition. In this case, the start position of guidance processing of the capsule endoscope 10 is easy to understand so that operability when the guidance operation is started is improved. When a predetermined button in the input unit 6 is pressed, the magnetic field control instruction unit 45 may cause the magnetic field generation unit 2 to generate a peak magnetic field having a peak in the center of a magnetic field generated area under this initial condition. Even if the capsule endoscope 10 deviates from trapping of a peak magnetic field and guidance fails, the capsule endoscope 10 can easily be restored to the position under initial conditions and thus, operability is improved.

Then, the image receiving unit 41 performs image receiving processing to successively acquire in-vivo images successively received by the transmitting/receiving unit 3 (step S4) and the image display control unit 42 performs image display processing to cause the display unit 5 to display in-vivo images successively received by the transmitting/receiving unit 3 (step S6).

In the external control unit 4, the magnetic-field-condition switching unit 46 determines whether there is any setting instruction of the guidance area based on whether there is any input of selection information from the operation input unit 60 (step S8). If the magnetic-field-condition switching unit 46 determines that there is a setting instruction of the guidance area (step S8: Yes), the magnetic-field-condition switching unit 46 switches magnetic field generation conditions by the magnetic field generation unit 2 in accordance with the guidance area selected by the operation input unit 60 based on the input selection information (step S10). The magnetic-field-condition storage unit 47 stores, as described above, magnetic field generation conditions in which the type of magnetic field, the guidance direction of the capsule endoscope 10, and the magnitude and orientation of the magnetic gradient generated in the vertical direction are set for each guidance area and the magnetic-field-condition switching unit 46 refers to magnetic field generation conditions corresponding to the set guidance area among magnetic field generation conditions stored in the magnetic-field-condition storage unit 47 to switch to the referred magnetic field generation conditions. This case corresponds to a case when no operation information is input from the operation input unit 60 and thus, the magnetic field control instruction unit 45 causes the magnetic field generation unit 2 to generate a magnetic field having a magnetic force shown in Table T2 in FIG. 11. Thus, the capsule endoscope 10 is positioned in the set guidance area with stability. When the guidance area is switched to another guidance area, the capsule endoscope 10 is guided into the new switched guidance area to be positioned in the guidance area with stability.

On the other hand, if the magnetic-field-condition switching unit 46 determines that there is no setting instruction of the guidance area (step S8: No) or the magnetic-field-condition switching unit 46 switches magnetic field generation conditions (step S10), the magnetic field control instruction unit 45 determines whether there is any movement instruction of the capsule endoscope 10 based on whether there is any input of operation information from the operation input unit 60 (step S12). If the magnetic field control instruction unit 45 determines that there is a movement instruction of the capsule endoscope 10 (step S12: Yes), the magnetic field control instruction unit 45 calculates the movement position instructed by the operation information from the operation input unit 60 (step S14) and acquires conditions for the magnetic field applied to the permanent magnet 19 of the capsule endoscope 10 based on magnetic field generation conditions corresponding to the guidance area (step S16). Then, the magnetic field control instruction unit 45 issues instructions to the magnetic field control unit 8 to generate a magnetic field under the acquired magnetic field conditions and the magnetic field generation unit 2 performs magnetic field generation processing to generate a magnetic field under the instructed conditions (step S18). As a result, the capsule endoscope 10 moves in the direction and to the position following the operation processing by the operation input unit 60.

If the magnetic field control instruction unit 45 determines that there is no movement instruction of the capsule endoscope 10 (step S12: No) or the magnetic field generation processing is completed (step S18), the image receiving unit 41 performs image receiving processing (step S20) and the image display control unit 42 performs image display processing (step S22). As a result, the display unit 5 successively displays in-vivo images captured by the capsule endoscope 10. Incidentally, there may be a delay time of several hundred msec between the acquisition of an image of the capsule endoscope 10 by the transmitting/receiving unit 3 and the display of the image by the display unit 5. In such a case, if the guidance speed of the capsule endoscope 10 is too fast, the position operation of the capsule endoscope 10 diverges with respect to the target position, leading to degradation in operability. Thus, it is desirable to guide the capsule endoscope 10 at a guidance speed corresponding to the delay time. For example, it is desirable to guide the capsule endoscope 10 at the speed of 10 mm/sec or less.

Subsequently, the external control unit 4 determines whether the in-vivo observation has completed based on the instruction information input by the input unit 6 (step S24). If the external control unit 4 determines that the in-vivo observation has not completed (step S24: No), the external control unit 4 returns to step S8 to continue the in-vivo observation and determines whether there is any setting instruction of the guidance area. If the external control unit 4 determines that the in-vivo observation has completed (step S24: Yes), the external control unit 4 puts a group of in-vivo images captured by the capsule endoscope 10 together in one folder and stores the folder in the storage unit 7 before terminating the in-vivo observation.

Thus, according to the first embodiment, magnetic field generation conditions are automatically switched for each guidance area and a magnetic field is generated under conditions appropriate for each guidance area and thus, the capsule endoscope 10 can correctly be guided by a simple operation.

The first embodiment is described by taking a case when the liquid surface area, submerged area, and liquid bottom area are set as the guidance areas as an example, but the first embodiment is not limited to this example and any combination of at least two of the liquid surface area, submerged area, and liquid bottom area may be adopted. For example, the guidance area may be limited to the liquid surface area and the liquid bottom area. In the submerged area, the position of the capsule endoscope 10 may not be maintained accurately in a desired position due to an influence of distortion of a uniform magnetic field and if the distortion of the uniform gradient magnetic field is large, controllability may be degraded depending on the magnetic field generation unit. In such a case, the capsule endoscope 10 can be guided only in stable areas by limiting the guidance area to the liquid surface area and the liquid bottom area so that operability is improved.

In the submerged area, the backward operation, forward operation, right operation, or left operation is described as an operation in a vertical plane containing the long axis La of the capsule endoscope 10 shown in FIG. 14C, but the first embodiment is not limited to this. The backward operation, forward operation, right operation, or left operation in the submerged area may be set, like the horizontal backward operation, horizontal forward operation, horizontal right operation, or horizontal left operation in the liquid surface area, as a movement operation in the horizontal plane Hp.

Figure 20A:
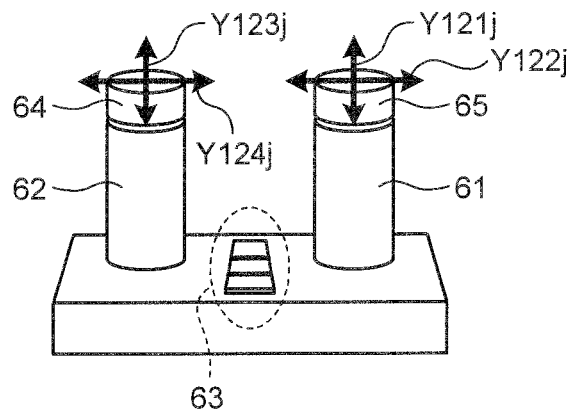
FIG. 20A is a front view of the operation input unit illustrating another example of the magnetic guidance of the capsule medical device operable by the operation input unit in the submerged area.

More specifically, if, as shown in FIG. 20A, the operation input unit 60 inputs operation information corresponding to the tilting operation of an arrow Y123j of the joystick 62 into the external control unit 4, the magnetic field control instruction unit 45 causes the magnetic field generation unit 2 to generate a uniform magnetic field or a uniform gradient magnetic field based on the operation information so that the capsule endoscope 10 moves like an arrow Y123 (see FIG. 20C) in the horizontal plane Hp. If, as shown in FIG. 20A, the operation input unit 60 inputs operation information corresponding to the tilting operation of an arrow Y124j of the joystick 62 into the external control unit 4, the magnetic field control instruction unit 45 causes the magnetic field generation unit 2 to generate a uniform magnetic field or a uniform gradient magnetic field based on the operation information so that the capsule endoscope 10 moves like an arrow Y124 (see FIG. 20C) in the horizontal plane Hp.

Figure 20B:
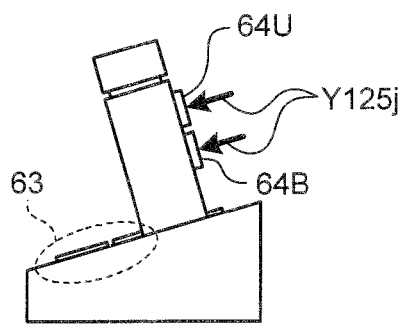
FIG. 20B is a right side view of the operation input unit illustrating the other example of the magnetic guidance of the capsule medical device operable by the operation input unit in the submerged area.
Figure 20C:
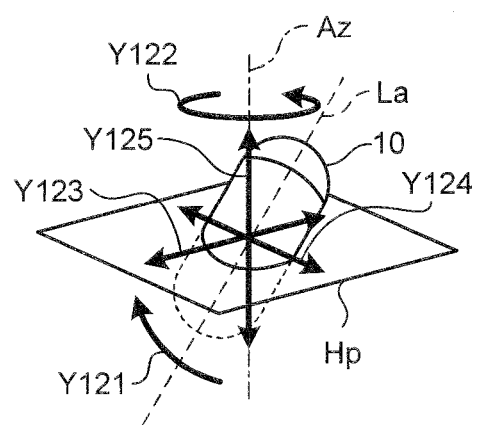
FIG. 20C is a diagram showing the operation content of the capsule endoscope instructed by the operation of each element of the operation input unit.

In the submerged area, the up operation or the down operation may be set as a movement operation that moves upward/downward along the vertical axis Az. In this case, if, as shown in FIG. 20B, the operation input unit 60 inputs operation information corresponding to the pressing operation of an arrow Y125j of the up button 64U or the down button 64B into the external control unit 4, the magnetic field control instruction unit 45 causes the magnetic field generation unit 2 to generate a uniform gradient magnetic field based on the operation information so that the capsule endoscope 10 moves like an arrow Y125 (see FIG. 20C) on the vertical axis Az. If, as indicated by an arrow Y121 or an arrow Y122 in FIG. 20C, the operation input unit 60 inputs operation information corresponding to the tilting operation of an arrow Y121j or operation information corresponding to the tilting operation of an arrow Y122j of the joystick 61 into the external control unit 4, the magnetic field control instruction unit 45 causes the magnetic field generation unit 2 to generate a uniform magnetic field whose direction is changed so that the capsule endoscope 10 performs a tilting operation or rotation operation like an operation indicated by an arrow Y121 or arrow Y122 in FIG. 14C.

Thus, if the guidance operations of the capsule endoscope 10 are set in such a way that there is little difference in moving direction of the capsule endoscope 10 between the submerged area and the liquid surface area, the guidance of the capsule endoscope 10 can be continued without confusion when the guidance area is switched. In this case, the capsule endoscope 10 can be guided by using only a peak magnetic field by assuming that the capsule endoscope 10 is not guided in the submerged area because the submerged area is not set as a guidance area.

In the liquid bottom area, an example in which neither the right operation nor the left operation to move the capsule endoscope 10 in the horizontal plane is set is described, but the first embodiment is not limited to this and the position of the capsule endoscope 10 can be changed in the horizontal plane depending on conditions. Thus, settings may be made so that the forward operation, backward operation, right operation, or left operation that changes the capsule endoscope 10 can be performed in the horizontal plane in the liquid bottom area.

Figure 21A:
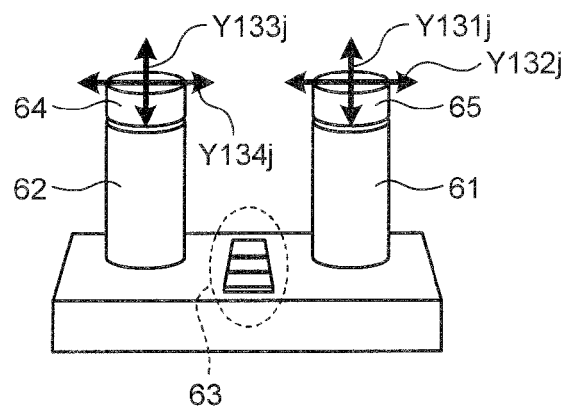
FIG. 21A is a front view illustrating the magnetic guidance of the capsule medical device operable by the operation input unit in the liquid bottom area.
Figure 21B:
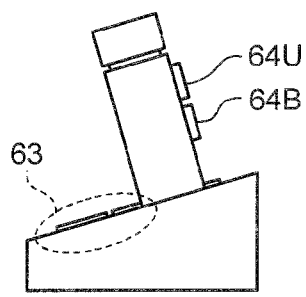
FIG. 21B is a right side view illustrating the magnetic guidance of the capsule medical device operable by the operation input unit in the liquid bottom area.

More specifically, if, as shown in FIG. 21A, the operation input unit 60 inputs operation information corresponding to the tilting operation of an arrow Y133j of the joystick 62 into the external control unit 4, the magnetic field control instruction unit 45 causes the magnetic field generation unit 2 to generate a uniform magnetic field or a uniform gradient magnetic field based on the operation information so that the capsule endoscope 10 moves like an arrow Y133 (see FIG. 21C) in the horizontal plane Hp. If, as shown in FIG. 21A, the operation input unit 60 inputs operation information corresponding to the tilting operation of an arrow Y134j of the joystick 62 into the external control unit 4, the magnetic field control instruction unit 45 causes the magnetic field generation unit 2 to generate a uniform magnetic field or a uniform gradient magnetic field based on the operation information so that the capsule endoscope 10 moves like an arrow Y134 (see FIG. 21C) in the horizontal plane Hp. Incidentally, FIG. 21B shows a right side view of the operation input unit.

Figure 21C:
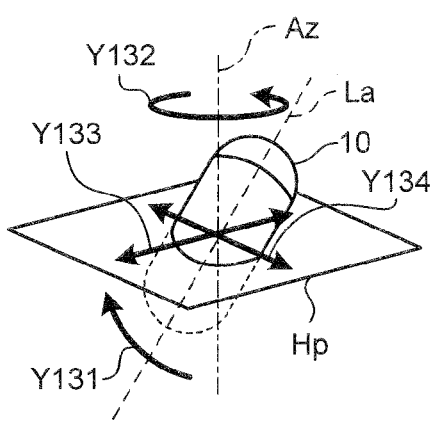
FIG. 21C is a diagram showing the operation content of the capsule endoscope instructed by the operation of each element of the operation input unit.

If, as indicated by an arrow Y131 or an arrow Y132 in FIG. 21C, the operation input unit 60 inputs operation information corresponding to the tilting operation of an arrow Y131j or operation information corresponding to the tilting operation of an arrow Y132j of the joystick 61 into the external control unit 4, the magnetic field control instruction unit 45 causes the magnetic field generation unit 2 to generate a uniform magnetic field whose direction is changed so that the capsule endoscope 10 performs a tilting operation or rotation operation like an operation indicated by an arrow Y131 or arrow Y132 in FIG. 21C. For the forward operation, backward operation, right operation, and left operation that moved the capsule endoscope 10 in the horizontal plane, it is desirable to generate a uniform gradient magnetic field that can be generated in great strength because it is necessary to move the capsule endoscope 10 against a friction on the surface of the stomach wall.

In the first embodiment, when the capsule endoscope 10 is moved from the liquid surface area to the submerged area or the liquid bottom area, the capsule endoscope 10 is smoothly moved from the liquid surface area to the submerged area or the liquid bottom area by generating a strong magnetic field of strength capable of resisting surface tension of the liquid surface. The mode to generate a strong magnetic field of strength capable of resisting surface tension of the liquid surface will be described as a diving mode.

Figure 22:
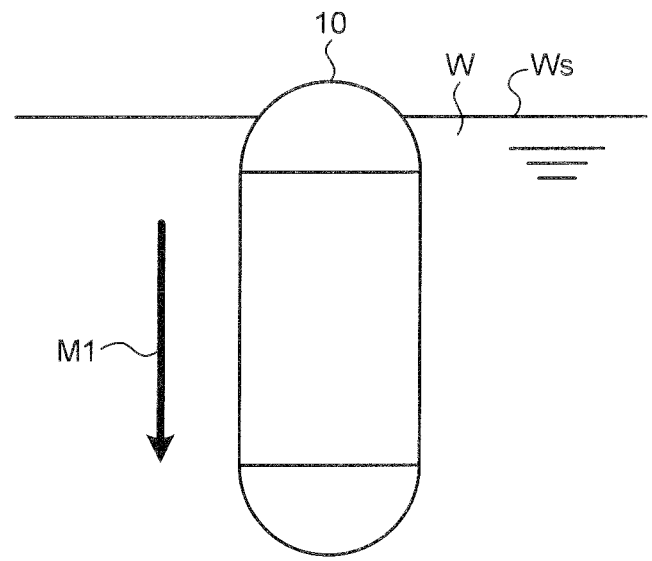
FIG. 22 is a diagram illustrating a diving mode, which is an example of the magnetic guidance.
Figure 23:
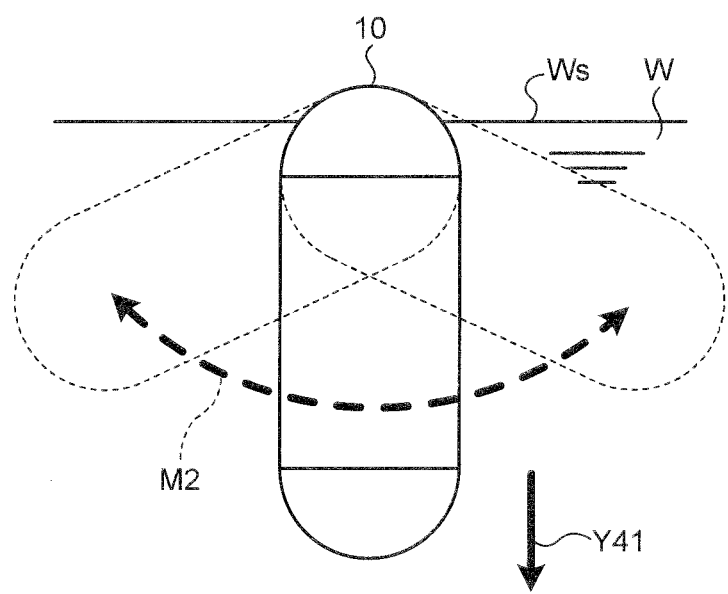
FIG. 23 is a diagram illustrating the diving mode, which is an example of the magnetic guidance.

In diving mode, a strong magnetic field is temporarily generated downward in the vertical direction by control of the magnetic field generation unit 2 by the external control unit 4 to move the capsule endoscope 10, like an arrow M1 in FIG. 22, from the liquid surface into the liquid or to the liquid bottom. The posture of the capsule endoscope 10 may be changed fast by generating a magnetic field M2 causing the capsule endoscope 10 to perform, as shown in FIG. 23, a fast tilting operation by control of the magnetic field generation unit 2 by the external control unit 4. In this case, a liquid is splashed on the side wall of the capsule endoscope 10 exposed from the liquid surface by the tilting operation, neutralizing the influence of surface tension. Then, the capsule endoscope 10 is moved from the liquid surface into the liquid or to the liquid bottom by generating a magnetic field that moves, as indicated by an arrow Y41, the capsule endoscope 10 downward by control of the magnetic field generation unit 2 by the external control unit 4. When this method is used, even if the magnetic field is weak, the capsule endoscope 10 can be guided from the liquid surface into the liquid or to the liquid bottom.

The diving mode is automatically generated when the guidance area is switched from the liquid surface area to the submerged area or the liquid bottom area. A selection button to select an ON state or OFF state of the diving mode may be provided to enable an operator to control the ON state of the diving mode by operating the selection button. If the diving mode is in the ON state, when operation instructions downward in the vertical direction are first issued, the magnetic field generation unit 2 only once generates a magnetic field to resist the surface tension under control of the external control unit 4 and then, the diving mode is automatically turned off. Thus, if the diving mode is in the ON state, even if the capsule endoscope 10 moves to the liquid surface while the capsule endoscope 10 being guided in the liquid, the guidance in the liquid can easily be restored.

In the first embodiment, an approach mode to cause the imaging unit 11A of the capsule endoscope 10 to approach an imaging target is also provided. The approach mode is a function to guide the imaging unit 11A of the capsule endoscope 10 in the long axis La direction of the capsule endoscope 10, that is, in the imaging direction of images by using a uniform gradient magnetic field.

Figure 24:
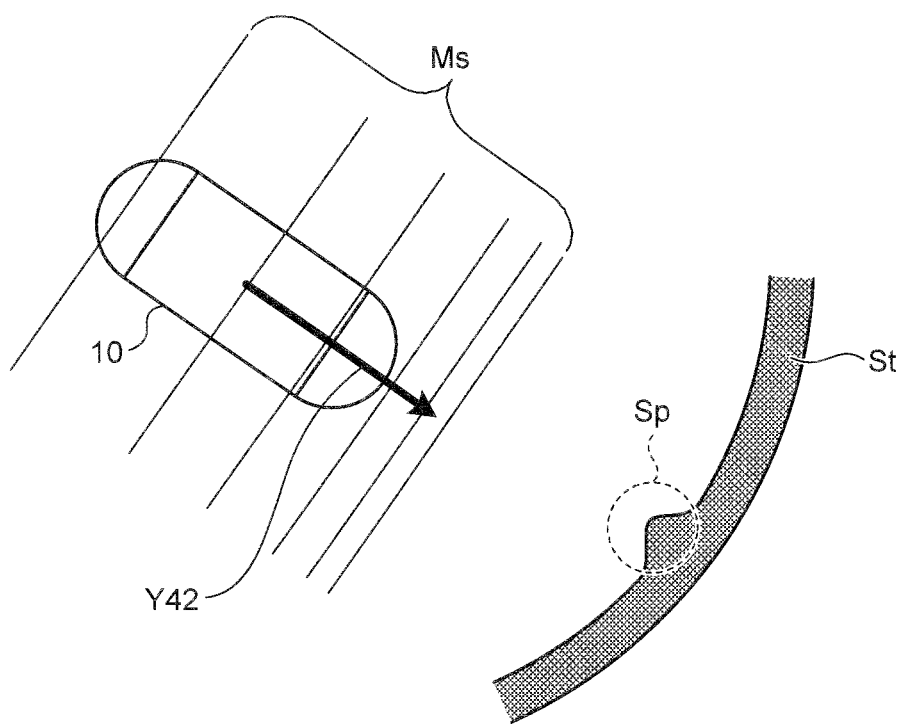
FIG. 24 is a diagram illustrating an approach mode, which is an example of the magnetic guidance.

The approach mode is in the ON state while the approach button 64 of the operation input unit 60 illustrated in FIGS. 12A and 12B is pressed and in the OFF state if a pressing force on the approach button 64 is released. A case when, as shown in, for example, FIG. 24, the approach mode is turned on while the capsule endoscope 10 in a downward posture captures an image of an imaging target portion Sp at the liquid bottom will be described.

While the approach mode is in the ON state, the magnetic field control instruction unit 45 causes the magnetic field generation unit 2 to generate the uniform gradient magnetic field Ms having a gradient downward along the long axis La of the capsule endoscope 10. As a result, as indicated by an arrow Y42, the capsule endoscope 10 can be caused to approach the imaging target portion Sp of the stomach wall St currently being imaged by the imaging unit 11A. Naturally, if the capsule endoscope 10 capturing the upper stomach wall St in an upward posture should be caused to approach the stomach wall St, the magnetic field generation unit 2 may be caused to generate the uniform gradient magnetic field Ms having a gradient upward along the long axis La of the capsule endoscope 10. The imaging direction of the capsule endoscope 10 may be set based on the imaging direction of the reference imaging unit of the imaging units 11A, 11B.

Operation steps executed by an operator will be described. The operator grasps the area from among the liquid surface area, submerged area, and liquid bottom area in which the capsule endoscope 10 is present based on an image acquired by the capsule endoscope 10 and displayed by the display unit 5. Next, the operator checks whether the currently set guidance area and the area in which the capsule endoscope 10 is present match. If both areas do not match, the operator operates the input unit 6 to match the guidance area to the area in which the capsule endoscope 10 is present before starting the guidance operation. If the currently set guidance area and the area in which the capsule endoscope 10 is present match, the guidance operation can be performed as it is.

To change the area in which the capsule endoscope 10 is guided, the operator operates the input unit 6 to change the guidance area to the area into which the capsule endoscope 10 should be guided, whereby the capsule endoscope 10 moves to the next guidance area. However, if the guidance area should be changed from the liquid surface area to the submerged area, it is necessary to operate the joystick of the input unit 6 to guide the capsule endoscope 10 from the liquid surface area to the submerged area.

By executing the above operation steps, the capsule endoscope 10 can be guided under more stable conditions while changing the setting of the guidance area.

Second Embodiment

Next, a second embodiment will be described. In the second embodiment, a case when the area in which the capsule endoscope is present is automatically detected from an image of the capsule endoscope and the capsule endoscope 10 is automatically guided in the set guidance area.

Figure 25:
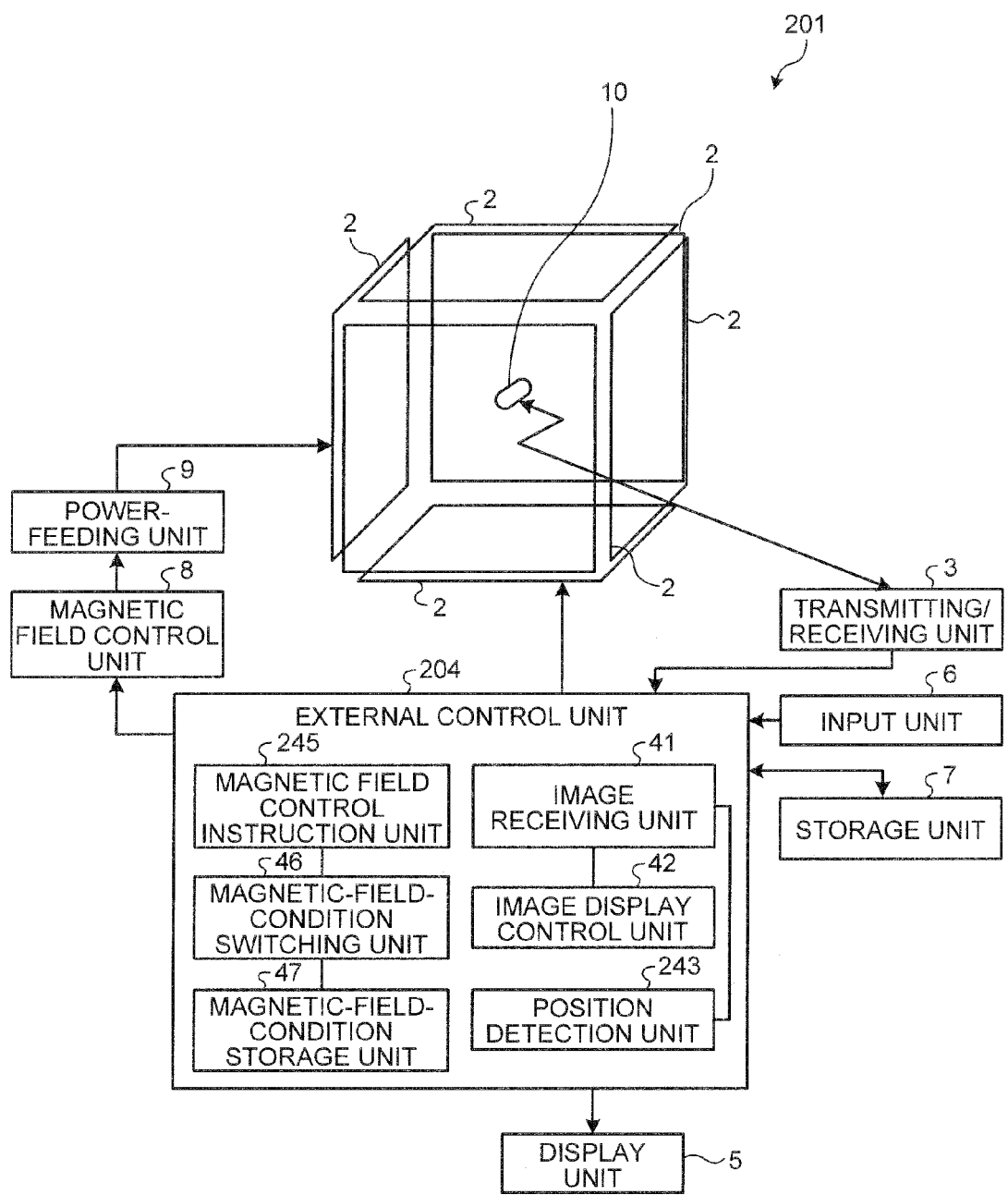
FIG. 25 is a schematic view showing the overall configuration of a capsule medical device guidance system according to a second embodiment.

FIG. 25 is a schematic view showing the overall configuration of a capsule medical device guidance system according to the second embodiment. As shown in FIG. 25, a capsule medical device guidance system 201 according to the second embodiment includes, instead of the external control unit 4 shown in FIG. 1, an external control unit 204. When compared with the external control unit 4, the external control unit 204 further includes a position detection unit 243 and, instead of the magnetic field control instruction unit 45, a magnetic field control instruction unit 245.

The position detection unit 243 detects the area in which the capsule endoscope 10 is present from the liquid surface area, submerged area, and liquid bottom area based on an image captured by the capsule endoscope 10. If the area in which the capsule endoscope 10 is present detected by the position detection unit 243 and the guidance area selected by the operation input unit 60 of the input unit 6 do not match, the magnetic field control instruction unit 245 causes the magnetic field generation unit 2 to generate a magnetic field that guides the capsule endoscope 10 into the guidance area selected by the operation input unit 60.

Figure 26:
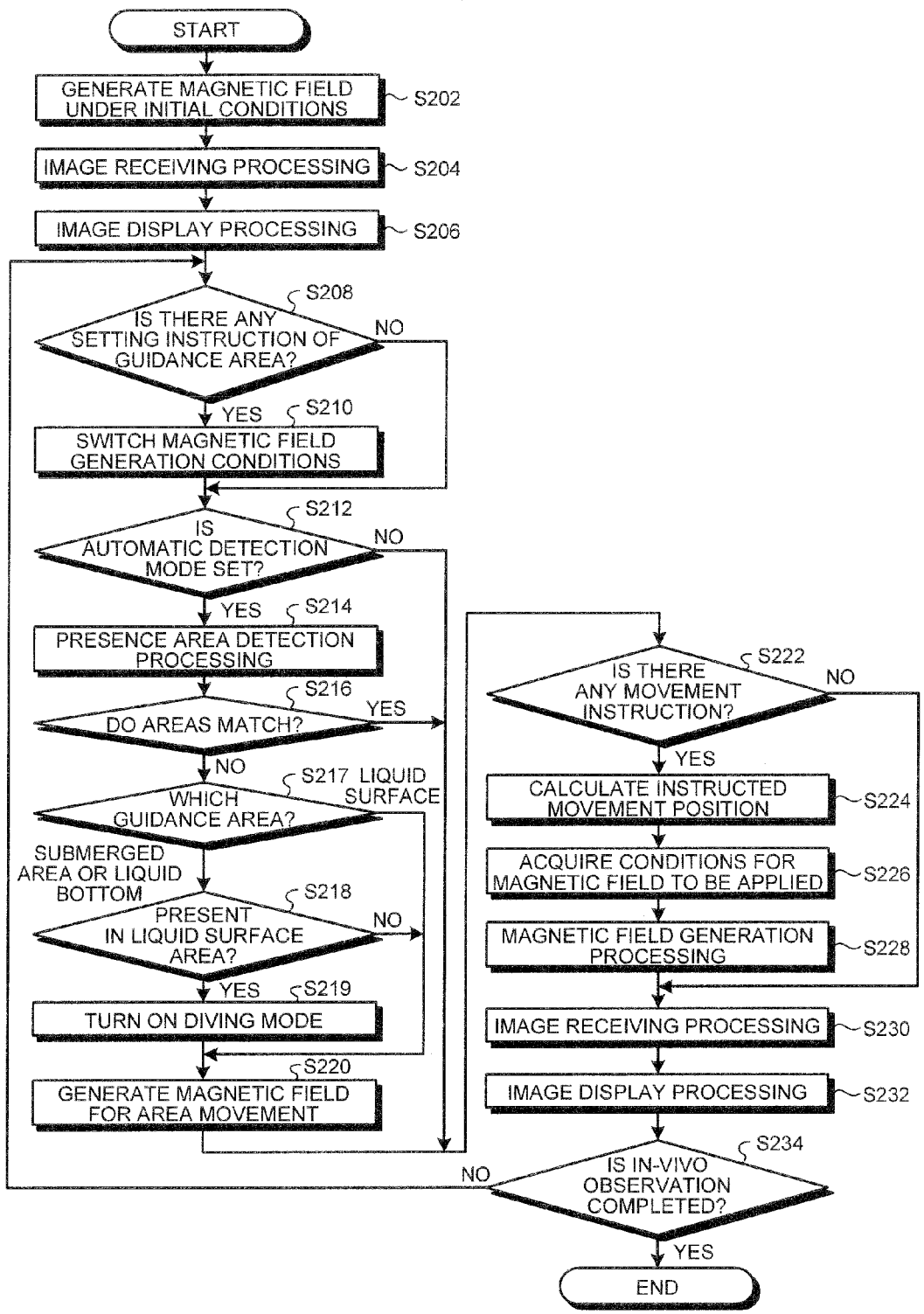
FIG. 26 is a flow chart showing the processing procedure for guidance processing of the capsule endoscope of the capsule medical device guidance system shown in FIG. 25.

Next, guidance processing of the capsule endoscope 10 of the capsule medical device guidance system 201 shown in FIG. 25 will be described with reference to FIG. 26. FIG. 26 is a flow chart showing the processing procedure for guidance processing of the capsule endoscope 10 of the capsule medical device guidance system 201 shown in FIG. 25.

As shown in FIG. 26, if, like step S2 shown in FIG. 19, the input unit 6 inputs instruction information to instruct the start of an in-vivo observation, the magnetic field control instruction unit 245 transmits instruction information to the magnetic field control unit 8 to cause the magnetic field generation unit 2 to generate a magnetic field under initial conditions (step S202). Next, like step S4 and step S6 in FIG. 19, the image receiving unit 41 performs image receiving processing (step S204) and the image display control unit 42 performs image display processing (step S206).

In the external control unit 204, like step S8 in FIG. 19, the magnetic-field-condition switching unit 46 determines whether there is any setting instruction of the guidance area (step S208). If the magnetic-field-condition switching unit 46 determines that there is a setting instruction of the guidance area (step S208: Yes), the magnetic-field-condition switching unit 46 switches magnetic field generation conditions by the magnetic field generation unit 2 in accordance with the guidance area selected by the operation input unit 60 based on the input selection information (step S210).

Next, if the magnetic-field-condition switching unit 46 determines that there is no setting instruction of the guidance area (step S208: No) or after magnetic field generation conditions switching processing in step S210, the external control unit 204 determines whether the automatic detection mode to automatically detect the presence area of the capsule endoscope 10 is set (step S212). If the external control unit 204 determines that the automatic detection mode to automatically detect the presence area of the capsule endoscope 10 is set (step S212: Yes), the position detection unit 243 performs presence area detection processing to detect the presence are of the capsule endoscope 10 (step S214).

The position detection unit 243 detects the presence area of the capsule endoscope 10 based on whether there is any image pattern specific to the liquid surface area or liquid bottom area from an image captured by the capsule endoscope 10 received by the image receiving unit 41.

Figure 27:
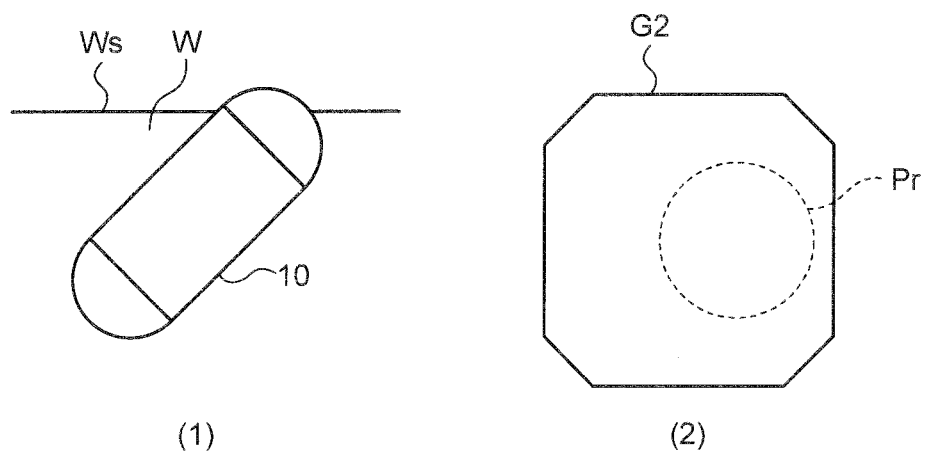
FIG. 27 is a diagram illustrating detection processing by a position detection unit shown in FIG. 25.

First, a case when the capsule endoscope 10 is positioned in the liquid surface area will be described with reference to FIG. 27. If, as shown in FIG. 27(1), the capsule endoscope 10 is present in the liquid surface area, the tip of the capsule endoscope 10 is exposed from the liquid surface Ws. The imaging field of view of the imaging units 11A, 11B spreads from the tip of the capsule endoscope 10. Thus, if, as shown in FIG. 27(1), the tip of the capsule endoscope 10 is exposed from the liquid surface Ws, like an image G2 in FIG. 27(2), a ring-shaped boundary Pr with the liquid surface Ws is displayed due to a rise of the liquid on the side of the capsule endoscope 10 caused by surface tension and reflection of illumination light from illumination units 13A, 13B. Thus, the position detection unit 243 determines whether there is any ring-shaped image pattern in images captured by the capsule endoscope 10 and if there is a ring-shaped image pattern, the position detection unit 243 determines that the capsule endoscope 10 is present in the liquid surface area.

Figure 28:
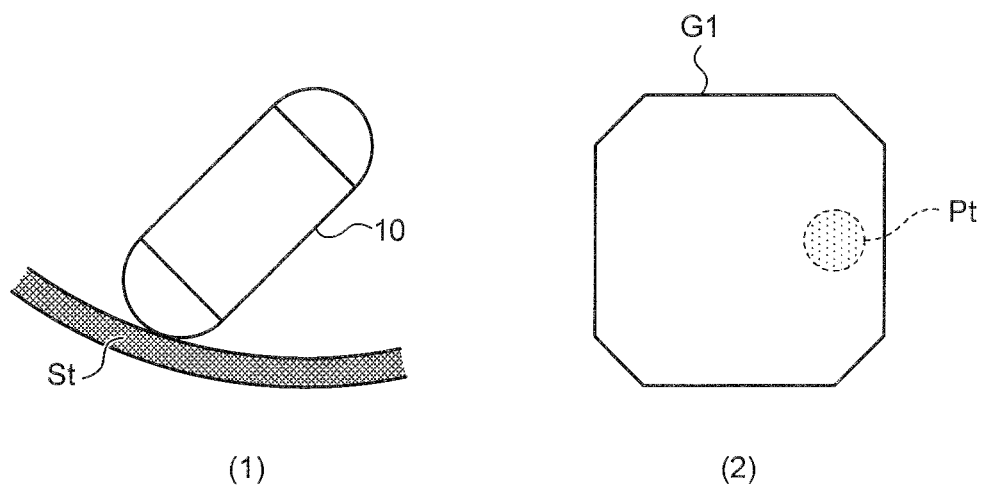
FIG. 28 is a diagram illustrating the detection processing by the position detection unit shown in FIG. 25.

Next, a case when the capsule endoscope 10 is positioned in the liquid bottom area will be described with reference to FIG. 28. If, as shown in FIG. 28(1), the capsule endoscope 10 is present in the liquid bottom area, the tip of the capsule endoscope 10 is pressed against the stomach wall St. Thus, in the case of FIG. 28(1), like an image G1 in FIG. 28(2), a contact portion Pt of the stomach wall St and the tip of the capsule endoscope 10 is displayed like a circle. Thus, the position detection unit 243 determines whether there is any circular image pattern in images captured by the capsule endoscope 10 and if there is a circular image pattern, the position detection unit 243 determines that the capsule endoscope 10 is present in the liquid bottom area.

If the position detection unit 243 determines that there is neither a ring-shaped image pattern nor a circular image pattern in images captured by the capsule endoscope 10, the position detection unit 243 determines that the capsule endoscope 10 is present in the submerged area.

Then, based on a detection result by the position detection unit 243, the magnetic field control instruction unit 245 determines whether the presence area of the capsule endoscope 10 and the guidance area selected by the operation input unit 60 match (step S216).

If the magnetic field control instruction unit 245 determines that the presence area of the capsule endoscope 10 and the guidance area selected by the operation input unit 60 do not match (step S216: No), the magnetic field control instruction unit 245 determines the guidance area whose setting is instructed (step S217). If the magnetic field control instruction unit 245 determines that the guidance area whose setting is instructed is the submerged area or the liquid bottom area (step S217: Submerged area or liquid bottom), the magnetic field control instruction unit 245 determines whether the capsule endoscope 10 is actually present in the liquid surface area based on the detection result in step S214 (step S218). If the magnetic field control instruction unit 245 determines that the capsule endoscope 10 is actually present in the liquid surface area (step S218: Yes), the magnetic field control instruction unit 245 turns on the diving mode (step S219).

Next, if the magnetic field control instruction unit 245 determines that the guidance area whose setting is instructed is the liquid surface area (step S217: Liquid surface), if the magnetic field control instruction unit 245 determines that the capsule endoscope 10 is not actually present in the liquid surface area (step S218: No), or if the diving mode-ON setting in step S219 is terminated, the magnetic field control instruction unit 245 issues instructions to the magnetic field control unit 8 to generate a magnetic field to guide the capsule endoscope 10 into the selected guidance area. As a result, the magnetic field generation unit 2 generates a magnetic field to move the capsule endoscope 10 into the selected guidance area (step S220). As the magnetic field to be generated, the magnetic field control instruction unit 245 causes the magnetic field generation unit 2 to generate a magnetic field having a magnetic force listed in Table T2 in FIG. 11. Further, if the presence area of the capsule endoscope 10 is the liquid surface area, and the submerged area or the liquid bottom area is set as the guidance area, as described above, the diving mode is turned on and thus, the magnetic field control instruction unit 245 once causes the magnetic field generation unit 2 to generate a magnetic field strong enough to resist the surface tension of the liquid and then a magnetic field having a magnetic force listed in Table T2 according to conditions in Table T1 for movement downward from the liquid surface in the vertical direction. In this case, the diving mode is automatically turned on without the need for the operator to turn on the diving mode, further improving operability. As a result, the capsule endoscope 10 moves into the set guidance area and is positioned in the guidance area with stability.

If the external control unit 204 determines that the automatic detection mode to automatically detect the presence area of the capsule endoscope 10 is not set (step S212: No), if the magnetic field control instruction unit 245 determines that the presence area of the capsule endoscope 10 and the guidance area selected by the operation input unit 60 match (step S216: Yes), or if magnetic field generation processing in step S220 is completed, like step S12 in FIG. 19, the magnetic field control instruction unit 245 determines whether there is any movement instruction of the capsule endoscope 10 (step S222).

If the magnetic field control instruction unit 245 determines that there is a movement instruction of the capsule endoscope 10 (step S222: Yes), like in the first embodiment, the magnetic field control instruction unit 245 calculates the movement position instructed by the operation information from the operation input unit 60 (step S224) and acquires conditions for the magnetic field applied to the permanent magnet 19 of the capsule endoscope 10 based on magnetic field generation conditions corresponding to the guidance area (step S226). Then, the magnetic field control instruction unit 245 issues instructions to the magnetic field control unit 8 to generate a magnetic field under the acquired magnetic field conditions and the magnetic field generation unit 2 performs magnetic field generation processing to generate a magnetic field under the instructed conditions (step S228). As a result, the capsule endoscope 10 moves in the direction and to the position following the operation processing by the operation input unit 60. If there is a movement component downward in the vertical direction and the diving mode is in the ON state, the magnetic field control instruction unit 245 issues instructions to the magnetic field control unit 8 to cause the magnetic field generation unit 2 to generate a magnetic field that resists the surface tension.

If the magnetic field control instruction unit 245 determines that there is no movement instruction of the capsule endoscope 10 (step S222: No) or the magnetic field generation processing is completed (step S228), the image receiving unit 41 performs image receiving processing (step S230) and the image display control unit 42 performs image display processing (step S232). As a result, the display unit 5 successively displays in-vivo images captured by the capsule endoscope 10. Subsequently, the external control unit 204 determines whether the in-vivo observation has completed based on the instruction information input by the input unit 6 (step S234). If the external control unit 204 determines that the in-vivo observation has not completed (step S234: No), the external control unit 204 returns to step S208 to continue the in-vivo observation and determines whether there is any setting instruction of the guidance area. If the external control unit 204 determines that the in-vivo observation has completed (step S234: Yes), the external control unit 204 terminates the in-vivo observation.

Thus, in the second embodiment, the area in which the capsule endoscope 10 is present is automatically detected from images of the capsule endoscope 10 and if the detected presence area of the capsule endoscope 10 and the set guidance area do not match, a magnetic field to guide the capsule endoscope 10 into the set guidance area is automatically generated. Therefore, according to the present embodiment, there is no need for the operator to perform an operation to guide the capsule endoscope 10 into the desired guidance area based on an image displayed in the display unit 5, which enables, when compared with the first embodiment, correct guidance of the capsule endoscope 10 by a still simpler operation.

If the combination of guidance areas is only the liquid surface area and the liquid bottom area, the position detection unit 243 may determine only whether there is any ring-shaped image pattern in images captured by the capsule endoscope 10 without determining whether there is any circular image pattern. In this case, if the position detection unit 243 determines that there is a ring-shaped image pattern in images captured by the capsule endoscope 10, the position detection unit 243 determines that the presence area of the capsule endoscope 10 is the liquid surface area. If the position detection unit 243 determines that there is no ring-shaped image pattern in images captured by the capsule endoscope 10, the position detection unit 243 determines that the presence area of the capsule endoscope 10 is the liquid bottom area. In this case, detection processing of the presence area of the capsule endoscope 10 can further be simplified.

Figure 29:
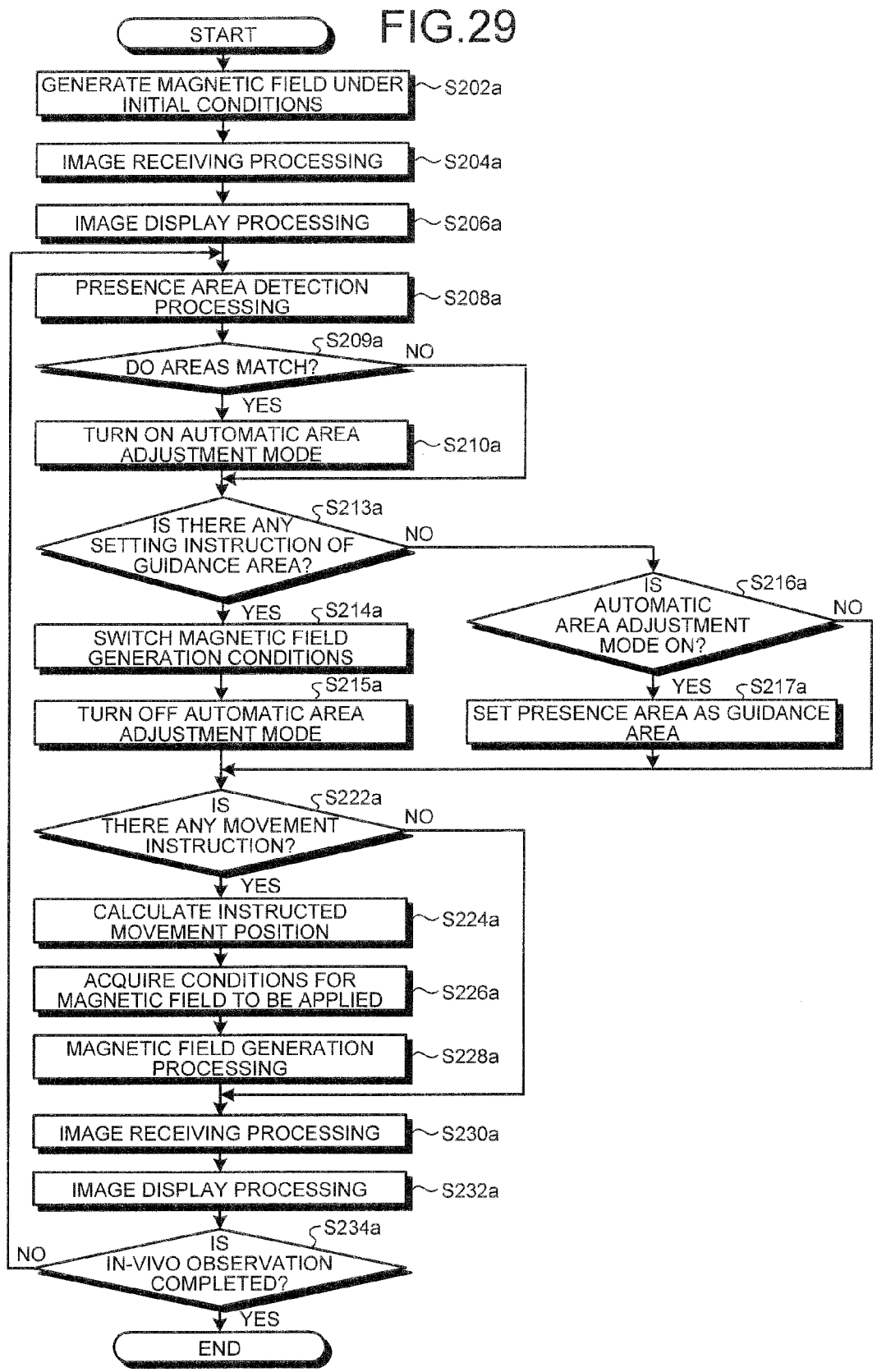
FIG. 29 is a flow chart showing another processing procedure for guidance processing of the capsule endoscope of the capsule medical device guidance system shown in FIG. 25.

In the second embodiment, smooth magnetic guidance of the capsule endoscope 10 may be enabled by setting an automatic area adjustment mode that sets magnetic field generation conditions so as to correspond to the area in which the capsule endoscope 10 is actually present by performing each processing procedure shown in FIG. 29.

As shown in FIG. 29, if, like step S2 shown in FIG. 19, the input unit 6 inputs instruction information to instruct the start of an in-vivo observation, the magnetic field control instruction unit 245 transmits instruction information to the magnetic field control unit 8 to cause the magnetic field generation unit 2 to generate a magnetic field under initial conditions (step S202a). Next, like step S4 and step S6 in FIG. 19, the image receiving unit 41 performs image receiving processing (step S204a) and the image display control unit 42 performs image display processing (step S206a).

Then, the position detection unit 243 performs presence area detection processing to detect the presence area of the capsule endoscope 10 (step S208a). Then, based on a detection result of the position detection unit 243, the magnetic field control instruction unit 245 determines whether the presence area of the capsule endoscope 10 and the guidance area selected by the operation input unit 60 match (step S209a). If the magnetic field control instruction unit 245 determines that the presence area of the capsule endoscope 10 and the guidance area selected by the operation input unit 60 match (step S209a: Yes), the magnetic field control instruction unit 245 turns on the automatic area adjustment mode (step S210a).

If the magnetic field control instruction unit 245 determines that the presence area of the capsule endoscope 10 and the guidance area selected by the operation input unit 60 do not match (step S209a: No) or after the processing in step S210a is completed, like step S8 in FIG. 19, the magnetic-field-condition switching unit 46 determines whether there is any setting instruction of the guidance area (step S213a).

If the magnetic-field-condition switching unit 46 determines that there is a setting instruction of the guidance area (step S213a: Yes), the magnetic-field-condition switching unit 46 switches magnetic field generation conditions by the magnetic field generation unit 2 in accordance with the guidance area selected by the operation input unit 60 based on the input selection information (step S214a). Then, the magnetic field control instruction unit 245 issues instructions to the magnetic field generation unit 2 to generate a magnetic field so as to guide the capsule endoscope 10 into the selected guidance area and turns off the automatic area adjustment mode after the area in which the capsule endoscope 10 is actually present moves to the guidance area selected by the operation input unit 60 so that the presence area and the guidance area match (step S215a).

On the other hand, if the magnetic-field-condition switching unit 46 determines that there is no setting instruction of the guidance area (step S213a: No), the magnetic field control instruction unit 245 determines whether the automatic area adjustment mode is in the ON state (step S216a). If the magnetic field control instruction unit 245 determines that the automatic area adjustment mode is in the ON state (step S216a: Yes), the magnetic field control instruction unit 245 sets the area in which the capsule endoscope 10 is actually present as the guidance area (step S217a). The magnetic-field-condition switching unit 46 switches magnetic field generation conditions by the magnetic field generation unit 2 to correspond to the guidance area set by the magnetic field control instruction unit 245 in the setting processing in step S217a.

If, after the processing in step S215a is completed, the magnetic field control instruction unit 245 determines that the automatic area adjustment mode is not in the ON state (step S216a: No) or the processing in step S217a is completed, like step S12 in FIG. 19, the magnetic field control instruction unit 245 determines whether there is any movement instruction of the capsule endoscope 10 (step S222a). If the magnetic field control instruction unit 245 determines that there is a movement instruction of the capsule endoscope 10 (step S222a: Yes), like in the first embodiment, the magnetic field control instruction unit 245 calculates the movement position instructed by the operation information from the operation input unit 60 (step S224a) and acquires conditions for the magnetic field applied to the permanent magnet 19 of the capsule endoscope 10 based on magnetic field generation conditions corresponding to the guidance area (step S226a). Then, the magnetic field control instruction unit 245 issues instructions to the magnetic field control unit 8 to generate a magnetic field under the acquired magnetic field conditions and the magnetic field generation unit 2 performs magnetic field generation processing to generate a magnetic field under the instructed conditions (step S228a). If the magnetic field control instruction unit 245 determines that there is no movement instruction of the capsule endoscope 10 (step S222a: No) or the magnetic field generation processing (step S228a) is completed, the image receiving unit 41 performs image receiving processing (step S230a) and the image display control unit 42 performs image display processing (step S232a). As a result, the display unit 5 successively displays in-vivo images captured by the capsule endoscope 10. Subsequently, the external control unit 204 determines whether the in-vivo observation has completed based on the instruction information input by the input unit 6 (step S234a). If the external control unit 204 determines that the in-vivo observation has not completed (step S234a: No), the external control unit 204 returns to step S208a to continue the in-vivo observation and performs presence area verification processing. If the external control unit 204 determines that the in-vivo observation has completed (step S234a: Yes), the external control unit 204 terminates the in-vivo observation.

If the automatic area adjustment mode is set, magnetic field generation conditions can automatically be switched to correspond to the area in which the capsule endoscope 10 is actually present by performing each processing procedure shown in FIG. 29. As a result, even if the presence area in which the capsule endoscope 10 is actually present deviates from the guidance area set by the operation input unit 60 such as when the capsule endoscope 10 moves to the liquid surface while the capsule endoscope 10 is being guided by setting the submerged area as the guidance area, the guidance area is automatically switched to the presence area. Then, the guidance area will be switched to the presence area, and thus, magnetic field generation conditions are also switched to conditions corresponding to the area in which the capsule endoscope 10 is actually present. Thus, by performing each processing procedure shown in FIG. 29, stable guidance can always be realized in the area in which the capsule endoscope 10 is present.

Third Embodiment

Next, a third embodiment will be described. When the capsule endoscope 10 is moved by generating a uniform gradient magnetic field, the position of the capsule endoscope 10 is frequently not determined and thus, in the third embodiment, the peak position in the horizontal plane of a peak magnetic field generated immediately before is stored and when the magnetic field is switched from a uniform gradient magnetic field to a peak magnetic field, a peak magnetic field having the peak in the stored position is generated to determine the position of the capsule endoscope.

Figure 30:
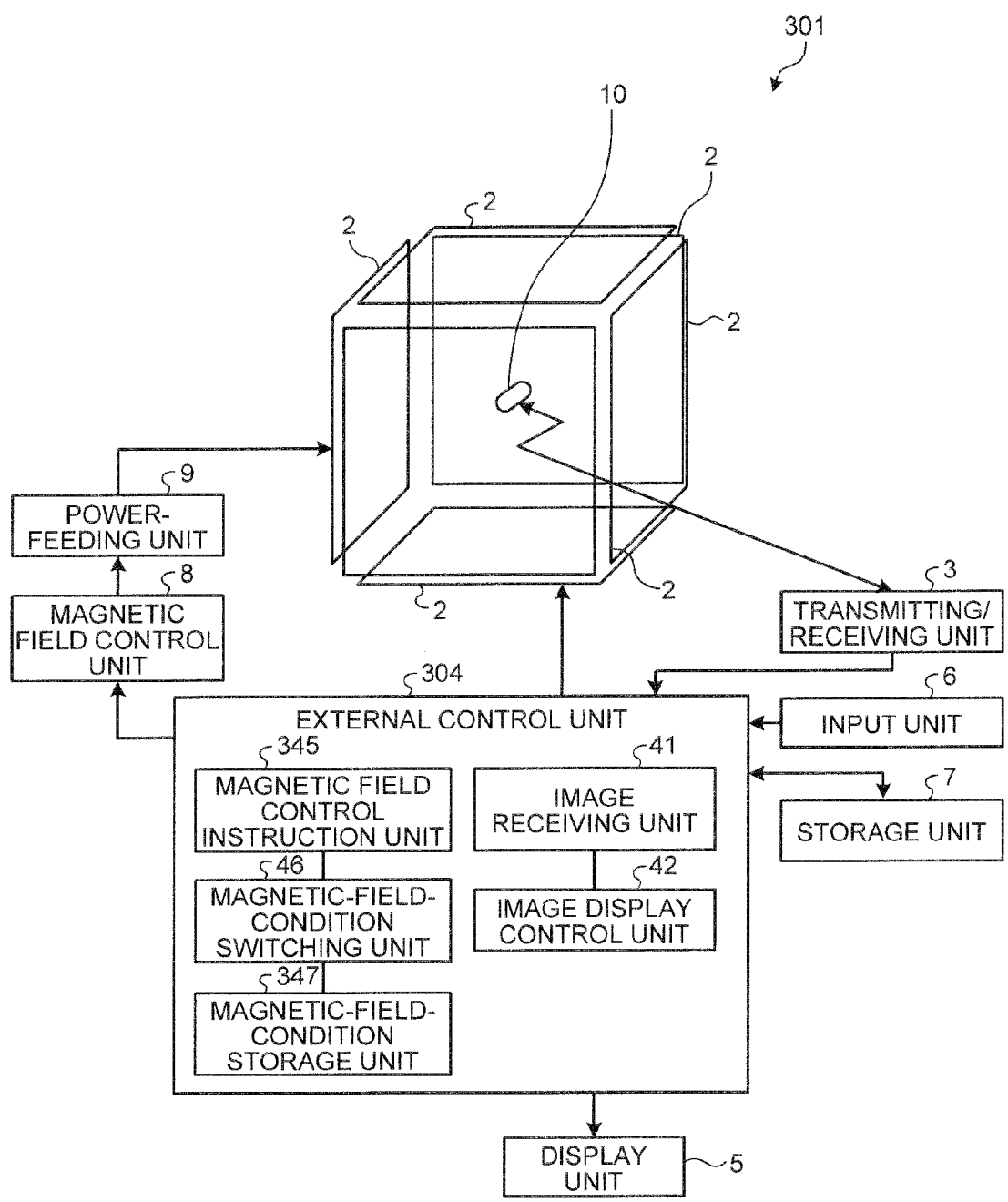
FIG. 30 is a schematic view showing the overall configuration of a capsule medical device guidance system according to a third embodiment.

FIG. 30 is a schematic view showing the overall configuration of a capsule medical device guidance system according to the third embodiment of the invention. As shown in FIG. 30, a capsule medical device guidance system 301 according to the third embodiment includes, instead of the external control unit 4 shown in FIG. 1, an external control unit 304. When compared with the external control unit 4, the external control unit 304 further includes, instead of the magnetic field control instruction unit 45, a magnetic field control instruction unit 345 and, instead of the magnetic-field-condition storage unit 47, a magnetic-field-condition storage unit 347.

The magnetic field control instruction unit 345 causes the magnetic-field-condition storage unit 347 to store magnetic field conditions corresponding to each guidance area and also the generation position in the horizontal plane of a peak magnetic field generated immediately before, that is, the position of the peak of a peak magnetic field in the horizontal plane. When the magnetic field the magnetic field generation unit 2 is caused to generate is switched from a peak magnetic field to a uniform gradient magnetic field, the magnetic field control instruction unit 345 causes the magnetic-field-condition storage unit 347 to store the generation position of the peak magnetic field in the horizontal plane, that is, the position of the peak of the peak magnetic field in the horizontal plane. More specifically, when the magnetic field the magnetic field generation unit 2 is caused to generate is switched from a peak magnetic field to a uniform gradient magnetic field, the magnetic field control instruction unit 345 causes the magnetic-field-condition storage unit 347 to store a magnetic gradient of the peak magnetic field in the vertical direction. When the magnetic field the magnetic field generation unit 2 is caused to generate is switched from a peak magnetic field to a uniform gradient magnetic field, the magnetic field control instruction unit 345 causes the magnetic-field-condition storage unit 347 to store the direction of the peak magnetic field.

Then, when the magnetic field the magnetic field generation unit 2 is caused to generate is switched from a uniform gradient magnetic field to a peak magnetic field, the magnetic field control instruction unit 345 causes magnetic field generation unit 2 to generate the peak magnetic field in the position stored in the magnetic-field-condition storage unit 347. More specifically, when the magnetic field the magnetic field generation unit 2 is caused to generate is switched from a uniform gradient magnetic field to a peak magnetic field, the magnetic field control instruction unit 345 causes magnetic field generation unit 2 to generate the peak magnetic field in a magnetic gradient in the vertical direction stored in the magnetic-field-condition storage unit 347. When the magnetic field the magnetic field generation unit 2 is caused to generate is switched from a uniform gradient magnetic field to a peak magnetic field, the magnetic field control instruction unit 345 causes the magnetic field generation unit 2 to generate the peak magnetic field in the direction stored in the magnetic-field-condition storage unit 347. When the type of magnetic field is changed by switching the guidance area, the magnetic field control instruction unit 345 performs storage processing and read processing of magnetic field conditions regarding the generation position of a peak magnetic field.

Each type of switching of the guidance area will be described more specifically. First, a case when the guidance area is switched from the liquid surface area to the submerged area or liquid bottom area based on selection information by the operation input unit 60 will be described. This case corresponds to a case when the magnetic field the magnetic field generation unit 2 is caused to generate is switched from a peak magnetic field to a uniform gradient magnetic field.

Figure 31:
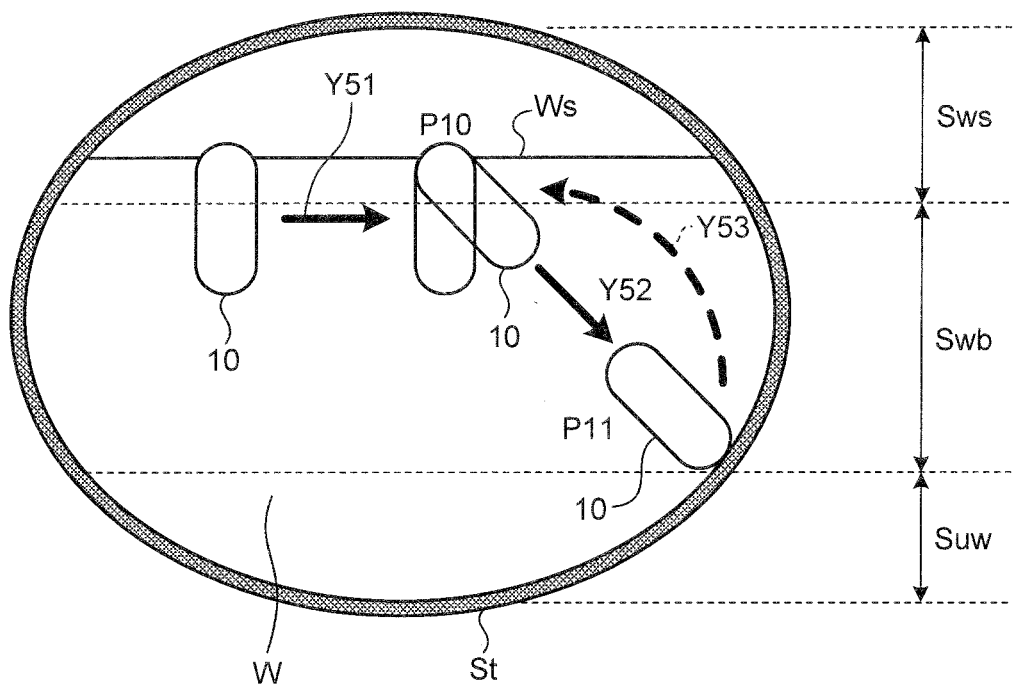
FIG. 31 is a diagram illustrating the state in which the capsule endoscope is positioned inside the stomach of the subject.

First, the guidance area of the capsule endoscope 10 is set to the liquid surface area before switching and thus, the magnetic field generation unit 2 generates a peak magnetic field to move, like an arrow Y51 in FIG. 31, the capsule endoscope 10 to a position P10. If switching instructions to switch the guidance area from the liquid surface area to the submerged area or liquid bottom area are issued in this timing, the magnetic field control instruction unit 345 causes the magnetic-field-condition storage unit 347 to store generation conditions of a peak magnetic field that traps the capsule endoscope 10 in the position P10, for example, the magnetic gradient in the vertical direction of the peak magnetic field and the direction of the peak magnetic field as the generation position of the peak of the peak magnetic field in the horizontal plane.

Then, the magnetic-field-condition switching unit 46 switches magnetic field generation conditions by the magnetic field generation unit 2 in accordance with the newly selected guidance area. Switching of the guidance area necessitates movement downward in the vertical direction from the liquid surface. Thus, in the timing when movement instructions to move the capsule endoscope 10 downward in the vertical direction are issued, the magnetic field control instruction unit 345 once causes the magnetic field generation unit 2 to generate a magnetic field strong enough to be able to resist surface tension of the liquid. In this case, the capsule endoscope 10 automatically moves in diving mode even if the operator does not perform an operation to turn on the diving mode so that the operator can guide the capsule endoscope 10 into the submerged area or liquid bottom area without considering an influence of the surface tension.

Then, the magnetic field control instruction unit 345 causes the magnetic field generation unit 2 to generate a uniform gradient magnetic field to move, like an arrow Y52, the capsule endoscope 10 downward up to, for example, a position P11 close to the stomach wall St according to conditions in Table T1 shown in FIG. 10. The uniform gradient magnetic field is distorted in a strict sense, which makes movement of the capsule endoscope 10 in an environment without friction such as a liquid surface unstable, and thus, the magnetic field control instruction unit 345 may maintain generation of a peak magnetic field by the magnetic field generation unit 2 so that the position of the capsule endoscope 10 can be determined for stable operation until operation information is input by the operation input unit 60. In this case, after operation information is input by the operation input unit 60, the magnetic field control instruction unit 345 causes the magnetic field generation unit 2 to generate a uniform gradient magnetic field.

Next, a case when the guidance area is switched from the submerged area or liquid bottom area to the liquid surface area based on selection information by the operation input unit 60 will be described. This case corresponds to a case when the magnetic field the magnetic field generation unit 2 is caused to generate is switched from a uniform gradient magnetic field to a peak magnetic field. In this case, the magnetic-field-condition switching unit 46 switches magnetic field generation conditions from a uniform gradient magnetic field corresponding to the submerged area or liquid bottom area to a peak magnetic field corresponding to the liquid surface area. Then, the magnetic field control instruction unit 345 acquires generation conditions of the peak magnetic field immediately before stored in the magnetic-field-condition storage unit 347 and causes the magnetic field generation unit 2 to generate a peak magnetic field under the conditions.

As a result, the capsule endoscope 10 that has moved to the position P11 in FIG. 31 returns, as indicated by an arrow Y53, to the position P10 immediately before moving to the liquid bottom. That is, when the guidance area is switched from another area to the liquid surface area, the capsule endoscope 10 automatically returns to the liquid surface position immediately before moving into the submerged area or liquid bottom area. The operator needs only to switch the guidance area from another area to the liquid surface area and can smoothly restart an in-vivo observation by the capsule endoscope 10 and guidance of the capsule endoscope 10 from the position P10 on the liquid surface immediately before moving into the submerged area or liquid bottom area without performing a guidance operation to return the capsule endoscope 10 to the liquid surface.

When the guidance area is switched from the submerged area to the liquid bottom area or from the liquid bottom area to the submerged area, the type of magnetic field in magnetic field generation conditions is not switched and remains the uniform gradient magnetic field and thus, there is no need for the magnetic field control instruction unit 345 to perform storage processing concerning generation conditions of a peak magnetic field.

Figure 32:
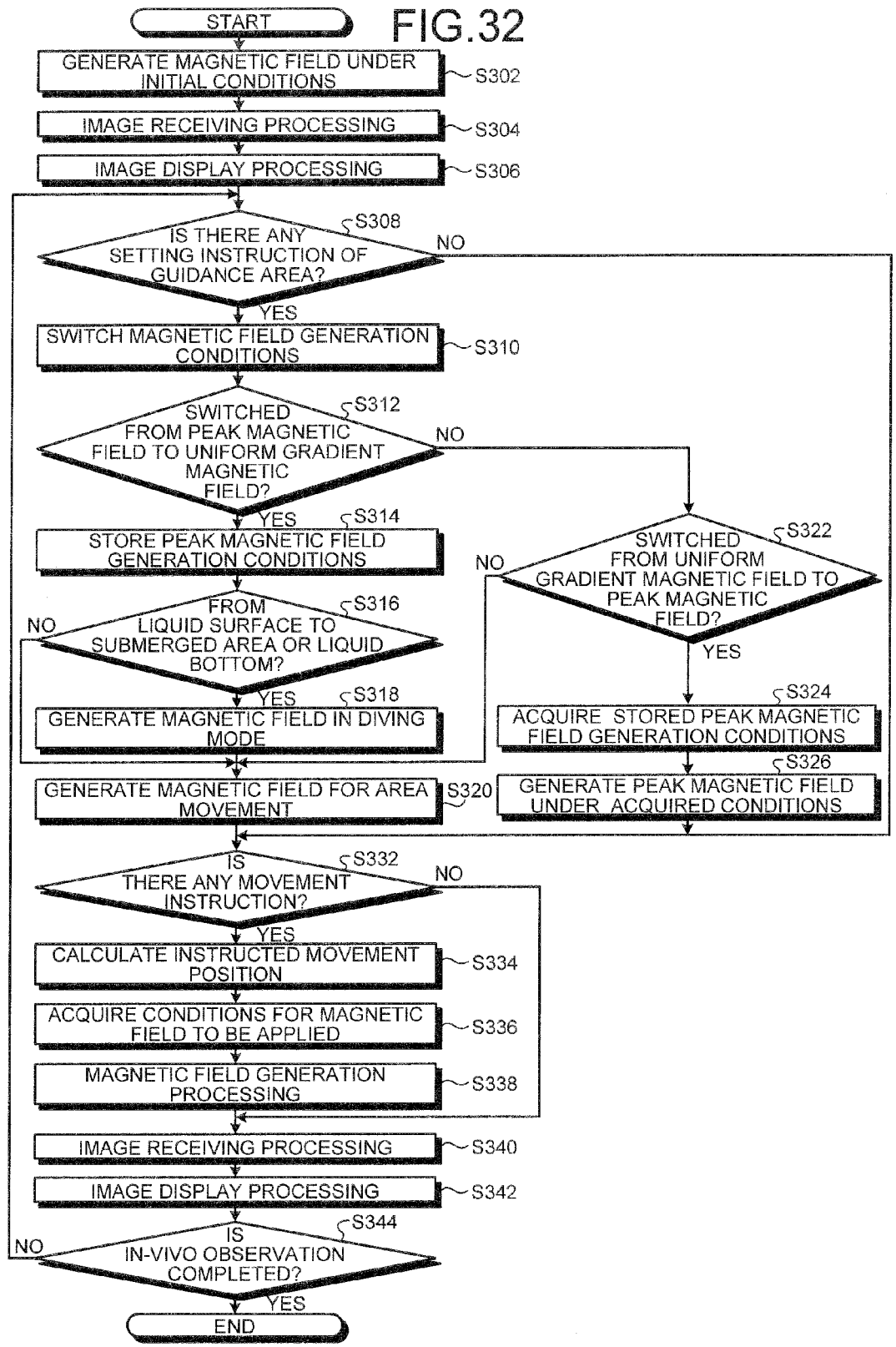
FIG. 32 is a flow chart showing the processing procedure for guidance processing of the capsule endoscope of the capsule medical device guidance system shown in FIG. 30.

Next, guidance processing of the capsule endoscope 10 of the capsule medical device guidance system 301 shown in FIG. 30 will be described with reference to FIG. 32. FIG. 32 is a flow chart showing the processing procedure for guidance processing of the capsule endoscope 10 of the capsule medical device guidance system 301 shown in FIG. 30.

As shown in FIG. 32, if, like step S2 shown in FIG. 19, the input unit 6 first inputs instruction information to instruct the start of an in-vivo observation, the magnetic field control instruction unit 345 transmits instruction information to the magnetic field control unit 8 to cause the magnetic field generation unit 2 to generate a magnetic field under initial conditions (step S302). Next, like step S4 and step S6 in FIG. 19, the image receiving unit 41 performs image receiving processing (step S304) and the image display control unit 42 performs image display processing (step S306).

In the external control unit 304, like step S8 in FIG. 19, the magnetic-field-condition switching unit 46 determines whether there is any setting instruction of the guidance area (step S308). If the magnetic-field-condition switching unit 46 determines that there is a setting instruction of the guidance area (step S308: Yes), the magnetic-field-condition switching unit 46 switches magnetic field generation conditions by the magnetic field generation unit 2 in accordance with the guidance area selected by the operation input unit 60 based on the input selection information (step S310). If the magnetic-field-condition switching unit 46 determines that there is no setting instruction of the guidance area (step S308: No), the magnetic-field-condition switching unit 46 proceeds to step S332 described below.

Next, the magnetic field control instruction unit 345 determines whether the type of magnetic field in magnetic field generation conditions is switched from the peak magnetic field to the uniform gradient magnetic field in the switching processing of magnetic field generation conditions in step S310 based on the setting instruction of the guidance area (step S312).

A case when the magnetic field control instruction unit 345 determines that the type of magnetic field in magnetic field generation conditions is switched from the peak magnetic field to the uniform gradient magnetic field (step S312: Yes) will be described. This case is a case when the guidance area is switched from the liquid surface area to the submerged area or liquid bottom area. In this case, the magnetic field control instruction unit 345 causes the magnetic-field-condition storage unit 347 to store generation conditions of the peak magnetic field generated immediately before (step S314). Then, the magnetic field control instruction unit 345 determines whether there is any movement instruction from the liquid surface area to the submerged area or liquid bottom area (step S316). That is, the magnetic field control instruction unit 345 determines whether the operation input unit 60 has input a movement instruction of the capsule endoscope 10 downward in the vertical direction as operation information.

If the magnetic field control instruction unit 345 determines that there is no movement instruction from the liquid surface area to the submerged area or liquid bottom area (step S316: No), the magnetic field control instruction unit 345 proceeds to step S320 described below. In the other hand, if the magnetic field control instruction unit 345 determines that there is a movement instruction from the liquid surface area to the submerged area or liquid bottom area (step S316: Yes), the magnetic field control instruction unit 345 causes the magnetic field generation unit 2 to generate a magnetic field in diving mode described above (step S318) to correctly move the capsule endoscope 10 from the liquid surface area to the submerged area or liquid bottom area. Then, the magnetic field control instruction unit 345 causes the magnetic field generation unit 2 to generate a magnetic field to move the capsule endoscope 10 to the submerged area or liquid bottom area selected as the guidance area by generating a uniform gradient magnetic field according to magnetic field generation conditions switched by the magnetic-field-condition switching unit 46 (step S320) to move the capsule endoscope 10 into the selected guidance area.

In contrast, if the magnetic field control instruction unit 345 determines that the type of magnetic field in magnetic field generation conditions is not switched from the peak magnetic field to the uniform gradient magnetic field in the switching processing of magnetic field generation conditions in step S310 based on the setting instruction of the guidance area (step S312: No), the magnetic field control instruction unit 345 further determines whether the type of magnetic field in magnetic field generation conditions is not switched from the uniform gradient magnetic field to the peak magnetic field (step S322).

A case when the magnetic field control instruction unit 345 determines that the type of magnetic field in magnetic field generation conditions is switched from the uniform gradient magnetic field to the peak magnetic field (step S322: Yes) will be described. This case is a case when the guidance area is switched from the submerged area or liquid bottom area to the liquid surface area. In this case, the magnetic field control instruction unit 345 acquires generation conditions of the peak magnetic field immediately before stored in the magnetic-field-condition storage unit 347 (step S324) and causes the magnetic field generation unit 2 to generate a peak magnetic field under the acquired conditions (step S326). As a result, the capsule endoscope 10 will return to the liquid surface position where the capsule endoscope 10 was positioned immediately before of the liquid surface area.

In contrast, a case when the magnetic field control instruction unit 345 determines that the type of magnetic field in magnetic field generation conditions is not switched from the uniform gradient magnetic field to the peak magnetic field (step S322: No), that is, the type of magnetic field in magnetic field generation conditions remains the uniform gradient magnetic field corresponds to a case when the guidance area is switched from the submerged area to the liquid bottom area or from the liquid bottom area to the submerged area. In this case, the magnetic field control instruction unit 345 causes the magnetic field generation unit 2 to generate a magnetic field to move the capsule endoscope 10 to the submerged area or liquid bottom area selected as the guidance area by generating a uniform gradient magnetic field according to magnetic field generation conditions switched by the magnetic-field-condition switching unit 46 (step S320) to move the capsule endoscope 10 into the selected guidance area.

After the magnetic field generation unit 2 being caused to generate a magnetic field to move the capsule endoscope 10 into the selected guidance area, like in the first embodiment, the magnetic field control instruction unit 345 determines whether there is any movement instruction of the capsule endoscope 10 (step S332). If the magnetic field control instruction unit 345 determines that there is a movement instruction of the capsule endoscope 10 (step S332: Yes), like in the first embodiment, the magnetic field control instruction unit 345 calculates the movement position instructed by the operation information from the operation input unit 60 (step S334) and acquires conditions for the magnetic field applied to the permanent magnet 19 of the capsule endoscope 10 based on magnetic field generation conditions corresponding to the guidance area (step S336). Then, the magnetic field control instruction unit 345 issues instructions to the magnetic field control unit 8 to generate a magnetic field under the acquired magnetic field conditions and the magnetic field generation unit 2 performs magnetic field generation processing to generate a magnetic field under the instructed conditions (step S338). As a result, the capsule endoscope 10 moves in the direction and to the position following the operation processing by the operation input unit 60.

If the magnetic field control instruction unit 345 determines that there is no movement instruction of the capsule endoscope 10 (step S332: No) or the magnetic field generation processing (step S338) is completed, the image receiving unit 41 performs image receiving processing (step S340) and the image display control unit 42 performs image display processing (step S342). As a result, the display unit 5 successively displays in-vivo images captured by the capsule endoscope 10. Subsequently, the external control unit 304 determines whether the in-vivo observation has completed based on the instruction information input by the input unit 6 (step S344). If the external control unit 304 determines that the in-vivo observation has not completed (step S344: No), the external control unit 304 returns to step S308 to continue the in-vivo observation and determines whether there is any setting instruction of the guidance area. If the external control unit 304 determines that the in-vivo observation has completed (step S344: Yes), the external control unit 304 terminates the in-vivo observation.

Thus, in the third embodiment, if the type of magnetic field is switched from the uniform gradient magnetic field to the peak magnetic field, the magnetic-field-condition storage unit 347 is caused to store the peak position of the peak magnetic field in the horizontal plane generated immediately before and when the type of magnetic field is switched from the uniform gradient magnetic field to the peak magnetic field, the position of the capsule endoscope 10 is determined by generating a peak magnetic field having the peak in the position the magnetic-field-condition storage unit 347 is caused to store. Thus, according to the third embodiment, even if the operator cannot judge the position of the capsule endoscope 10 when the capsule endoscope 10 is moved by generating a uniform gradient magnetic field, the capsule endoscope 10 automatically returns to the original liquid surface position when the magnetic field is switched from the gradient magnetic field to the peak magnetic field and therefore, the operator can smoothly restart an in-vivo observation by the capsule endoscope 10 and guidance of the capsule endoscope 10 from the original liquid surface position without performing a guidance operation to return the capsule endoscope 10 to the liquid surface.

Figure 33:
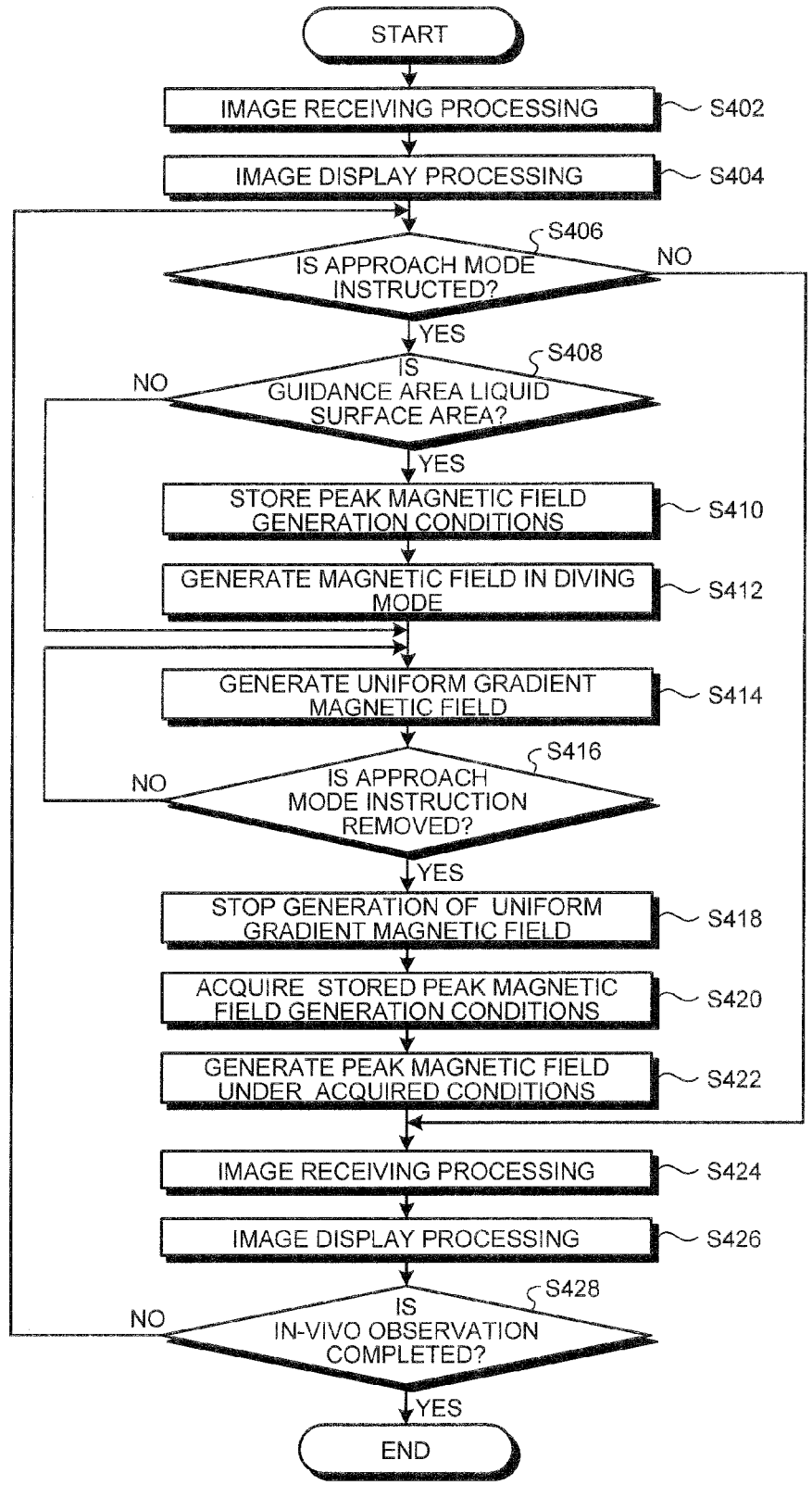
FIG. 33 is a flow chart showing the processing procedure for approach mode processing of the capsule endoscope of the capsule medical device guidance system shown in FIG. 30.

In the capsule medical device guidance system 301, storage processing concerning generation conditions of a peak magnetic field is performed, in addition to a case when the guidance area is switched, when the capsule endoscope 10 positioned in the liquid surface area is caused to approach an imaging target in the submerged area or liquid bottom area due to the selection of the approach mode while an in-vivo observation is made by using the capsule endoscope 10. This case will be described with reference to FIG. 33. FIG. 33 is a flow chart showing the processing procedure for approach mode processing in the capsule medical device guidance system 301 shown in FIG. 30.

In the external control unit 304, as shown in FIG. 33, image receiving processing by the image receiving unit 41 is performed (step S402) and image display processing by the image display control unit 42 is performed (step S404) and the magnetic field control instruction unit 345 determines whether the approach mode is instructed based on operation information from the operation input unit 60 (step S406). If the magnetic field control instruction unit 345 determines that the approach mode is instructed (step S406: Yes), the magnetic field control instruction unit 345 determines whether the set guidance area is the liquid surface area (step S408). If the magnetic field control instruction unit 345 determines that the set guidance area is the liquid surface area (step S408: Yes), the position of the capsule endoscope 10 in the horizontal plane is controlled by a peak magnetic field and the magnetic field control instruction unit 345 causes the magnetic-field-condition storage unit 347 to store peak magnetic field generation conditions including the peak position of the peak magnetic field in the horizontal plane (step S410). Then, the magnetic field control instruction unit 345 causes the magnetic field generation unit 2 to generate a magnetic field in diving mode described above (step S412). As a result, the capsule endoscope 10 can correctly be moved from the liquid surface area to the submerged area.

Then, after the processing in step S412 or if the magnetic field control instruction unit 345 determines that the set guidance area is not the liquid surface area (step S408: No), the magnetic field control instruction unit 345 causes the magnetic field generation unit 2 to generate a uniform gradient magnetic field having a gradient in the long axis La direction of the capsule endoscope 10 (step S414) to cause the capsule endoscope 10 to approach an imaging target.

Next, the magnetic field control instruction unit 345 determines whether the instruction of the approach mode is removed (step S416). If the magnetic field control instruction unit 345 determines that the instruction of the approach mode is not removed (step S416: No), that is, the approach mode is valid, the magnetic field control instruction unit 345 returns to step S414 to continue to cause the magnetic field generation unit 2 to generate a uniform gradient magnetic field. In contrast, if the magnetic field control instruction unit 345 determines that the instruction of the approach mode is removed (step S416: Yes), the magnetic field control instruction unit 345 causes the magnetic field generation unit 2 to stop generating a uniform gradient magnetic field (step S418). Then, the magnetic field control instruction unit 345 acquires generation conditions of the peak magnetic field immediately before stored in the magnetic-field-condition storage unit 347 (step S420) and causes the magnetic field generation unit 2 to generate a peak magnetic field under the acquired conditions (step S422). As a result, the capsule endoscope 10 will return to the liquid surface position before the approach mode is set.

Thus, the operator can check approached images by pressing the approach button 64. Then, when the operator releases his (her) finger from the approach button 64, the capsule endoscope 10 will automatically return to the liquid surface position before the approach button 64 being pressed and thus, the operator can restart guidance of the capsule endoscope 10 from the liquid surface position before the approach button 64 being pressed.

If the magnetic field control instruction unit 345 determines that the approach mode is not instructed (step S406: No) or the peak magnetic field generation processing by the magnetic field generation unit 2 in step S422 is completed, the image receiving unit 41 performs image receiving processing (step S424) and the image display control unit 42 performs image display processing (step S426). As a result, the display unit 5 successively displays in-vivo images captured by the capsule endoscope 10. Subsequently, the external control unit 304 determines whether the in-vivo observation has completed based on the instruction information input by the input unit 6 (step S428). If the external control unit 304 determines that the in-vivo observation has not completed (step S428: No), the external control unit 304 returns to step S406 to continue the in-vivo observation to determine whether there is an instruction of approach mode. If the external control unit 304 determines that the in-vivo observation has completed (step S428: Yes), the external control unit 304 terminates the in-vivo observation.

Figure 34:
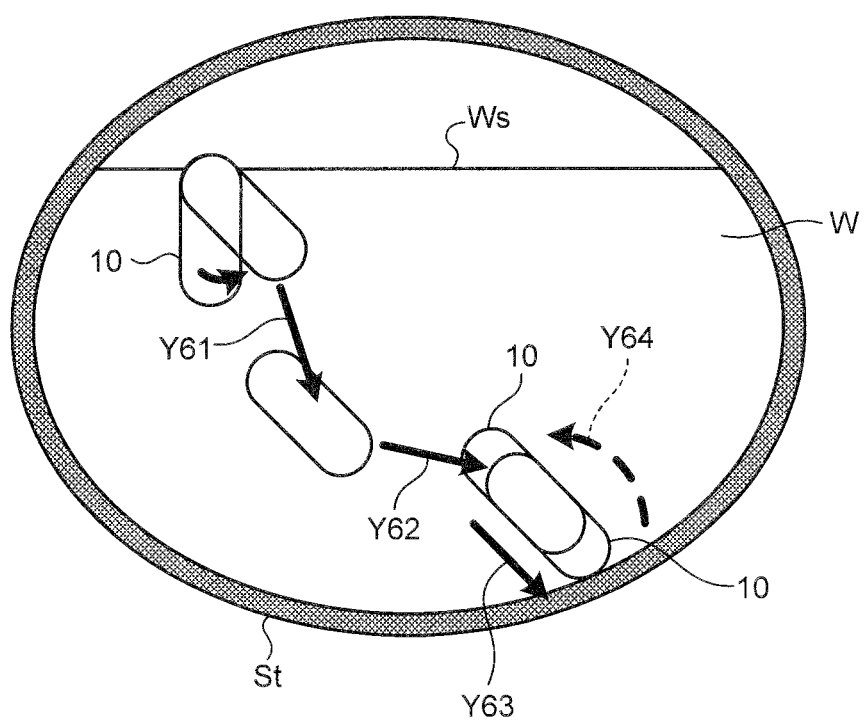
FIG. 34 is a diagram illustrating the state in which the capsule endoscope is positioned inside the stomach of the subject.

The approach mode can also be applied when the capsule endoscope 10 is guided in the submerged area by using a peak magnetic field. When, as shown in FIG. 34, the capsule endoscope 10 is guided, as indicated by arrows Y61, Y62, in the submerged area by using a peak magnetic field and then the approach mode is instructed, the magnetic field control instruction unit 345 similarly causes the magnetic-field-condition storage unit 347 to store generation conditions of the peak magnetic field immediately before and causes the magnetic field generation unit 2 to generate a uniform gradient magnetic field to move the capsule endoscope 10, as indicated by an arrow Y63, closer to an imaging target of the stomach wall St. When the instruction of the approach mode is removed, the magnetic field control instruction unit 345 acquires stored peak magnetic field generation conditions and causes the magnetic field generation unit 2 to generate a peak magnetic field under the acquired conditions. As a result, the capsule endoscope 10 returns to, as indicated by an arrow Y64, the position in the submerged area before the approach mode being instructed.

Figure 35:
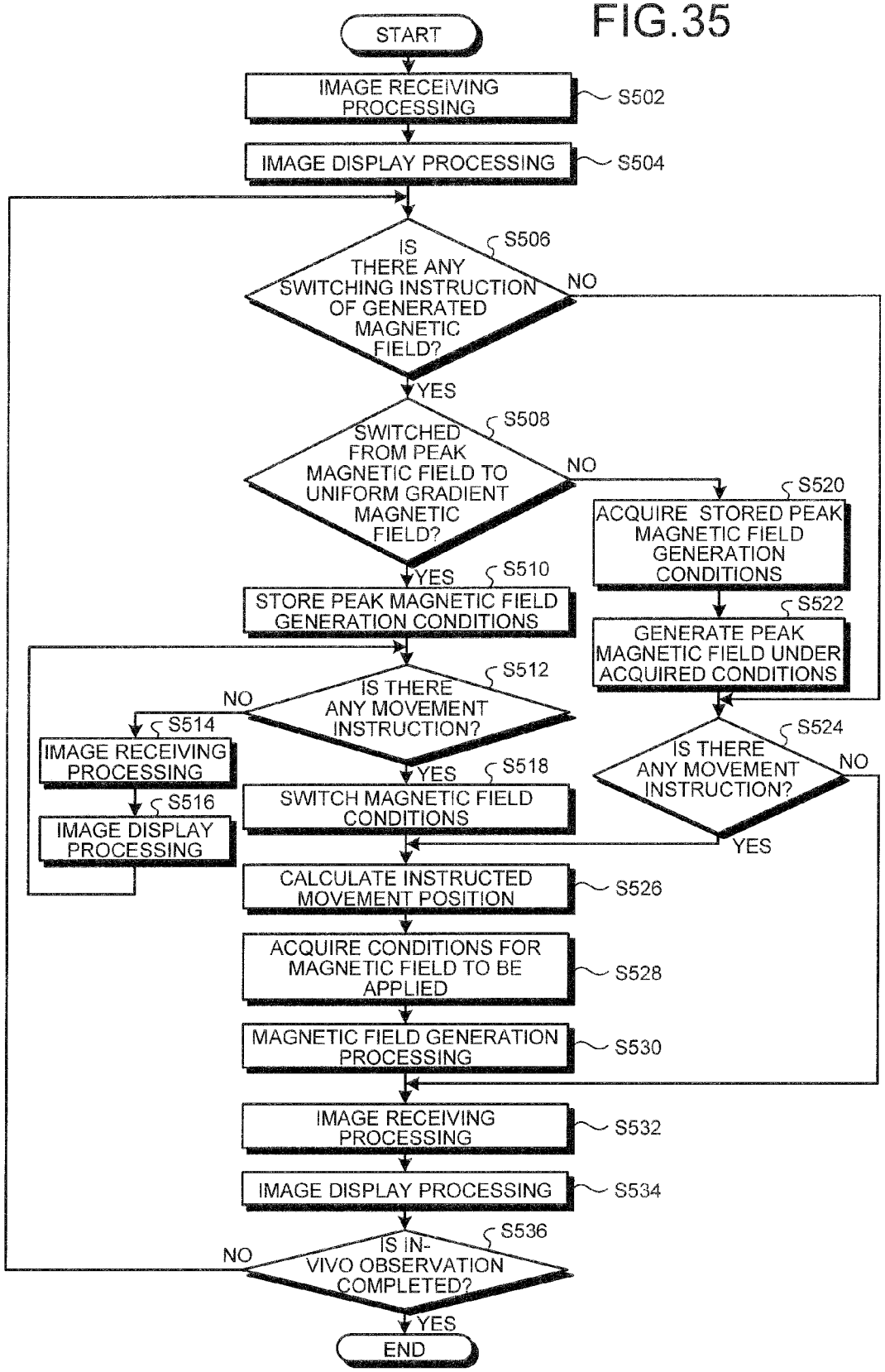
FIG. 35 is a flow chart showing another processing procedure for guidance processing of the capsule endoscope of the capsule medical device guidance system shown in FIG. 30.

The approach mode can also be applied when the type of magnetic field generated by the magnetic field generation unit 2 is manually switched from the peak magnetic field to the uniform gradient magnetic field or from the uniform gradient magnetic field to the peak magnetic field. This case will be described with reference to FIG. 35. FIG. 35 shows a case when the type of magnetic field is manually switched during in-vivo observation by the capsule endoscope 10.

In the external control unit 304, as shown in FIG. 35, the image receiving unit 41 performs image receiving processing (step S502) and the image display control unit 42 performs image display processing (step S504).

Then, in the external control unit 304, the magnetic field control instruction unit 345 determines whether there is any switching instruction of the type of the generated magnetic field based on instruction information from the input unit 6 (step S506). If the magnetic field control instruction unit 345 determines that there is a switching instruction of the type of the generated magnetic field (step S506: Yes), the magnetic field control instruction unit 345 determines whether the type of magnetic field is switched from the peak magnetic field to the uniform gradient magnetic field (step S508).

If the magnetic field control instruction unit 345 determines that the type of magnetic field is switched from the peak magnetic field to the uniform gradient magnetic field (step S508: Yes), the magnetic field control instruction unit 345 causes the magnetic-field-condition storage unit 347 to store peak magnetic field generation conditions including the peak position of the peak magnetic field generated immediately before in the horizontal plane (step S510).

Then, the magnetic field control instruction unit 345 determines whether there is any movement instruction of the capsule endoscope 10 (step S512). If the magnetic field control instruction unit 345 determines that there is no movement instruction of the capsule endoscope 10 (step S512: No), image receiving processing by the image receiving unit 41 is performed (step S514), image display processing by the image display control unit 42 is performed (step S516), and an in-vivo observation by the capsule endoscope 10 is continued before returning to step S512. In contrast, if the magnetic field control instruction unit 345 determines that there is a movement instruction of the capsule endoscope 10 (step S512: Yes), the magnetic-field-condition switching unit 46 switches the type of the magnetic field the magnetic field generation unit 2 is caused to generate from the peak magnetic field to the uniform gradient magnetic field (step S518). Then, the magnetic field control instruction unit 345 calculates the movement position instructed by the operation information from the operation input unit 60 (step S526) and acquires conditions for the magnetic field applied to the permanent magnet 19 of the capsule endoscope 10 based on magnetic field generation conditions corresponding to the guidance area (step S528). Then, the magnetic field control instruction unit 345 issues instructions to the magnetic field control unit 8 to generate a magnetic field under the acquired magnetic field conditions and the magnetic field generation unit 2 performs magnetic field generation processing to generate a magnetic field under the instructed conditions (step S530). That is, the magnetic field control instruction unit 345 maintains generation of the peak magnetic field by the magnetic field generation unit 2 so as to be able to determine the position of the capsule endoscope 10 for stable operation until the operation input unit 60 inputs operation information and after operation information is input by the operation input unit 60, causes the magnetic field generation unit 2 to generate a uniform gradient magnetic field.

If the magnetic field control instruction unit 345 determines that the type of magnetic field is not switched from the peak magnetic field to the uniform gradient magnetic field (step S508: No), that is, the type of magnetic field is switched from the uniform gradient magnetic field to the peak magnetic field, the magnetic field control instruction unit 345 acquires generation conditions of the peak magnetic field immediately before stored in the magnetic-field-condition storage unit 347 (step S520) and causes the magnetic field generation unit 2 to generate a peak magnetic field under the acquired conditions (step S522). As a result, the capsule endoscope 10 will return to the liquid surface position where the capsule endoscope 10 was positioned before. Then, the magnetic field control instruction unit 345 determines whether there is any movement instruction of the capsule endoscope 10 (step S524). If the magnetic field control instruction unit 345 determines that there is no switching instruction of the type of the generated magnetic field (step S506: No), the magnetic field control instruction unit 345 also proceeds to step S524.

If the magnetic field control instruction unit 345 determines that there is a movement instruction of the capsule endoscope 10 (step S524: Yes), the magnetic field control instruction unit 345 calculates the movement position instructed by the operation information from the operation input unit 60 (step S526) and acquires conditions for the magnetic field applied to the permanent magnet 19 of the capsule endoscope 10 based on magnetic field generation conditions corresponding to the guidance area (step S528). Then, the magnetic field control instruction unit 345 issues instructions to the magnetic field control unit 8 to generate a magnetic field under the acquired magnetic field conditions and the magnetic field generation unit 2 performs magnetic field generation processing to generate a magnetic field under the instructed conditions (step S530). As a result, the capsule endoscope 10 moves in the direction and to the position following the operation processing by the operation input unit 60.

If the magnetic field control instruction unit 345 determines that there is no movement instruction of the capsule endoscope 10 (step S524: No) or the magnetic field generation processing (step S530) is completed, the image receiving unit 41 performs image receiving processing (step S532) and the image display control unit 42 performs image display processing (step S534). As a result, the display unit 5 successively displays in-vivo images captured by the capsule endoscope 10. Subsequently, the external control unit 304 determines whether the in-vivo observation has completed based on the instruction information input by the input unit 6 (step S536). If the external control unit 304 determines that the in-vivo observation has not completed (step S536: No), the external control unit 304 returns to step S506 to continue the in-vivo observation. If the external control unit 304 determines that the in-vivo observation has completed (step S536: Yes), the external control unit 304 terminates the in-vivo observation.

Also in this case, even if the position of the capsule endoscope 10 cannot be judged when the capsule endoscope is moved by generating a uniform gradient magnetic field, the capsule endoscope 10 automatically returns to the original liquid surface position when the magnetic field is switched from the gradient magnetic field to the peak magnetic field and therefore, the operator can smoothly restart an in-vivo observation by the capsule endoscope 10 and guidance of the capsule endoscope 10 from the original liquid surface position without performing a guidance operation to return the capsule endoscope 10 to the liquid surface.

Figure 36:
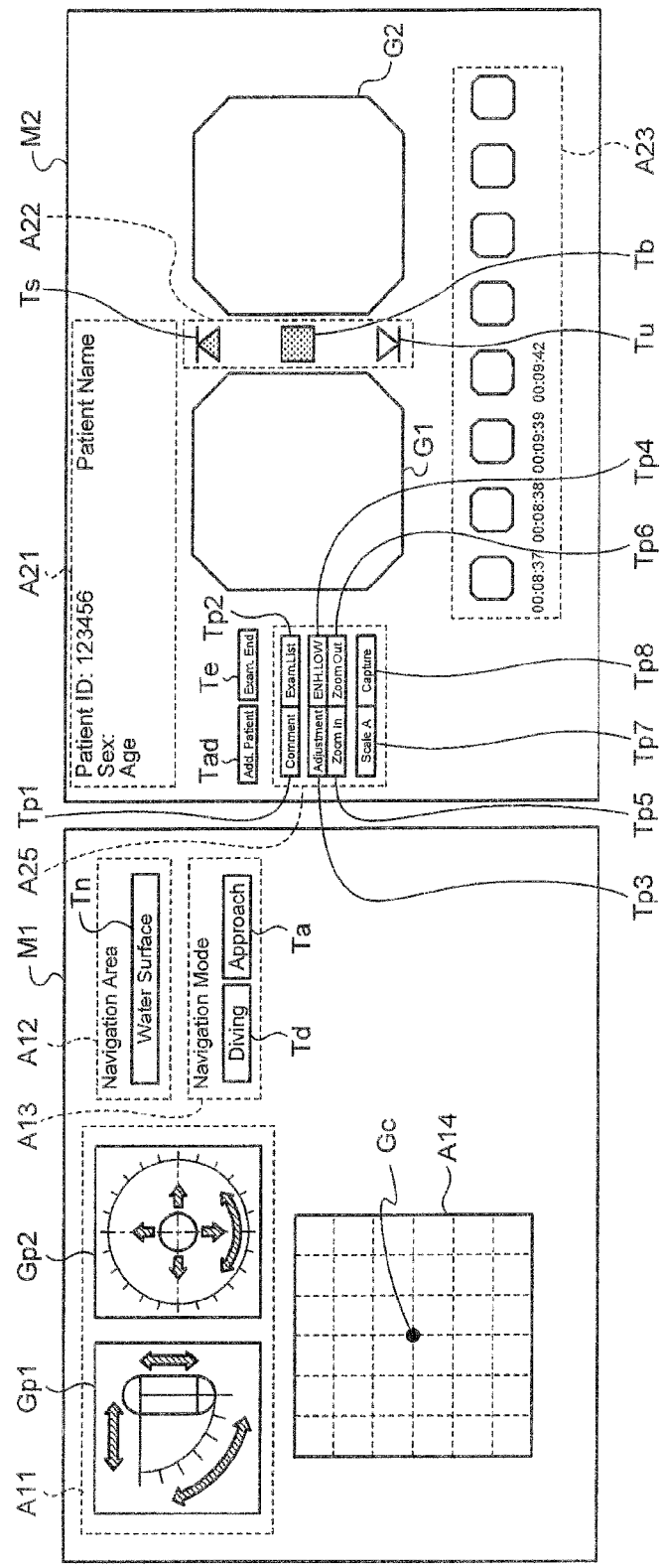
FIG. 36 is a diagram exemplifying a menu screen displayed in the display screen of the display unit shown in FIG. 1.

Next, the display content displayed by the display unit 5 will be described. FIG. 36 is a diagram exemplifying a menu screen displayed by the display unit 5. As shown in FIG. 36, the display unit 5 displays two menu screens of a guidance menu M1 and an observation menu M2. The guidance menu M1 of these menus is a menu screen to assist in the guidance of the capsule endoscope 10 and the observation menu M2 is a menu screen to assist in the observation of in-vivo images transmitted by the capsule endoscope 10.

First, the guidance menu M1 will be described. The display unit 5 displays a posture diagram Gp1 in a vertical plane and a posture diagram Gp2 in a horizontal plane as posture diagrams of the capsule endoscope 10 of the guidance menu M1 in an upper left area A11. The posture of the capsule endoscope 10 displayed in each of the posture diagrams Gp1, Gp2 is estimated from magnetic field conditions generated by the magnetic field generation unit 2. In these posture diagrams Gp1, Gp2, directions in which the capsule endoscope 10 can be guided are indicated by arrows and when some guidance direction is operated and input, the display color of the arrow corresponding to the input direction is changed to assist in the operation of the operator.

Figure 37:
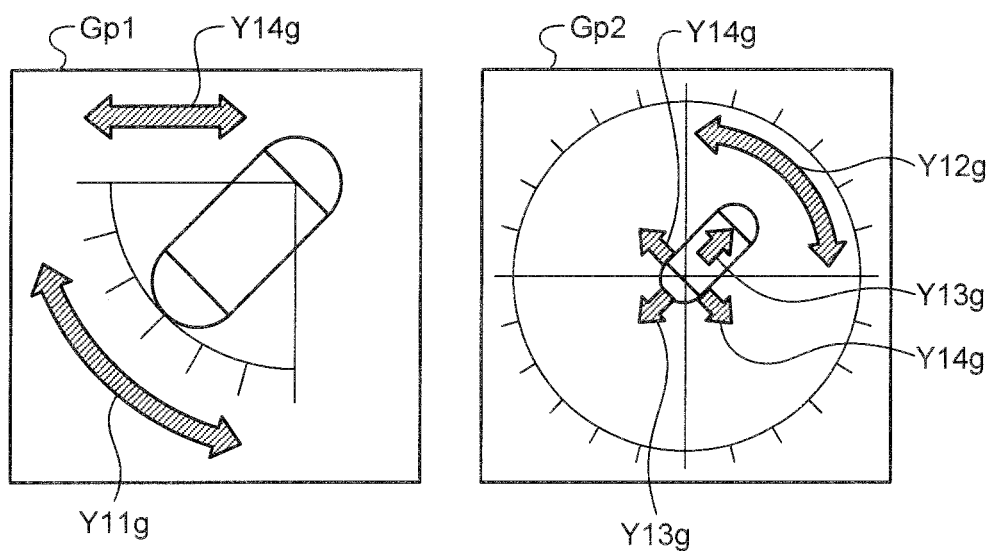
FIG. 37 is a diagram illustrating a posture diagram of the capsule endoscope shown in FIG. 36.
Figure 38:
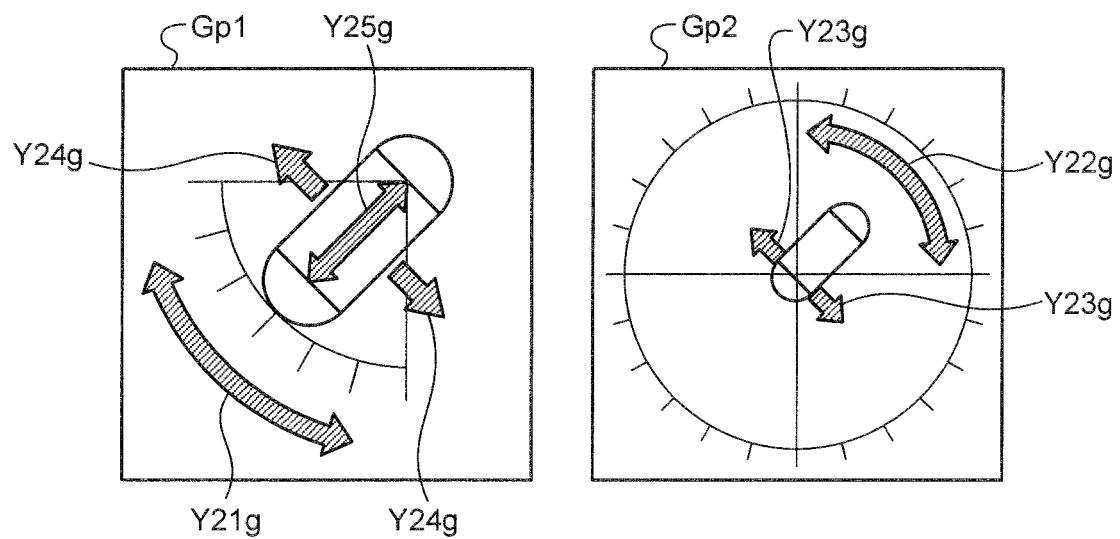
FIG. 38 is a diagram illustrating the posture diagram of the capsule endoscope shown in FIG. 36.
Figure 39:
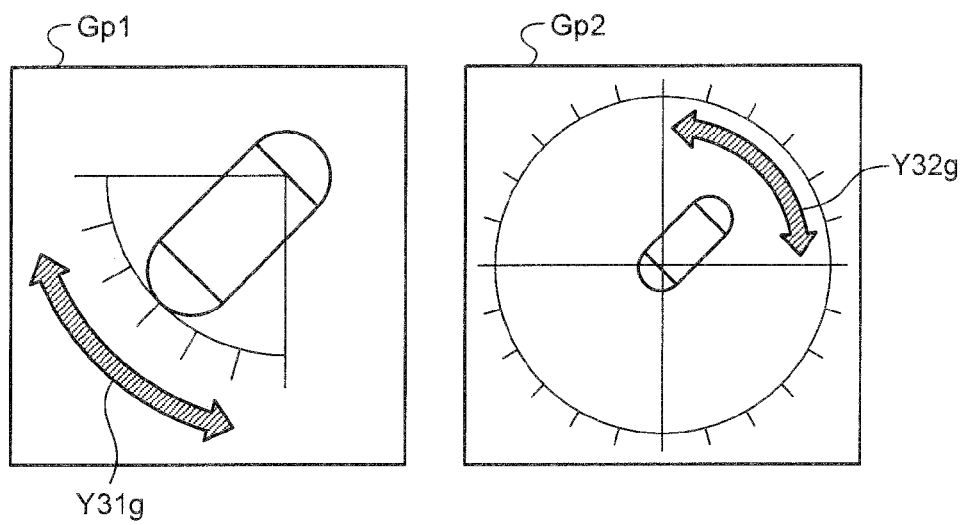
FIG. 39 is a diagram illustrating the posture diagram of the capsule endoscope shown in FIG. 36.
Figure 40:
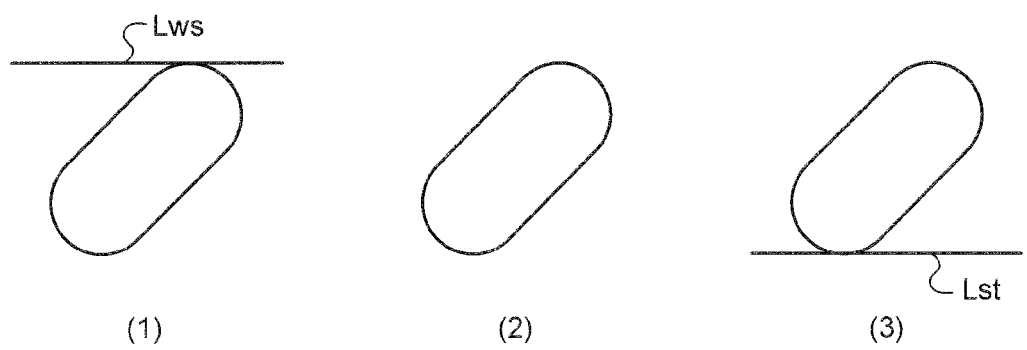
FIG. 40 is a diagram illustrating the posture diagram of the capsule endoscope shown in FIG. 36.

As described above, directions in which the capsule endoscope 10 can be guided are different depending on the guidance area and thus, arrows in the posture diagrams Gp1, Gp2 are different for each guidance area. If, for example, the liquid surface area is selected as the guidance area, as illustrated in FIG. 37, an arrow Y11g corresponding to a tilting operation, an arrow Y12g corresponding to a rotation operation, an arrow Y13g corresponding to a horizontal backward operation or horizontal forward operation, and an arrow Y14g corresponding to a horizontal right operation or horizontal left operation are displayed in the posture diagrams Gp1, Gp2. If, for example, the submerged area is selected as the guidance area, as illustrated in FIG. 38, an arrow Y21g corresponding to a tilting operation, an arrow Y22g corresponding to a rotation operation, an arrow Y23g corresponding to a backward operation or forward operation, an arrow Y24g corresponding to a right operation or left operation, and an arrow Y25g corresponding to an up operation or down operation are displayed in the posture diagrams Gp1, Gp2. If, for example, the liquid bottom area is selected as the guidance area, as illustrated in FIG. 39, an arrow Y31g corresponding to a tilting operation and an arrow Y32g corresponding to a rotation operation are displayed in the posture diagrams Gp1, Gp2. By checking the posture diagrams Gp1, Gp2, the operator can easily grasp and select each operation that can be performed in the currently selected guidance area. If the liquid surface area is selected as the guidance area, a line Lws indicating the liquid surface Ws as shown in FIG. 40(1) may be displayed in the posture diagrams Gp1, Gp2. If the liquid bottom area is selected as the guidance area, a line Lst indicating the lower surface of the stomach wall as shown in FIG. 40(3) may be displayed in the posture diagrams Gp1, Gp2. If the submerged area is selected as the guidance area, as shown in FIG. 40(2), no line is shown. With the above display, the operator can easily determine in which area the guidance area is located.

Figure 41:
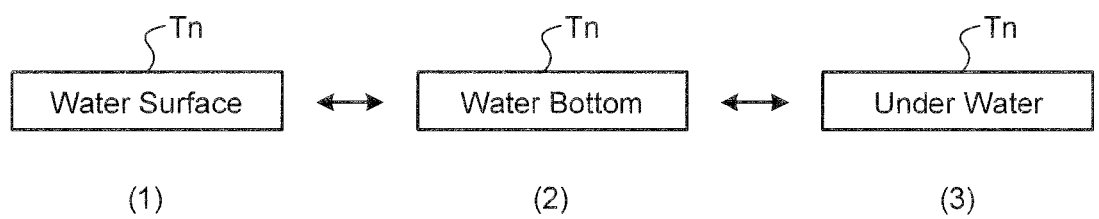
FIG. 41 is a diagram illustrating a guidance area field shown in FIG. 36.

The display unit 5 displays a guidance area field Tn showing the currently selected guidance area in an area A12 positioned in a right direction from the area A11 of the guidance menu M1 shown in FIG. 36. The display unit 5 displays text indicating the liquid surface area if, as shown in FIG. 41(1), the liquid surface area is selected as the guidance area, text indicating the submerged area if, as shown in FIG. 41(2), the submerged area is selected as the guidance area, and text indicating the liquid bottom area if, as shown in FIG. 41(3), the liquid bottom area is selected as the guidance area, in the guidance area field Tn. By checking the guidance area field Tn, the operator can easily grasp the currently selected guidance area.

Figure 42:
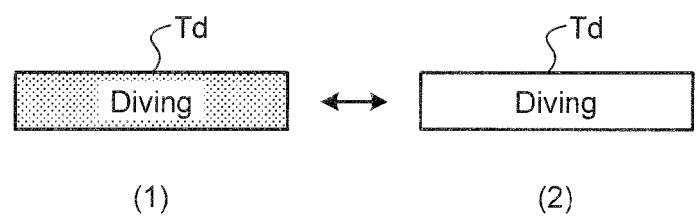
FIG. 42 is a diagram illustrating a diving mode field shown in FIG. 36.

The display unit 5 also displays a diving mode field Td indicating the ON state or OFF state of the diving mode described below and an approach mode field Ta indicating the ON state or OFF state of the approach mode in an area A13 positioned below the area A12 in the guidance menu M1 shown in FIG. 36. The display unit 5 displays the diving mode field Td darker, as shown in FIG. 42(1), when the diving mode is in the OFF state and brighter, as shown in FIG. 42(2), when the diving mode is in the ON state. This also applies to the approach mode field Ta.

The display unit 5 also displays a magnetic field generation allowed area in the horizontal plane in an area A14 below the area A11. The display unit 5 shows the peak position of a peak magnetic field as illustrated by a point Gc in the magnetic field generation allowed area of the area A14. If the liquid surface area is selected as the guidance area, the capsule endoscope 10 may be considered to be positioned in the peak position shown in the magnetic field generation allowed area when a peak magnetic field is generated because the capsule endoscope 10 is trapped in the peak position. Thus, by checking the peak position shown in the area A14, the operator can easily grasp the horizontal position of the capsule endoscope 10.

Figure 43:
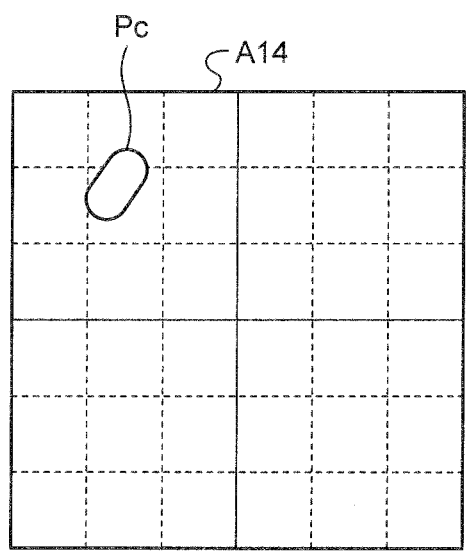
FIG. 43 is a diagram illustrating a magnetic field generation allowed area shown in FIG. 36.

By displaying, as indicated by a capsule endoscope image Pc in FIG. 43, an image when the capsule endoscope 10 is viewed from the vertical direction in the peak position, the operator may be enabled to grasp the position and posture of the capsule endoscope 10 simultaneously. The posture of the capsule endoscope 10 is estimated based on the direction of a magnetic field generated by the magnetic field generation unit 2. When the capsule endoscope 10 is guided by a uniform gradient magnetic field, the peak position in the magnetic field generation allowed area is not displayed. When the type of magnetic field is switched from the uniform gradient magnetic field to the peak magnetic field, the peak position is displayed again in the magnetic field generation allowed area.

Next, the observation menu M2 will be described. The display unit 5 displays subject information such as the patient name, patient ID, sex, and age of a subject in an upper left area A21 of the observation menu M2. Then, the display unit 5 displays an organism image G1 captured by the imaging unit 11A on the left side from the center of the observation menu M2 and an organism image G2 captured by the imaging unit 11B on the right side from the center of the observation menu M2. The display unit 5 displays a marker Ts corresponding to the liquid surface area, a marker Tb corresponding to the submerged area, and a marker Tu corresponding to the liquid bottom area in an area A22 between these organism images G1, G2 and displays the marker corresponding to the selected guidance area brighter than markers of other unselected guidance areas. In the example in FIG. 36, the marker Tu corresponding to the liquid bottom area is brighter. Thus, the operator can easily grasp the currently selected guidance area by checking the display state of the markers Ts, Tb, and Tu displayed near the images G1, G2 together with each of images G1, G2 captured by the capsule endoscope 10 without checking the guidance area field Tn of the guidance menu M1. The display unit 5 also displays each image captured by pressing the capture button 65 as a reduced image together with a capture time in an area A23 below the images G1, G2.

The display unit 5 displays various buttons related to operations other than guidance operation of the capsule endoscope 10 in an area A25 below the area A21 of the observation menu M2. While a magnetic field is generated by the magnetic field generation unit 2, that is, the capsule endoscope 10 is operated to guide, only the operation related to guidance is enabled and input related to other operations is disabled. As a result, the operator can concentrate on the guidance operation so that a stable guidance operation environment can be provided. When communication data signifying generation of a magnetic field by the magnetic field generation unit 2 is received from the external control unit 4, the image display control unit 42 makes inoperable, that is, disables each button displayed in the area A25. When communication data signifying the stop of a magnetic field by the magnetic field generation unit 2 is received from the external control unit 4, the image display control unit 42 makes operable, that is, enables each button displayed in the area A25.

The display unit 5 displays, for example, a Comment button Tp1 having a function to enter a comment during examination, an Exam.List button Tp2 having a function to display past examination data as a list, an Adjustment button Tp3 having a function to adjust the color tone or enhancement level of a display image, a (HIGH/LOW) ENH.HIGH/LOW button Tp4 of the enhancement level of a display image (the example in FIG. 36 shows a case when the LOW level is selected), a ZoomIn button Tp5 having a function to enlarge the size of a display image, a ZoomOut button Tp6 having a function to reduce the size of a display image, a ScaleA button Tp7 having a function to select the type of posture information (dial gauge) displayed in the perimeter of an image, and a Capture button Tp8 having a function to capture a displayed image, in the area A25. The display unit 5 displays images captured by the Capture button Tp8 in the area A23 as reduced images.

The display unit 5 displays an Exam.End button Te having a function to end an examination and to store examination data above the area A25 of the observation menu M2. The image display control unit 42 always makes operable, that is, enables the Exam.End button Te. Thus, while a magnetic field is generated by the magnetic field generation unit 2, that is, the capsule endoscope 10 is operated to guide or in other situations, examination data can be determined (stored). Accordingly, even if communication with the magnetic field control unit 8 fails and communication cannot be restored immediately, examination data can be protected by selecting the Exam.End button Te. The display unit 5 displays an AddPatient button Tad having a function to register patient information and to start an examination on the left side of the Exam.End button Te.

Figure 44:
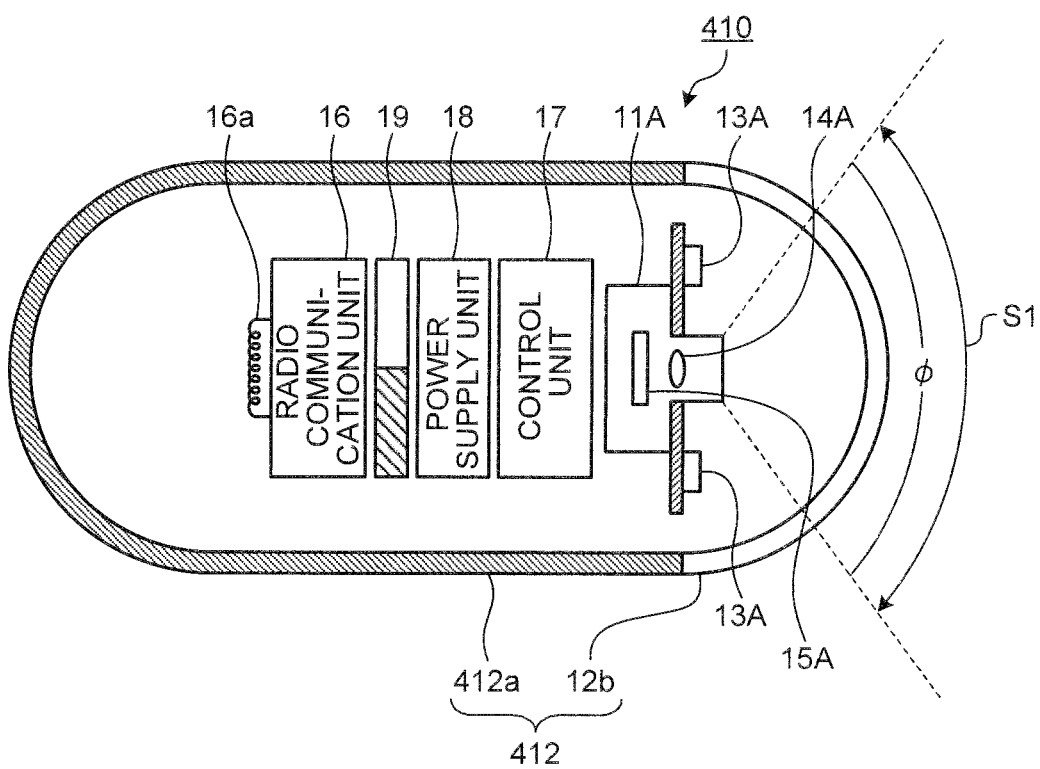
FIG. 44 is a sectional schematic diagram showing another configuration example of the capsule endoscope shown in FIG. 1.

The first to third embodiments have been described by taking the capsule endoscope 10 having a plurality of imaging units as an example, but as shown in FIG. 44, a capsule endoscope 410 having the single imaging unit 11A may also be adopted. In this case, a capsule-shaped casing 412 has a configuration in which one opening end of a cylindrical casing 412*a* is closed by the dome-shaped casing 12*b*.

The first to third embodiments have been described by taking the capsule endoscope 10 using the permanent magnet 19 as an example, but the present invention is not limited to this and a capsule endoscope including an electromagnet, instead of the permanent magnet 19, may be adopted.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A capsule medical device guidance system, comprising:
   a capsule medical device to be introduced into a subject, the capsule medical device including an imaging unit that captures an in-vivo image of the subject, a transmitting unit that transmits the image captured by the imaging unit to an outside, and a magnetic field response unit;
   a magnetic field generation unit that generates a magnetic field for the magnetic field response unit to magnetically guide the capsule medical device;
   a receiving unit that receives the in-vivo image of the subject transmitted by the capsule medical device;
   a display unit that displays the in-vivo image of the subject received by the receiving unit;
   an operation input unit that inputs operation information for magnetically guiding the capsule medical device;
   a control unit that controls the magnetic field generation unit to guide the capsule medical device in accordance with the operation information input by the operation input unit; and
   a selection unit having a switch corresponding to each of two or more guidance areas into which the capsule medical device is guided, the two or more guidance areas including two or more of a liquid surface that is an upper boundary surface between a liquid inside the subject and the outside, a submerged area, and a liquid bottom that is a lower boundary surface between the liquid and the outside, wherein
   the control unit switches the magnetic field to be generated by the magnetic field generation unit in accordance with the guidance area selected by the selection unit.

2. The capsule medical device guidance system according to claim 1, wherein
   the control unit switches at least one of a guidance direction of the capsule medical device by the magnetic field to be generated by the magnetic field generation unit, a type of the magnetic field to be generated by the magnetic field generation unit, and a magnitude and orientation of a magnetic gradient generated in a vertical direction in accordance with the guidance area selected by the selection unit.

3. The capsule medical device guidance system according to claim 2, wherein
   the control unit switches the type of the magnetic field to be generated by the magnetic field generation unit to either a trapping magnetic field that traps the capsule medical device by attracting the magnetic field response unit to any position in a horizontal plane or a gradient magnetic field that has the substantially uniform magnetic gradient and energizes the magnetic field response unit in accordance with the guidance area selected by the selection unit.

4. The capsule medical device guidance system according to claim 1, wherein
   the selection unit selects the guidance area from the combinations containing at least the liquid surface and
   if the guidance area selected by the selection unit is switched from the liquid surface to the submerged area or the liquid bottom, the control unit causes the magnetic field generation unit to generate the magnetic field that can resist a surface tension of the liquid to guide the capsule medical device from the liquid surface to the submerged area or the liquid bottom.

5. A method for operating a capsule medical device guidance system that magnetically guides a capsule medical device to be introduced into a subject, the capsule medical device including an imaging unit that captures an in-vivo image of the subject, a transmitting unit that transmits the image captured by the imaging unit to an outside, and a magnetic field response unit, the capsule medical device guiding method comprising:

receiving, by a receiving device, the in-vivo image of the subject transmitted by the capsule medical device;

displaying the received in-vivo image of the subject by a display device;

selecting, by a selection unit, a switch corresponding to each of two or more guidance areas into which the capsule medical device is guided, the two or more guidance areas including two or more of a liquid surface that is an upper boundary surface between a liquid inside the subject and the outside, a submerged area, and a liquid bottom that is a lower boundary surface between the liquid and the outside; and causing, by a control unit, a magnetic field generation device to generate a magnetic field to guide the capsule medical device in accordance with the selected guidance area.

6. The capsule medical device guidance system according to claim 1, wherein the switches are button switches.

* * * * *